US007022528B2

(12) United States Patent
Avdeef et al.

(10) Patent No.: US 7,022,528 B2
(45) Date of Patent: Apr. 4, 2006

(54) METHOD AND APPARATUS FOR IMPROVING IN VITRO MEASUREMENT OF MEMBRANE PERMEABILITY OF CHEMICAL COMPOUNDS

(75) Inventors: Alex Avdeef, Boston, MA (US); Per E. Nielsen, Westlake, OH (US); Chau M. Du, Allston, MA (US)

(73) Assignee: Pion, Inc., Woburn, MA (US)

( * ) Notice: Subject to any disclaimer, the term of this patent is extended or adjusted under 35 U.S.C. 154(b) by 494 days.

(21) Appl. No.: 10/351,263

(22) Filed: Jan. 23, 2003

(65) Prior Publication Data

US 2003/0219716 A1    Nov. 27, 2003

Related U.S. Application Data

(60) Provisional application No. 60/353,914, filed on Jan. 31, 2002.

(51) Int. Cl.
*G01N 21/76* (2006.01)
(52) U.S. Cl. .................. 436/172; 436/171; 436/50
(58) Field of Classification Search .................. None
See application file for complete search history.

(56) References Cited

U.S. PATENT DOCUMENTS

| 4,812,407 A | 3/1989 | Buchmann et al. | ......... 435/291 |
| 2002/0004244 A1 | 1/2002 | Avdeef et al. | ............... 436/171 |

FOREIGN PATENT DOCUMENTS

| DE | 101 18 725 A1 | 10/2002 |
| WO | WO 03/003007 A2 | 1/2003 |

OTHER PUBLICATIONS

*Drug absorption in vitro model: filter-immobilized artificial membranes 2. Studies of the permeability properties of lactones in Piper methysticum Forst*; Avdeef et al., European Journal of Pharmaceutical Sciences, www.elsevier.nl/locate/ejps, pp. 271-280.
*Physicochemical Profiling (Solubility, Permeability and Charge State)*; Alex Avdeef, Current Topics in Medicinal Chemistry 2001, Bentham Science Publishers Ltd., pp. 277-351.

(Continued)

*Primary Examiner*—Yelena G. Gakh
(74) *Attorney, Agent, or Firm*—Weingarten, Schurgin, Gagnebin & Lebovici LLP

(57) ABSTRACT

This invention improves the PAMPA (parallel artificial membrane permeability assay) method used in pharmaceutical, biotechnological, and agrochemical R&D. This new high-throughput method and apparatus for measurement of permeability and membrane retention of compounds overcomes shortcomings of prior art and includes sensitivity and speed enhancing reagents. The phospholipid membranes used here consist of 10–74% wt/vol soybean lecithin extract dissolved in dodecane. Concentrations are measured by direct UV spectroscopy. To reduce membrane retention, surfactants, cyclodextrins, or water-soluble lipophilic polymers with low UV absorption are used in the acceptor comparment of the permeation cells and create an artificial sink state. A pH gradient established between donor and acceptor solutions creates a secondary sink state. This "double-sink" makes successful modeling of passive-diffusion transport of molecules possible. By accelerating transport of certain molecules, it shortens measurement time and increases assay throughput. A new permeability equation accounts for the "double-sink" condition as well as membrane retention.

26 Claims, 35 Drawing Sheets

OTHER PUBLICATIONS

*Physicochemical High Throughput Screening: Parallel Artificial Membrane Permeation Assay in the Description of Passive Absorption Processes*; Manfred Kansy, et al, Journal of Medicinal Chemistry, vol. 41, No. 7, Mar. 26, 1998, pp. 1007-1010.

*High-Throughput Permeability pH Profile and High-Throughput Alkane/Water log P with Artificial Membranes*; Frank Wohnsland, et al., Novartis Pharma AG, WKL-122. P.33, CH-4002 Basel, Switzerland, Journal of Medicinal Chemistry, 2001, vol. 44, pp. 923-930.

*Optimized conditions of bio-mimetic artificial membrane permeation assay*; Kiyohiko Sugano, et al.; International Journal of Pharmaceutics 228 (2001), pp. 181-188.

*A comparative study of artificial membrane permeability assay for high throughput profiling of drug absorption potential*; Chengyue Zhu, et al., European Journal of Medicinal Chemistry 37 (2002), pp. 399-407.

*Solid-Supported Lipid Membranes as a Tool for Determination of Membrane Affinity: High-Throughput Screening Of a Physicochemical Parameter; A. Loidl-Stahlhofen et al.; Journal of Pharmaceutical Sciences, vol. 90, No. 5, May 2001.

*Physiocochemical Profiling in Drug Research: A Brief Survey of the State-of-the-Art of Experimental Techniques; A. Avdeef et al.; CMLS Cellular and Molecular Life Sciences59 (2002) pp. 1681-1689.

FIG. 15(a)

Table 1 Pharmacokinetic and Physicochemical Properties of Selected Probe Drugs [a]

| Sample | % HIA | Human Jejunal $P_e$ $(10^{-4}$ cm/s) | log $K_d^{7.4}$ | log $K_p$ | $I = 0.01$ $pK_{a1}$ | $pK_{a2}$ | $pK_{a3}$ | Charge Profile | pH 7.4 $f_u$ | Type |
|---|---|---|---|---|---|---|---|---|---|---|
| Chlorpromazine | 100 | | 3.45 | 5.40 | 9.24 | | | + > o | 0.01 | base |
| Phenazopyridine | | | 3.31 | 3.31 | 5.15 | | | + > o | 0.99 | base |
| Verapamil | 95 | 6.7 | 2.51 | 4.44 | 9.07 | | | + > o | 0.02 | base |
| Promethazine | 80 | | 2.44 | 4.05 | 9.00 | | | + > o | 0.02 | base |
| Quinine | 80 | | 2.19 | 3.50 | 4.09 | 8.55 | | ‡ > + > o | 0.07 | base |
| Imipramine | 99 | | 2.17 | 4.39 | 9.51 | | | + > o | 0.008 | base |
| Diltiazem | 99 | | 2.16 | 2.89 | 8.02 | | | + > o | 0.19 | base |
| Prazosin | 50 | | 2.00 | 2.18 | 7.11 | | | + > o | 0.66 | base |
| Propranolol | 99 | 2.9 | 1.41 | 3.48 | 9.53 | | | + > o | 0.007 | base |
| Desipramine | 95 | 4.4 | 1.38 | 3.79 | 10.16 | | | + > o | 0.002 | base |
| Primaquine | 100 | | 1.17 | 3.00 | 3.55 | 10.03 | | ‡ > + > o | 0.002 | base |
| Alprenolol | 93 | | 0.86 | 2.99 | 9.51 | | | + > o | 0.008 | base |
| Metoprolol | 95 | 1.3 | −0.24 | 1.95 | 9.56 | | | + > o | 0.007 | base |
| Ranitidine | 50 | 0.43 | −0.53 | 1.28 | 1.96 | 8.31 | | ‡ > + > o | 0.11 | base |
| Amiloride | 50 | | −0.60 | −0.26 | 8.65 | | | + > ± | 0.000 | base |
| Ibuprofen | 80 | | 1.44 | 4.13 | 4.59 | | | o > − | 0.002 | acid |
| Acetaminophen | 100 | | 0.34 | 0.34 | 9.78 | | | o > − | 1.00 | acid |
| Naproxen | 99 | 8.8 | 0.09 | 3.24 | 4.32 | | | o > − | 0.001 | acid |
| Sulphasalazine | 13 | | 0.08 | 3.61 | 2.80 | 8.25 | 10.96 | o > − > = > ≡ | 0.000 | acid |
| Theophylline | 98 | | 0.00 | 0.00 | 8.70 | | | o > − | 0.95 | acid |
| Ketoprofen | 100 | 8.4 | −0.11 | 3.16 | 4.12 | | | o > − | 0.001 | acid |
| Hydrochlorothiazide | 67 | 0.04 | −0.18 | −0.03 | 8.91 | 10.25 | | o > − > = | 0.97 | acid |
| Furosemide | 61 | 0.05 | −0.24 | 2.56 | 3.67 | 10.93 | | o > − > = | 0.000 | acid |
| Salicyclic acid | 100 | | −1.68 | 2.19 | 3.02 | | | o > − | 0.000 | acid |
| Piroxicam | 100 | 7.8 | 0.00 | 1.98 | 2.33 | 5.22 | | + > o > − | 0.007 | ampholyte |
| Sulpiride | 35 | | −1.15 | 1.31 | 9.12 | 10.14 | | + > o > − | 0.05 | ampholyte |
| Terbutaline | 60 | 0.3 | −1.35 | −0.08 | 8.67 | 10.12 | 11.32 | + > ± > − > = | 0.02 | zwitterion |
| Progesterone | 91 | | 3.89 | 3.89 | | | | o | 1.00 | neutral |
| Griseofulvin | 28 | | 2.18 | 2.18 | | | | o | 1.00 | neutral |
| Carbamazepine | 100 | 4.3 | 2.45 | 2.45 | | | | o | 1.00 | neutral |
| Antipyrine | 100 | 4.5 | 0.56 | 0.56 | | | | o | 1.00 | neutral |
| Caffeine | 100 | | −0.07 | −0.07 | | | | o | 1.00 | neutral |

[a] % HIA human intestinal absorption fraction, oral dose taking; log $K_d^{7.4}$ apparent octanol-water partition coefficient; log $K_p$ octanol-water partition coefficient; $pK_a$ are ionization constants at 0.01 M ionic strength; charge profile: the order in which charges on molecules change as pH is raised from 2 to 10. E.g., terbutaline: for pH < 8.67 ($pK_{a1}$), the main species in solution is a cation ('+'); for pH between 8.67 and 10.12, a zwitterion exists ('±'); between pH 10.12 and 11.32, an anion forms ('−'); and for pH > 11.32, the dianion predominates ('='). The symbol '>' means transition in charge state when pH is increased. The fraction of the molecule in the uncharged form at pH 7.4 is represented by $f_u$.

FIG. 15(b)

Table 2  Neutral Lipid PAMPA Models, pH 7.4 [a]

|  | 2% DOPC (model 1.0) | | | OCTANOL (model 2.0) | | | DODECANE (model 3.0) | | |
|---|---|---|---|---|---|---|---|---|---|
| Sample | $P_e$ | (SD) | %R | $P_e$ | (SD) | %R | $P_e$ | (SD) | %R |
| Chlorpromazine | 5.5 | (0.4) | 85 | 0.000 | (0.005) | 90 | 2.8 | (1.2) | 89 |
| Phenazopyridine | 8.4 | (1.1) | 70 | 1.7 | (0.2) | 87 | 12.7 | (1.6) | 23 |
| Verapamil | 9.7 | (1.0) | 39 | 2.4 | (0.3) | 72 | 11.9 | (1.0) | 28 |
| Promethazine | 7.3 | (0.7) | 70 | 2.4 | (0.2) | 82 | 6.8 | (1.4) | 67 |
| Quinine | 3.1 | (0.6) | 1 | 5.2 | (0.2) | 63 | 2.8 | (0.2) | 10 |
| Imipramine | 11.1 | (0.8) | 56 | 4.2 | (0.1) | 76 | 8.5 | (3.0) | 55 |
| Diltiazem | 17.4 | (1.8) | 21 | 5.4 | (1.2) | 50 | 9.7 | (0.1) | 10 |
| Prazosin | 0.38 | (0.07) | 15 | 5.6 | (0.2) | 52 | 0.11 | (0.03) | 10 |
| Propranolol | 10.0 | (0.5) | 18 | 9.3 | (0.2) | 33 | 7.6 | (0.1) | 11 |
| Desipramine | 12.3 | (0.4) | 40 | 9.8 | (0.6) | 42 | 12.9 | (1.1) | 9 |
| Primaquine | 1.4 | (0.1) | 70 | 9.2 | (0.1) | 22 | 2.0 | (0.1) | 6 |
| Alprenolol | 11.8 | (0.3) | 16 | | | | | | |
| Metoprolol | 0.69 | (0.04) | 11 | 7.1 | (0.1) | 16 | 1.1 | (0.1) | 4 |
| Ranitidine | 0.009 | (0.004) | 2 | 2.6 | (0.1) | 13 | 0.000 | (0.005) | 2 |
| Amiloride | 0.002 | (0.005) | 0 | 5.4 | (0.4) | 14 | 0.01 | (0.01) | 2 |
| Ibuprofen | 2.7 | (0.5) | 38 | 16.6 | (8.3) | 34 | 1.9 | (0.5) | 0 |
| Acetaminophen | 0.001 | (0.005) | 1 | | | | | | |
| Naproxen | 0.33 | (0.03) | 4 | 10.5 | (0.7) | 14 | 0.31 | (0.12) | 4 |
| Sulphasalazine | 0.007 | (0.004) | 1 | 3.0 | (0.1) | 11 | 0.008 | (0.005) | 3 |
| Theophylline | 0.04 | (0.01) | 1 | 10.5 | (0.1) | 12 | 0.23 | (0.05) | 1 |
| Ketoprofen | 0.05 | (0.01) | 4 | 7.8 | (0.2) | 13 | 0.04 | (0.04) | 1 |
| Hydrochloro-thiazide | 0.01 | (0.01) | 1 | 7.8 | (0.1) | 14 | 0.009 | (0.005) | 1 |
| Furosemide | 0.02 | (0.01) | 1 | 1.0 | (0.1) | 12 | 0.02 | (0.04) | 0 |
| Salicyclic acid | 0.006 | (0.004) | 1 | | | | 0.004 | (0.006) | 7 |
| Piroxicam | 2.2 | (0.1) | 3 | 6.9 | (0.1) | 18 | 2.6 | (0.2) | 1 |
| Sulpiride | 0.01 | (0.01) | 1 | 1.9 | (0.1) | 11 | 0.000 | (0.005) | 0 |
| Terbutaline | 0.04 | (0.01) | 6 | 1.9 | (0.2) | 14 | 0.20 | (0.17) | 0 |
| Progesterone | 6.3 | (0.5) | 84 | 0.1 | (0.1) | 91 | 3.7 | (0.7) | 82 |
| Griseofulvin | 12.8 | (1.2) | 18 | 6.5 | (0.6) | 62 | 9.2 | (0.4) | 10 |
| Carbamazepine | 7.1 | (0.3) | 10 | 9.4 | (0.2) | 40 | 6.4 | (0.3) | 6 |
| Antipyrine | 0.7 | (0.1) | 13 | 12.3 | (0.9) | 15 | 1.4 | (0.1) | 4 |
| Caffeine | 1.6 | (0.1) | 2 | 10.6 | (0.2) | 13 | 1.7 | (0.1) | 1 |

[a] All $P_e$ and SD($P_e$) are in units of $10^{-6}$ cm s$^{-1}$.

FIG. 15(c)

Table 3 Egg Lecithin 10% wt/vol in Dodecane PAMPA Models, pH 7.4 [a]

| Sample | Sigma (model 4.0) no SINK | | | Sigma (model 4.1) SINK | | | Sigma +0.5% Cholesterol (model 5.0) no SINK | | | Sigma +0.5% Cholesterol (model 5.1) SINK | | |
|---|---|---|---|---|---|---|---|---|---|---|---|---|
| | $P_e$ | (SD) | %R | $P_e$ | (SD) | %R | $P_e$ | (SD) | %R | $P_e$ | (SD) | %R |
| Chlorpromazine | 1.2 | | 84 | 31.9 | (6.1) | 41 | 0.7 | (0.3) | 86 | 32.1 | (8.6) | 31 |
| Phenazopyridine | 2.7 | (0.1) | 84 | 17.4 | (1.5) | 55 | 3.1 | (0.3) | 86 | 18.8 | (1.7) | 50 |
| Verapamil | 3.1 | (0.5) | 69 | 25.4 | (5.8) | 33 | 1.8 | (1.2) | 83 | 28.4 | (3.1) | 23 |
| Promethazine | 2.2 | (0.3) | 84 | 35.3 | (0.5) | 35 | 1.3 | (0.4) | 89 | 36.4 | (3.5) | 22 |
| Quinine | 4.6 | (0.7) | 52 | 9.6 | (0.5) | 48 | 4.0 | (0.7) | 59 | 12.8 | (0.6) | 39 |
| Imipramine | 2.5 | | 74 | 34.3 | (1.0) | 40 | 3.8 | (0.3) | 75 | 35.3 | (6.3) | 34 |
| Diltiazem | 7.1 | (3.0) | 50 | 31.3 | (4.9) | 18 | 3.8 | (0.2) | 64 | 33.2 | (3.8) | 8 |
| Prazosin | 5.3 | (0.5) | 34 | 11.8 | (0.3) | 21 | 4.4 | (0.4) | 38 | 16.9 | (1.1) | 16 |
| Propranolol | 4.1 | (1.6) | 65 | 21.2 | (0.8) | 43 | 3.5 | (0.3) | 70 | 22.3 | (0.5) | 34 |
| Desipramine | 3.9 | (0.7) | 78 | 24.3 | (7.5) | 49 | 2.7 | (0.3) | 80 | 29.2 | (8.6) | 30 |
| Primaquine | 4.4 | (0.7) | 65 | 22.8 | (1.2) | 36 | 4.4 | (0.8) | 81 | 30.0 | (0.9) | 26 |
| Alprenolol | | | | | | | 5.5 | (0.2) | 65 | | | |
| Metoprolol | 4.0 | | 26 | 4.3 | (0.4) | 22 | 3.7 | (0.1) | 26 | 8.0 | (0.9) | 12 |
| Ranitidine | 0.3 | | 2 | (nd) | | 9 | 0.1 | (0.1) | 7 | (nd) | | 11 |
| Amiloride | (nd) | | 5 | (nd) | | 4 | 0.02 | (0.03) | 3 | (nd) | | 3 |
| Ibuprofen | (nd) | | 47 | (nd) | | | 6.9 | (3.9) | 31 | (nd) | | |
| Naproxen | 1.3 | | 6 | (nd) | | 6 | 1.0 | (0.1) | 6 | 1.3 | (0.6) | 3 |
| Sulphasalazine | 0.05 | | 4 | (nd) | | 4 | | | | 0.04 | (0.06) | 2 |
| Theophylline | 0.2 | | 11 | (nd) | | 6 | 0.3 | (0.1) | 4 | 0.2 | (0.2) | 7 |
| Ketoprofen | 0.3 | (0.1) | 8 | 0.1 | (0.1) | | 0.3 | (0.1) | 5 | 0.4 | (0.1) | 2 |
| Hydrochloro-thiazide | (nd) | | 5 | (nd) | | 1 | 0.006 | (0.005) | 4 | (nd) | | 3 |
| Furosemide | (nd) | | 5 | (nd) | | 4 | 0.01 | (0.01) | 4 | 0.09 | (0.040) | 2 |
| Piroxicam | 2.1 | (0.1) | 8 | 2.2 | (0.1) | 6 | 2.0 | (0.1) | 6 | 2.2 | (0.1) | 4 |
| Sulpiride | (nd) | | 9 | (nd) | | 3 | 0.1 | (0.1) | 5 | (nd) | | 3 |
| Terbutaline | (nd) | | 5 | (nd) | | 3 | 0.06 | (0.01) | 0 | (nd) | | 2 |
| Progesterone | 5.2 | (0.6) | 80 | 42.3 | (2.7) | 31 | 4.0 | (0.7) | 88 | 37.9 | (3.2) | 33 |
| Griseofulvin | 9.7 | (2.1) | 46 | 21.4 | (1.4) | 25 | 5.1 | (0.6) | 41 | 21.7 | (0.3) | 21 |
| Carbamazepine | 9.1 | (1.4) | 20 | 13.8 | (12.1) | 20 | 5.1 | (0.2) | 23 | 15.7 | (2.2) | 19 |
| Antipyrine | 1.4 | (0.1) | 7 | 0.9 | (0.2) | 5 | 1.1 | (0.2) | 4 | 1.4 | (0.3) | 3 |
| Caffeine | 2.3 | (0.4) | 9 | 2.0 | (0.1) | 7 | 2.3 | (0.1) | 7 | 2.0 | (0.2) | 4 |

[a] All $P_e$ and SD($P_e$) are in units of $10^{-6}$ cm s$^{-1}$. (nd) = compound not detected in the acceptor compartment.

FIG. 15(d)

Table 4  Soy Lecithin in Dodecane PAMPA Models (no SINK), pH 7.4 [a]

| Sample | 10% Soy (model 6.0) | | | 20% Soy (model 7.0) | | | 20% Soy +0.5% Cholesterol. (model 8.0) | | | 35% Soy (model 9.0) | | | 68% Soy (model 11.0) | | |
|---|---|---|---|---|---|---|---|---|---|---|---|---|---|---|---|
| | $P_e$ | (SD) | %R | $P_e$ | (SD) | %R | $P_e$ | (SD) | %R | $P_e$ | (SD) | %R | $P_e$ | (SD) | %R |
| Phenazopyridine | 5.8 | (0.4) | 95 | 1.1 | (0.4) | 94 | 7.9 | (2.4) | 96 | 4.1 | (1.2) | 98 | 5.3 | (0.5) | 99 |
| Verapamil | 1.4 | (1.3) | 94 | (nd) | | 95 | 0.1 | (0.2) | 96 | 1.6 | (1.5) | 95 | 0.2 | (0.3) | 94 |
| Promethazine | 0.9 | (0.8) | 94 | (nd) | | 97 | 0.8 | (0.7) | 93 | (nd) | | 96 | 0.1 | (0.1) | 97 |
| Quinine | 4.0 | (0.1) | 94 | 2.5 | (2.2) | 96 | 4.5 | (1.4) | 96 | 0.8 | (1.4) | 98 | (nd) | | 98 |
| Imipramine | 0.001 | (0.005) | 98 | 0.2 | (0.4) | 94 | 1.9 | (1.5) | 91 | 3.2 | (1.2) | 95 | 1.8 | (1.7) | 96 |
| Diltiazem | 4.6 | (1.2) | 87 | 7.0 | (0.9) | 92 | 3.2 | (2.5) | 95 | 6.9 | (2.0) | 97 | 2.0 | (1.7) | 90 |
| Prazosin | 6.7 | (0.1) | 57 | 3.5 | (0.1) | 66 | 9.7 | (0.8) | 72 | 5.5 | (0.6) | 79 | 2.2 | (0.1) | 83 |
| Propranolol | 2.4 | (1.3) | 93 | (nd) | | 96 | 1.3 | (0.9) | 92 | 2.8 | (1.4) | 96 | 2.5 | (0.8) | 95 |
| Desipramine | 1.2 | (1.2) | 97 | (nd) | | 95 | 1.1 | (1.6) | 95 | 2.7 | (4.6) | 96 | 3.2 | (3.3) | 91 |
| Alprenolol | 2.5 | (0.9) | 92 | 0.01 | (0.03) | 91 | 4.8 | (1.0) | 93 | 5.6 | (3.8) | 95 | 4.8 | (3.1) | 95 |
| Metoprolol | 6.0 | (0.7) | 44 | 8.6 | (1.8) | 57 | 8.8 | (2.1) | 62 | 7.1 | (1.7) | 70 | 3.2 | (0.1) | 73 |
| Ranitidine | 0.41 | (0.03) | 8 | 0.36 | (0.01) | 15 | | | | 0.43 | (0.02) | 22 | 0.13 | (0.05) | 16 |
| Amiloride | 0.004 | (0.005) | 14 | 0.002 | (0.006) | 12 | (nd) | | 18 | 0.003 | (0.005) | 19 | (nd) | | 0 |
| Ibuprofen | 4.0 | (1.4) | 63 | 5.0 | (0.7) | 23 | 5.7 | (1.1) | 18 | 6.3 | (1.8) | 18 | 1.6 | (1.2) | 30 |
| Acetaminophen | 0.7 | (0.1) | 4 | 1.1 | (0.2) | 14 | | | | 0.8 | (0.1) | 15 | (nd) | | 0 |
| Naproxen | 2.0 | (0.2) | 6 | 3.4 | (0.1) | 9 | 2.2 | (0.1) | 17 | 2.3 | (0.1) | 13 | 0.5 | (0.1) | 2 |
| Sulphasalazine | 0.001 | (0.005) | 1 | 0.006 | (0.007) | -8 | | | | 0.002 | (0.005) | 6 | 0.002 | (0.005) | 3 |
| Theophylline | 0.65 | (0.04) | 6 | 0.79 | (0.08) | 10 | 0.85 | (0.09) | 12 | 0.60 | (0.04) | 3 | 0.10 | (0.02) | 7 |
| Ketoprofen | 1.0 | (0.1) | 4 | 1.4 | (0.1) | 11 | 1.1 | (0.1) | 16 | 1.0 | (0.1) | 16 | 0.2 | (0.1) | 10 |
| Hydrochloro-thiazide | 0.02 | (0.01) | 6 | 0.006 | (0.007) | 12 | (nd) | | 10 | 0.03 | (0.01) | 20 | 0.02 | (0.04) | 3 |
| Furosemide | 0.02 | (0.01) | 4 | 0.03 | (0.01) | 12 | 0.03 | (0.02) | 13 | 0.05 | (0.03) | 18 | 0.01 | (0.01) | 17 |
| Salicyclic acid | 0.13 | (0.01) | 2 | 0.24 | (0.03) | 10 | | | | 0.26 | (0.08) | 14 | 0.03 | (0.03) | 9 |
| Piroxicam | 2.6 | (0.1) | 8 | 3.7 | (0.1) | 10 | 2.8 | (0.1) | 13 | 2.7 | (0.2) | 17 | 1.6 | (0.1) | 8 |
| Sulpiride | 0.19 | (0.03) | 12 | 0.24 | (0.03) | 16 | 0.20 | (0.04) | 14 | 0.18 | (0.02) | 21 | 0.10 | (0.06) | 16 |
| Terbutaline | 0.05 | (0.09) | 10 | 0.01 | (0.01) | 18 | | | | 0.01 | (0.01) | 22 | (nd) | | 12 |
| Progesterone | 5.8 | (0.4) | 91 | 1.8 | (0.2) | 89 | | | | 1.6 | (0.3) | 92 | 2.6 | (0.8) | 93 |
| Griseofulvin | 7.2 | (0.5) | 44 | 6.6 | (0.2) | 55 | 13.8 | (0.9) | 56 | 6.4 | (0.5) | 62 | 5.4 | (0.2) | 73 |
| Carbamazepine | 6.1 | (0.5) | 29 | 10.8 | (0.3) | 38 | 12.7 | (3.1) | 39 | 6.4 | (0.1) | 44 | 5.3 | (0.4) | 55 |
| Antipyrine | 1.2 | (0.1) | 7 | 1.5 | (0.1) | 8 | 1.6 | (0.2) | 15 | 1.3 | (0.5) | 25 | 0.5 | (0.1) | 8 |
| Caffeine | 1.8 | (0.1) | 6 | 2.1 | (0.1) | 10 | 2.3 | (0.1) | 18 | 2.2 | (0.1) | 17 | 1.6 | (0.1) | 13 |

[a] All $P_e$ and SD($P_e$) are in units of $10^{-6}$ cm s$^{-1}$. (nd) = compound not detected in the acceptor compartment.

FIG. 15(e)

Table 5a Soy Lecithin in Dodecane PAMPA Models (with SINK), pH 7.4 [a]

| Sample | 10% Soy (model 6.1) | | | 20% Soy (model 7.1) | | | 20% Soy +0.5% Cholesterol (model 8.1) | | |
|---|---|---|---|---|---|---|---|---|---|
| | $P_e$ | (SD) | %R | $P_e$ | (SD) | %R | $P_e$ | (SD) | %R |
| Chlorpromazine | | | | 34.8 | (6.0) | 47 | 30.9 | (5.2) | 40 |
| Phenazopyridine | 15.8 | (1.4) | 47 | 18.8 | (1.8) | 59 | 18.3 | (1.7) | 63 |
| Verapamil | 25.6 | (1.5) | 31 | 32.0 | (2.8) | 31 | 32.4 | (1.4) | 31 |
| Promethazine | 26.7 | (3.2) | 25 | 27.6 | (0.9) | 33 | 37.0 | (0.9) | 34 |
| Quinine | 24.6 | (4.1) | 44 | 17.7 | (1.0) | 49 | 20.5 | (1.3) | 46 |
| Imipramine | 30.1 | (0.9) | 38 | 22.9 | (0.7) | 40 | 28.5 | (3.4) | 37 |
| Diltiazem | 35.8 | (1.3) | 22 | 35.0 | (2.0) | 19 | 37.4 | (3.8) | 20 |
| Prazosin | 28.6 | (1.3) | 16 | 20.0 | (0.5) | 23 | 36.4 | (3.7) | 15 |
| Propranolol | 27.1 | (3.4) | 39 | 25.9 | (2.1) | 40 | 26.5 | (2.0) | 40 |
| Desipramine | 33.2 | (2.8) | 33 | 29.7 | (0.7) | 40 | 28.5 | (3.2) | 50 |
| Primaquine | | | | 29.0 | (3.8) | 47 | 36.9 | (2.6) | 34 |
| Alprenolol | 30.6 | (3.8) | 30 | 26.3 | (3.5) | 40 | | | |
| Metoprolol | 26.4 | ((0.1) | 27 | 28.6 | (1.2) | 26 | 29.0 | (1.6) | 29 |
| Ranitidine | 0.34 | (0.01) | 8 | 0.31 | (0.03) | 14 | 0.51 | (0.13) | 15 |
| Amiloride | 0.01 | (0.02) | 9 | 0.010 | (0.007) | 15 | 0.1 | (0.1) | 15 |
| Ibuprofen | 3.6 | (1.4) | 32 | 12.0 | (1.0) | 30 | 16.3 | (2.3) | 39 |
| Acetaminophen | 1.2 | (0.2) | 8 | 0.4 | (0.1) | 7 | | | |
| Naproxen | 1.8 | (0.1) | 10 | 2.3 | (0.1) | 12 | 3.9 | (0.5) | 13 |
| Sulphasalazine | 0.001 | (0.005) | 2 | 0.002 | (0.006) | 10 | 0.7 | (0.4) | 11 |
| Theophylline | 0.5 | (0.1) | 7 | 0.8 | (0.1) | 9 | 1.2 | (0.2) | 16 |
| Ketoprofen | 0.8 | (0.1) | 9 | 1.2 | (0.1) | 12 | 1.5 | (0.2) | 19 |
| Hydrochlorothiazide | 0.004 | (0.010) | 11 | 0.006 | (0.007) | 12 | (nd) | | 17 |
| Furosemide | 0.04 | (0.02) | 14 | 0.02 | (0.01) | 12 | 0.09 | (0.08) | 17 |
| Salicyclic acid | 0.2 | (0.2) | 13 | 0.1 | (0.1) | 7 | | | |
| Piroxicam | 2.3 | (0.1) | 6 | 3.1 | (0.2) | 16 | 3.6 | (0.1) | 14 |
| Sulpiride | 0.2 | (0.1) | 6 | 0.1 | (0.1) | 15 | (nd) | | 17 |
| Terbutaline | 0.2 | (0.3) | 14 | 0.003 | (0.009) | 13 | (nd) | | 20 |
| Progesterone | 37.6 | (1.3) | 40 | 27.7 | (1.1) | 34 | 33.2 | (3.2) | 34 |
| Griseofulvin | 31.8 | (1.5) | 25 | 24.4 | (1.3) | 24 | 27.0 | (3.3) | 25 |
| Carbamazepine | 16.5 | (1.7) | 23 | 15.4 | (0.8) | 28 | 21.2 | (0.8) | 30 |
| Antipyrine | 1.6 | (0.1) | 6 | 1.7 | (0.1) | 15 | 2.5 | (0.3) | 19 |
| Caffeine | 1.5 | (0.1) | 8 | 2.0 | (0.1) | 14 | 3.0 | (0.1) | 19 |

[a] All $P_e$ and SD($P_e$) are in units of $10^{-6}$ cm s$^{-1}$. (nd) = compound not detected in the acceptor compartment.

FIG. 15(f)

Table 5b  Soy Lecithin in Dodecane PAMPA Models (with SINK), pH 7.4 [a]

| Sample | 35% Soy (model 9.1) | | | 50% Soy (model 10.1) | | | 74% Soy (model 12.1) | | |
|---|---|---|---|---|---|---|---|---|---|
| | $P_e$ | (SD) | %R | $P_e$ | (SD) | %R | $P_e$ | (SD) | %R |
| Phenazopyridine | 21.1 | (3.5) | 66 | 2.4 | (0.2) | 58 | 3.9 | (1.1) | 75 |
| Verapamil | 42.9 | (4.0) | 43 | 17.5 | (0.1) | 34 | 1.8 | (2.2) | 71 |
| Promethazine | 31.3 | (3.0) | 36 | 25.7 | (2.9) | 45 | 3.7 | (0.3) | 61 |
| Quinine | 27.6 | (1.4) | 55 | 9.6 | (2.7) | 54 | 2.6 | (1.0) | 67 |
| Imipramine | 42.9 | (6.1) | 46 | 5.2 | (4.8) | 63 | 5.0 | (1.8) | 63 |
| Diltiazem | 40.4 | (7.1) | 32 | 20.8 | (1.0) | 36 | 3.5 | (5.3) | 61 |
| Prazosin | 30.9 | (2.4) | 25 | 12.7 | (0.7) | 38 | 0.4 | (0.4) | 49 |
| Propranolol | 27.6 | (4.0) | 54 | 15.9 | (5.0) | 47 | (nd) | | 62 |
| Desipramine | 37.1 | (9.4) | 48 | 18.4 | (3.0) | 39 | 1.7 | (0.7) | 59 |
| Alprenolol | 42.3 | (5.2) | 51 | 7.8 | (2.2) | 52 | 2.6 | (2.6) | 71 |
| Metoprolol | 31.4 | (0.8) | 42 | 11.6 | (0.9) | 43 | 4.0 | (6.9) | 52 |
| Ranitidine | 0.2 | (0.1) | 13 | 0.3 | (0.4) | 8 | (nd) | | 3 |
| Amiloride | 0.02 | (0.05) | 11 | 0.05 | (0.07) | 0 | (nd) | | 5 |
| Ibuprofen | 8.1 | (4.2) | 22 | 16.5 | (3.6) | 13 | 2.0 | (3.4) | 33 |
| Acetaminophen | 1.3 | (1.1) | 15 | 0.4 | (0.5) | 16 | (nd) | | 0 |
| Naproxen | 2.5 | (0.5) | 9 | 1.4 | (0.3) | 11 | 0.2 | (0.3) | 1 |
| Sulphasalazine | 0.04 | (0.02) | 7 | (nd) | | | (nd) | | 2 |
| Theophylline | 0.7 | (0.1) | 8 | 0.4 | (0.3) | 0 | 0.02 | (0.03) | 6 |
| Ketoprofen | 1.3 | (0.6) | 33 | 1.6 | (1.4) | 30 | (nd) | | 4 |
| Hydrochloro-thiazide | 0.03 | (0.04) | 10 | 0.09 | (0.11) | 1 | 0.01 | (0.01) | 5 |
| Furosemide | 0.01 | (0.02) | 16 | (nd) | | 1 | 0.001 | (0.005) | 10 |
| Salicyclic acid | 1.1 | (0.5) | 11 | 0.3 | (0.5) | 5 | 0.2 | (0.3) | 0 |
| Piroxicam | 2.9 | (0.2) | 18 | 1.6 | (0.1) | 13 | 1.0 | (0.2) | 6 |
| Sulpiride | 0.5 | (0.2) | 17 | 0.3 | (0.5) | 2 | 0.1 | (0.2) | 3 |
| Terbutaline | 0.1 | (0.1) | 20 | 1.3 | (1.8) | 22 | (nd) | | 1 |
| Progesterone | 36.2 | (0.5) | 36 | 23.2 | (0.5) | 65 | 31.8 | (7.2) | 39 |
| Griseofulvin | 22.1 | (2.9) | 27 | 14.6 | (1.0) | 37 | 13.4 | (4.5) | 44 |
| Carbamazepine | 15.3 | (2.0) | 27 | 9.9 | (0.4) | 36 | 2.1 | (0.4) | 38 |
| Antipyrine | 1.8 | (1.0) | 18 | 2.5 | (1.4) | 14 | 1.0 | (0.3) | 1 |
| Caffeine | 2.0 | (0.1) | 18 | (nd) | | 9 | 1.2 | (0.3) | 8 |

[a] All $P_e$ and SD($P_e$) are in units of $10^{-6}$ cm s$^{-1}$. (nd) = compound not detected in the acceptor compartment.

FIG. 15(g)

Table 6 Permeability and Retention in 20% wt/vol Soy Lecithin, at Iso-pH 5.0, 6.5, 7.4 with SINK in Acceptor Wells [a]

| SAMPLE | pH 5.0 (Model 14.1) | | pH 6.5 (Model 13.1) | | pH 7.4 (Model 7.1) | |
|---|---|---|---|---|---|---|
| | $P_e$ | %R | $P_e$ | %R | $P_e$ | %R |
| Desipramine | 10.4 | 35 | 19.4 | 35 | 29.7 | 39 |
| Propranolol | 37.4 | 31 | 26.0 | 37 | 25.9 | 40 |
| Verapamil | 9.1 | 30 | 20.7 | 20 | 32.0 | 31 |
| Metoprolol | 2.9 | 17 | 16.1 | 25 | 28.6 | 26 |
| Ranitidine | 0.00 | 4 | 0.03 | 2 | 0.31 | 14 |
| Piroxicam | 10.2 | 24 | 8.9 | 12 | 3.1 | 16 |
| Naproxen | 11.8 | 50 | 6.6 | 12 | 2.3 | 12 |
| Ketoprofen | 9.5 | 37 | 6.5 | 12 | 1.2 | 12 |
| Furosemide | 0.8 | 25 | 0.0 | 2 | 0.0 | 12 |
| Carbamazepine | 19.5 | 27 | 17.9 | 18 | 15.4 | 28 |
| Antipyrine | 0.9 | 17 | 3.0 | 11 | 1.7 | 15 |

[a] All $P_e$ and SD($P_e$) are in units of $10^{-6}$ cm s$^{-1}$.

Table 7 Intrinsic Permeability & the Unstirred Water Layer Permeability Determined from Gradient-pH Dependence of Effective Permeability: 20% Soy Lecithin in Dodecane, SINK in Acceptor

| Compound | $P_o$ (SD)[a] cm/s | log $P_o$ (SD) | $P_u$ (SD)[b] $10^{-6}$ cm/s | log $P_u$ (SD) | MW | $pK_a$ (I = 0.01 M, 25° C) | $pK_a^{FLUX}$ | pH range[c] | n[d] | GOF[e] |
|---|---|---|---|---|---|---|---|---|---|---|
| desipramine | 1.9 (0.8) × $10^{-2}$ | +2.27 (0.19) | 42.1 (4.1) | −4.38 (0.04) | 302.8 | 10.16 | 3.7 | 3.0 to 10.0 | 12 | 2.4 |
| verapamil | 1.1 (0.3) × $10^{+1}$ | +1.03 (0.14) | 41.2 (3.5) | −4.39 (0.04) | 454.6 | 9.07 | 3.9 | 3.0 to 9.0 | 11 | 2.0 |
| propranolol | 6 (2) | +0.79 (0.15) | 41.8 (4.7) | −4.38 (0.05) | 259.3 | 9.53 | 4.5 | 3.0 to 10.0 | 12 | 2.6 |
| metoprolol | 1.3 (0.3) × $10^{-1}$ | −0.88 (0.10) | 41.2 (3.5) | −4.39 (0.04) | 267.4 | 9.56 | 6.0 | 4.8 to 10.0 | 9 | 1.7 |
| quinine | 5.0(0.7) × $10^{-2}$ | −1.30 (0.06) | 15.6 (0.6) | −4.81 (0.02) | 324.4 | 4.09, 8.55 | 5.1 | 3.6 to 10.0 | 11 | 0.7 |
| naproxen | 5.1 (0.4) × $10^{-3}$ | −2.30 (0.04) | 51.8 (1.6) | −4.29 (0.01) | 230.3 | 4.32 | 6.2 | 3.0 to 8.4 | 8 | 0.7 |
| ketoprofen | 3.3 (0.3) × $10^{-3}$ | −2.49 (0.04) | 22.8 (1.0) | −4.64 (0.02) | 254.3 | 4.12 | 6.2 | 3.0 to 8.4 | 8 | 0.7 |
| piroxicam | 7.9 (0.6) × $10^{-4}$ | −3.11 (0.03) | 26.3 (0.8) | −4.58 (0.01) | 331.4 | 2.33, 5.22 | 6.7 | 3.0 to 9.0 | 11 | 0.5 |
| furosemide | 1.3 (0.1) × $10^{-4}$ | −3.90 (0.03) | 17.0 (1.0) | −4.77 (0.03) | 330.8 | 3.67, 10.93 | 4.6 | 3.0 to 6.6 | 7 | 0.4 |
| carbamazepine | 9.4 (0.6) × $10^{-5}$ | −4.03 (0.03) | 44[f] | −4.36 | 236.3 | — | — | 3.0 to 10.0 | 12 | 1.0 |
| ranitidine | 5.6 (0.6) × $10^{-6}$ | −5.25 (0.04) | 19.8 (10.2) | −4.70 (0.22) | 350.9 | 8.31 | 8.2 | 6.0 to 10.0 | 7 | 0.4 |
| antipyrine | 1.4 (0.2) × $10^{-6}$ | −5.86 (0.06) | 17[f] | −4.77 | 188.2 | — | — | 3.0 to 10.0 | 12 | 0.5 |
| terbutaline | 1.2 (0.2) × $10^{-7}$ | −6.91 (0.08) | 17[f] | −4.77 | 274.3 | 8.67, 10.12 | — | 3.0 to 10.0 | 12 | 1.0 |
| hydrochlorothiazide | 5 (6) × $10^{-9}$ | −8.30 (0.49) | 17[f] | −4.77 | 297.7 | 9.81, 10.25 | — | 3.0 to 10.0 | 5 | 0.8 |

[a] $P_o$ = intrinsic permeability. (SD) = estimated standard deviation. [b] $P_u$ = unstirred water permeability. [c] Data range actually used in the regression analysis. [d] Number of $P_e$ measurements. [e] GOF = goodness-of-fit in the weighted nonlinear regression analysis. [f] Carbamazepine, antipyrine, terbutaline and hydrochlorothiazide were treated as neutral molecules. Their effective permeability was corrected for the unstirred water layer using estimated unstirred water layer permeability, determined by the other molecules of similar lipophilicity and size.

FIG. 15(h)

Table 8 Interpolated Effective and Membrane Permeability Determined from Double-Sink Conditions: 20% Soy Lecithin in n-Dodecane

| Compound | pH 5.0 | | | pH 5.5 | | | pH 6.0 | | | pH 6.5 | | | pH 7.4 | | |
|---|---|---|---|---|---|---|---|---|---|---|---|---|---|---|---|
| | $P_e$ $(10^{-6}\,cm/s)$ | $P_m$ $(cm/s)$ | %R | $P_e$ $(10^{-6}\,cm/s)$ | $P_m$ $(cm/s)$ | %R | $P_e$ $(10^{-6}\,cm/s)$ | $P_m$ $(cm/s)$ | %R | $P_e$ $(10^{-6}\,cm/s)$ | $P_m$ $(cm/s)$ | %R | $P_e$ $(10^{-6}\,cm/s)$ | $P_m$ $(cm/s)$ | %R |
| verapamil | 39 | $9.2 \times 10^{-4}$ | 28 | 41 | $2.9 \times 10^{-3}$ | 30 | 41 | $9.2 \times 10^{-3}$ | 29 | 41 | 0.029 | 32 | 41 | 0.23 | 34 |
| quinine | 7 | $1.4 \times 10^{-5}$ | 55 | 12 | $4.5 \times 10^{-5}$ | 56 | 14 | $1.4 \times 10^{-4}$ | 58 | 15 | $4.4 \times 10^{-4}$ | 58 | 16 | $3.3 \times 10^{-3}$ | 59 |
| propranolol | 34 | $1.8 \times 10^{-4}$ | 35 | 39 | $5.7 \times 10^{-4}$ | 38 | 41 | $1.8 \times 10^{-3}$ | 39 | 42 | $5.7 \times 10^{-3}$ | 39 | 42 | 0.045 | 39 |
| desipramine | 41 | $1.3 \times 10^{-3}$ | 34 | 42 | $4.0 \times 10^{-3}$ | 35 | 42 | 0.013 | 36 | 42 | 0.040 | 37 | 42 | 0.32 | 39 |
| metoprolol | 3 | $3.6 \times 10^{-6}$ | 19 | 9 | $1.1 \times 10^{-5}$ | 20 | 19 | $3.6 \times 10^{-5}$ | 24 | 30 | $1.1 \times 10^{-4}$ | 24 | 39 | $9.0 \times 10^{-4}$ | 25 |
| ranitidine | 0.003 | $2.7 \times 10^{-9}$ | 16 | 0.009 | $8.7 \times 10^{-9}$ | 16 | 0.03 | $2.7 \times 10^{-8}$ | 17 | 0.09 | $8.6 \times 10^{-8}$ | 17 | 0.6 | $6.1 \times 10^{-7}$ | 19 |
| naproxen | 49 | $2.7 \times 10^{-4}$ | 22 | 44 | $3.1 \times 10^{-4}$ | 22 | 35 | $1.0 \times 10^{-4}$ | 21 | 20 | $3.3 \times 10^{-5}$ | 20 | 4 | $4.2 \times 10^{-6}$ | 13 |
| ketoprofen | 22 | $3.8 \times 10^{-4}$ | 21 | 19 | $1.3 \times 10^{-4}$ | 21 | 15 | $4.2 \times 10^{-5}$ | 20 | 9 | $1.3 \times 10^{-5}$ | 19 | 2 | $1.7 \times 10^{-6}$ | 16 |
| hydrochloro-thiazide | 0.005 | $5.0 \times 10^{-9}$ | 16 | 0.005 | $5.0 \times 10^{-9}$ | 16 | 0.005 | $5.0 \times 10^{-9}$ | 16 | 0.005 | $5.0 \times 10^{-9}$ | 14 | 0.005 | $5.0 \times 10^{-9}$ | 14 |
| furosemide | 4.2 | $5.6 \times 10^{-6}$ | 42 | 1.7 | $1.8 \times 10^{-6}$ | 34 | 0.6 | $5.9 \times 10^{-7}$ | 32 | 0.2 | $1.9 \times 10^{-7}$ | 24 | 0.02 | $2.3 \times 10^{-8}$ | 19 |
| piroxicam | 25 | $4.9 \times 10^{-4}$ | 28 | 24 | $2.7 \times 10^{-4}$ | 25 | 21 | $1.1 \times 10^{-4}$ | 23 | 16 | $3.9 \times 10^{-5}$ | 17 | 4 | $5.1 \times 10^{-6}$ | 16 |
| terbutaline | 0.1 | $1.2 \times 10^{-7}$ | 18 | 0.1 | $1.2 \times 10^{-7}$ | 18 | 0.1 | $1.2 \times 10^{-7}$ | 18 | 0.1 | $1.2 \times 10^{-7}$ | 19 | 0.1 | $1.2 \times 10^{-7}$ | 19 |
| carbamazepine | 30 | $9.4 \times 10^{-5}$ | 29 | 30 | $9.4 \times 10^{-5}$ | 29 | 30 | $9.4 \times 10^{-5}$ | 29 | 30 | $9.4 \times 10^{-5}$ | 29 | 30 | $9.4 \times 10^{-5}$ | 29 |
| antipyrine | 1.3 | $1.4 \times 10^{-6}$ | 14 | 1.3 | $1.4 \times 10^{-6}$ | 14 | 1.3 | $1.4 \times 10^{-6}$ | 14 | 1.3 | $1.4 \times 10^{-6}$ | 14 | 1.3 | $1.4 \times 10^{-6}$ | 14 |

FIG. 15(i)

Table 9 Effect of 100 mM β-Cyclodextrin in Acceptor Wells in the 20% wt/vol Soy Lecithin System, pH 7.4 [a]

| | no-sink (model 7.0) | | | 100 mM β-CD (model 7.2) | | | 35 mM SLS (model 7.1) | | |
|---|---|---|---|---|---|---|---|---|---|
| Sample | $P_e$ | (SD) | %R | $P_e$ | (SD) | %R | $P_e$ | (SD) | %R |
| Verapamil | (nd) | | 95 | 3.7 | (0.4) | 53 | 32.0 | (2.8) | 31 |
| Propranolol | (nd) | | 96 | 3.3 | (0.4) | 61 | 25.9 | (2.1) | 40 |
| Desipramine | 1.2 | (1.2) | 97 | 9.7 | (4.9) | 56 | 29.7 | (0.7) | 40 |
| Metoprolol | 6.0 | (0.6) | 44 | 20.9 | (0.7) | 26 | 28.6 | (1.2) | 26 |
| Ranitidine | 0.41 | (0.03) | 8 | 0.20 | (0.04) | 10 | 0.31 | (0.03) | 14 |
| Naproxen | 2.0 | (0.2) | 6 | 4.2 | (0.2) | 9 | 2.3 | (0.1) | 12 |
| Ketoprofen | 1.0 | (0.1) | 4 | 1.1 | (0.1) | 11 | 1.2 | (0.1) | 12 |
| Hydrochloro-thiazide | 0.02 | (0.01) | 6 | 0.007 | (0.013) | 9 | 0.006 | (0.007) | 12 |
| Furosemide | 0.02 | (0.01) | 4 | 0.05 | (0.01) | 0 | 0.02 | (0.01) | 12 |
| Piroxicam | 2.6 | (0.1) | 8 | 3.2 | (0.2) | 9 | 3.1 | (0.2) | 16 |
| Terbutaline | 0.05 | (0.09) | 10 | (nd) | | 8 | 0.003 | (0.009) | 13 |
| Carbamazepine | 6.1 | (0.5) | 29 | 23.2 | (0.8) | 25 | 15.4 | (0.8) | 28 |
| Antipyrine | 1.2 | (0.1) | 7 | 2.4 | (0.5) | 8 | 1.7 | (0.1) | 15 |

[a] All $P_e$ and SD($P_e$) are in units of $10^{-6}$ cm s$^{-1}$. (nd) = compound not detected in the acceptor compartment.

FIG. 15(j)

Table 10 Effect of 100 mM β-Cyclodextrin in Donor and Acceptor Wells in the 20% Soy Lecithin System, pH 7.4 [a]

| Sample | no-sink (Model 7.0) | | | 0.1 M β-CD (Model 7.3) | | |
|---|---|---|---|---|---|---|
| | $P_e$ | (SD) | %R | $P_e$ | (SD) | %R |
| Verapamil | (nd) | | 95 | 2.9 | (0.2) | 58 |
| Imipramine | 0.2 | (0.4) | 94 | 5.9 | (0.8) | 37 |
| Diltiazem | 7.0 | (0.9) | 92 | 5.6 | (0.1) | 46 |
| Propranolol | (nd) | | 96 | 0.2 | (0.3) | 10 |
| Alprenolol | 0.01 | (0.03) | 91 | 4.1 | (0.9) | 50 |
| Metoprolol | 8.6 | (1.8) | 57 | 6.4 | (0.6) | 21 |
| Ranitidine | 0.36 | (0.01) | 15 | 0.26 | (0.04) | 9 |
| Acetaminophen | 1.1 | (0.2) | 14 | 0.04 | (0.01) | 0 |
| Sulphasalazine | 0.006 | (0.007) | 8 | 0.04 | (0.06) | 6 |
| Theophylline | 0.8 | (0.1) | 10 | 0.5 | (0.2) | 9 |
| Ketoprofen | 1.4 | (0.1) | 11 | 0.03 | (0.02) | 9 |
| Salicyclic acid | 0.2 | (0.1) | 10 | 0.04 | (0.03) | 8 |
| Piroxicam | 3.7 | (0.1) | 10 | 0.40 | (0.02) | 9 |
| Progesterone | 1.8 | (0.2) | 89 | 6.1 | (0.6) | 9 |
| Caffeine | 2.1 | (0.1) | 10 | 1.9 | (0.3) | 10 |

[a] All $P_e$ and SD($P_e$) are in units of $10^{-6}$ cm s$^{-1}$.

FIG. 15(k)

Table 11 Correlation ($r^2$) between Human Jejunal Permeability and PAMPA Permeability

| Model No: | Type | Membrane Composition | $pH_{DON}/pH_{ACC}$ | No Sink | With Sink |
|---|---|---|---|---|---|
| 1 | neutral | 2% DOPC | 7.4/7.4 | 0.33 | 0.53 |
| 2 | neutral | 100% octanol | 7.4/7.4 | 0.01 | |
| 3 | neutral | 100% dodecane | 7.4/7.4 | 0.32 | |
| 4 | lecithin extracts, anionic | 10% Egg PC (Sigma) | 7.4/7.4 | 0.65 | 0.17 |
| 5 | lecithin extracts, anionic | 10% Egg PC (Sigma) + 0.5% Cholesterol | 7.4/7.4 | 0.58 | 0.57 |
| 6 | lecithin extracts, anionic | 10% Soy PC | 7.4/7.4 | 0.62 | 0.48 |
| 7 | lecithin extracts, anionic | 20% Soy PC | 7.4/7.4 | 0.65 | 0.55 |
| 8 | lecithin extracts, anionic | 20% Soy PC + 0.5% Cholesterol | 7.4/7.4 | 0.56 | 0.63 |
| 9 | lecithin extracts, anionic | 35% Soy PC | 7.4/7.4 | 0.58 | 0.42 |
| 10 | lecithin extracts, anionic | 50% Soy PC | 7.4/7.4 | | 0.36 |
| 11 | lecithin extracts, anionic | 68% Soy PC | 7.4/7.4 | 0.29 | |
| 12 | lecithin extracts, anionic | 74% Soy PC | 7.4/7.4 | | 0.04 |
| 13 | iso-pH | 20% Soy PC | 6.5/6.5 | | 0.77 |
| 14 | iso-pH | 20% Soy PC | 5.0/5.0 | | 0.86 |
| 15 | gradient-pH, corr. UWL | 20% Soy PC | 6.5/7.4 | | 0.52 |
| 16 | gradient-pH, corr. UWL | 20% Soy PC | 6.0/7.4 | | 0.72 |
| 17 | gradient-pH, corr. UWL | 20% Soy PC | 5.5/7.4 | | 0.89 |
| 18 | gradient-pH, corr. UWL | 20% Soy PC | 5.0/7.4 | | 0.97 |
| 19 | gradient-pH, corr. UWL | 20% Soy PC | 4.5/7.4 | | 0.95 |

FIG. 15(I)

METHOD AND APPARATUS FOR IMPROVING IN VITRO MEASUREMENT OF MEMBRANE PERMEABILITY OF CHEMICAL COMPOUNDS

CROSS REFERENCE TO RELATED APPLICATIONS

This application claims priority to U.S. Provisional Application No. 60/353,914 filed Jan. 31, 2002, which is incorporated in its entirety herein.

STATEMENT REGARDING FEDERALLY SPONSORED RESEARCH OR DEVELOPMENT

N/A

FIELD OF THE INVENTION

The measurement of physicochemical properties, such as permeability, in a high-throughput screening environment plays an important role in the selection of the most promising biologically-active molecules for lead optimization in pharmaceutical and biotechnological research and development, and in identifying active compounds with the right plant distribution properties in agrochemical research and development. In this context, PAMPA (parallel artificial membrane permeability assay) has been used for measuring the in vitro permeability of molecules across artificial phospholipid membrane barriers supported by a high-porosity microfilter, separating a solution of test molecules from a solution initially free of them. The invention described here is an improvement of PAMPA. This invention is a robust method and apparatus for the measurement of two physical properties, permeability and membrane retention of compounds. It includes reagents specifically designed for enhancing the sensitivity of the assay, to allow a UV detection system to be used for concentration measurements, to accurately estimate and compensate for the effects of membrane retention and unstirred water layer, and to increase the speed of the assay.

BACKGROUND OF THE INVENTION

High Attrition Rates in Drug Development and the High Cost of Drugs

In pharmaceutical research, looking for a new drug takes place in three stages: exploration, discovery, and development. In the first stage, the understanding of the disease state is accumulated, a therapeutic target is selected, and a biological screening assay is developed. The discovery stage begins with 'hits' finding, where a company's library of compounds is screened for the IC50 value, the concentration of the compound required to displace 50% of a reference ligand from a target receptor. In the course of a year at a large pharmaceutical company, it is not uncommon to have 100,000 to 1,000,000 library compounds tested against a particular target, which is usually a receptor site on a protein molecule. Of the molecules tested for biological activity, about 3000 to 10,000 are found to be active (hits). The initial part of the discovery step is called 'lead' generation, where the most promising subset of the hits is selected for further testing. Of the 3000–10,000 potent molecules, about 400 make it to this step. The selection of leads takes into account biopharmaceutic properties of the hits, such as measured aqueous solubility, octanol-water partition coefficients, plasma stability, human serum protein binding, cytochrome P450 inhibition (oxidative metabolism), liver microsome assay (general metabolism), and membrane permeability, using an in vitro cultured-cell model, such as Caco-2. These various tests filter out many molecules with unfavorable biopharmaceutic ADME properties (absorption, distribution, metabolism, and excretion). Most companies perform fast ADME screens in the hits-to-leads transition to aid in "go—no go" decisions. The selected 400 lead compounds are expected to have good in vivo pharmacokinetic (PK) behavior in animal models developed later. But many of the molecules will underperform in laboratory animals, and will be rejected. In lead optimization, the compounds are rigorously tested for in vitro ADME properties, CNS penetration, selectivity against other similar targets, as well as for cytotoxicity. In the final stages of optimization, where rodent in vivo PK measurements are done, metabolic profiles are developed, and additional animal model toxicity tests are performed, about twelve promising 'candidate' molecules survive to enter pre-clinical development, where dosage form design and human PK, safety, and effectiveness testing begin. During the subsequent clinical phases, the number of clinical development molecules dwindles down to about one, a considerable and expensive downsizing from the original 400 promising leads.

ADME is the single largest cause of attrition in drug development, accounting for 39% of the failures. Methods which can lower this high attrition rate would benefit the industry by reducing failure rates, the pharmaceutical companies by reducing costs, and consumers by helping to get better drugs to market, in less time.

The in vitro cultured-cell permeability model (e.g., Caco-2) used in the hits-to-leads transition mentioned above is very expensive and technically challenging to automate in high-throughput applications. As a result, many companies use Caco-2 screen mainly in lead optimization, as a mechanistic secondary screen. Other types of permeability measurements, based on artificial membranes, have been considered, with the aim of improving efficiency and lowering costs. PAMPA has risen to that challenge, as a cost-effective primary permeability screen, most often applied to the 3000–10,000 hits. Some companies are considering using the assay to screen whole libraries of 100,000–1,000,000 molecules, in a target-independent effort to ferret out molecules with poor biopharmaceutic properties.

Properties of the Gastrointestinal Tract (GIT) and the Blood-Brain Barrier (BBB)

The in vitro measurement of permeability by the cultured-cell and by the current PAMPA models underestimates the true membrane permeability, due to the effect of the unstirred water layer (UWL) adjacent to the two sides of the membrane barrier. This UWL is 1500 to 2500 µm thick. Transport of lipophilic molecules becomes diffusion-limited in the in vitro assays, and lipophilic molecules all show nearly the same effective permeability. In contrast, the UWL in the human small intestine is about 30–100 µm, and it is virtually zero in the BBB. [Avdeef, A. Curr. Topics Med. Chem. 2001, 1, 277–351] Transport of lipophilic molecules in the GIT is membrane-limited, and values of permeability can be several orders of magnitude higher than predicted from the in vitro assays. Thus, correcting the in vitro permeability data for the UWL effect is important for both GIT and BBB absorption modeling.

The in vivo environment of the GIT is characterized by a pH gradient, with pH 7.4 in the receiving compartment (blood), and pH varying in the donor compartment (lumen) from about 5 to 8 from the start to the end of the small intestine. In contrast, the BBB has pH 7.4 on both sides of the barrier. Modeling the GIT and the BBB requires proper pH adjustment in the in vitro models.

The acceptor compartment in the GIT has a prevailing strong sink condition, made possible by the high concentration of proteins, such as human serum albumin (HSA), circulating in the blood. This affects lipophilic molecules, which can strongly bind to the serum proteins. In contrast, comparable binding of lipophilic molecules takes place on both sides of the BBB and there is an absence of a strong circulation system in the brain fluids. Consequently, in the GIT, lipophilic molecules are swept away from the acceptor site of absorption; in the brain, lipophilic molecules have a greater tendency to accumulate in the BBB, compared to the GIT. In practical terms, the in vitro GIT model calls for a sink condition predominantly in the acceptor compartment; the in vitro BBB absorption model would be served well with comparable sink conditions in both acceptor and donor sides.

In the GIT, about 13% of the phospholipids are negatively charged, with the rest being zwitterionic. The negative charge content is about twice as large in the BBB. Factoring this into the in vitro model is expected to be important.

The 'white fat' content of the GIT is higher than that of the BBB. Consequently, the use of triglycerides, cholesterol esters, and cholesterol in the in vitro modeling is thought to be important.

PAMPA (Parallel Artificial Membrane Permeability Assay)

In the early 1960s it was discovered that when a small amount of a phospholipid (2% wt/vol alkane solution) is placed over a pin hole in a thin sheet of plastic suspended in water, a single bilayer (black) lipid membrane (BLM) forms over the hole. Suitable lipids for the spontaneous formation of a BLM are phosphatidylcholine (PC), phosphatidylethanolamine (PE), phosphatidylserine (PS), phosphatidylinositol (PI), and others. BLMs have been viewed as useful biological models, although extremely fragile and tedious to make. Efforts to overcome the limitations of the fragile membranes have evolved with the use of membrane supports, made of porous microfilters.

Kansy et al. [Kansy, M., Senner, F., Gubernator, K., J. Med. Chem. 1998, 41, 1007–1010] reported a study of the permeation of drugs across phospholipid-coated microfilters, using a high-throughput assay they called PAMPA (parallel artificial membrane permeability assay). In this method, a 'sandwich' is formed from a 96-well microtitre plate and a 96-well hydrophobic filter microtitre plate, such that each composite well is divided into two chambers, separated by the microfilter (hydrophobic Immobilon-P IPVH, 125 µm thick, 0.45 µm pores, 70% porosity) coated with a 10% wt/vol dodecane solution of a commercially-available egg lecithin extract. These investigators were able to relate their measured fluxes to human absorption values with a hyperbolic curve, much like that indicated in Caco-2 screening. The outliers in their assay were molecules known to be actively transported and, therefore, not expected to be modeled by PAMPA.

The PAMPA method has attracted a lot of favorable attention, and has spurred the development of a commercial instrument. [Avdeef, A., Strafford, M., Block, E., Balogh, M. P., Chambliss, W., Khan, I., Eur. J. Pharm. Sci. 2001, 14, 271–280] The system reported by Avdeef and coworkers is an improvement of the Kansy approach, with several novel features, including a way to assess membrane retention, and to correct for unstirred water layer effects, [Avdeef, A., Tsinman, K., U.S. Provisional Patent Application No. 60/178,616, Jan. 28, 2000] along with improvements in sensitivity of the UV method originally used by Kansy. A microfilter-immobilized 2% wt/vol dioleoylphosphatidylcholine (DOPC, a high-purity synthetic phosphatidylcholine) dodecane solution was used as a membrane barrier. The iso-pH permeability equation was introduced, [Avdeef, A., Curr. Topics Med. Chem. 2001, 1, 277–351] which directly takes into account the membrane retention of a drug:

$$P_e = -\frac{2.303 V_D}{A(t-\tau_{SS})}\left(\frac{1}{1+V_D/V_A}\right)\log_{10}\left[1-\left(\frac{1+V_A/V_D}{1-R}\right)\frac{C_A(t)}{C_D(0)}\right] \quad (1)$$

where A=area of filter (cm$^2$), t=time (s), $\tau_{SS}$=steady-state time(s), $V_A$ and $V_D$ are the acceptor and donor volumes (cm$^3$), respectively, and $C_A(t)$ and $C_D(t)$ are the measured acceptor and donor sample concentrations (mol cm$^{-3}$) at time t, respectively.

The membrane retention factor, R, is defined as $1-[C_D(t)+C_A(t)\cdot V_A/V_D]/C_D(0)$.

The R factor is often stated as a mole percentage (% R) of the sample (rather than a fraction). Its value can at times be very high, as high as 90% for chlorpromazine and 70% for phenazopyridine, when 2% wt/vol DOPC in dodecane is used. Membrane retention is due to the lipophilicity of molecules. Cultured-cell assays also are subject to sample retention by the cell monolayer. Sawada et al. Sawada, G. A., Barsuhn, C. L., Lutzke, B. S., Houghton, M. E., Padbury, G. E., Ho, N. F. H., Raub, T. J., J. Pharmacol. Exp. Ther. 1999, 288, 1317–1326 cited values as high as 89%. This is undoubtedly a common phenomenon with research compounds, which are often very lipophilic.

Batzl-Hartmann et al. [Batzl-Hartmann, C., Hurst, L., Maas, R., German Patent Application: DE 10118725, Oct. 24, 2002; Priority Application DE 2001-10118725, Apr. 12, 2001] claimed an improved PAMPA, where in addition to the normal Kansy procedure, an extra permeablility measurement was made with hydrophilic PVDF filters, where the lecithin did not entirely plug up the microchannels, allowing for aqueous pore diffusion of hydrophilic (but apparently not lipophilic) molecules. The microchannels in the filters appear to get plugged up after the filter microtitre plate is vigorous aggitated. Similar work, although not called 'PAMPA,' had been reported by Ghosh, [Ghosh, R., J. Mem. Sci. 2001, 192, 145–154] employing octanol-impregnated cellulose microporous filters, where controlled aqueous pores were formed by applying pressure.

Wohnsland and Faller [Wohnsland, F., Faller, B., J. Med. Chem. 2001, 44, 923–930] modified the PAMPA assay using phospholipid-free hexadecane, supported on 10 µm thick polycarbonate filters (3 µm pores, 20% porosity), and were able to demonstrate interesting predictions. Their PAMPA method (based on UV spectrophtometry in 100–200 µM sample solutions) appears to be an excellent substitute for determining alkane-water partition coefficients, which are usually very difficult to measure directly, due to the poor solubility of drug molecules in alkanes. However, since the alkane membrane barrier is inert, hydrogen-bonding and ionic equilibria, found in natural membrane barriers, cannot be modeled. Apparently, membrane retention was not measured.

Sugano and coworkers [Sugano, K., Hamada, H., Machida, M., Ushio, H., Saitoh, K., Terada, K., Int. J. Pharm. 2001, 228, 181–188] explored the lipid model containing several different phospholipids, resembling the mixture found in reconstituted brush-border lipids, and demonstrated improved property predictions. The best-performing composition consisted of a mixture of five lipids (0.8% PC, 0.8% PE, 0.2% PS, 0.2% PI, 1.0% cholesterol) dissolved in 1,7-octadiene. Apparently, membrane retention was not measured. Concentrations of sample solutions (initial donor concentration of 500 μM) were determined by UV spectrophtometry. Although very promising as a mechanistic probe, the multi-phospholipid mixture is expensive. Also, the use of the volatile octadiene requires an extraction hood for safety reasons.

Zhu et al. [Zhu, C., Jiang, L., Chen, T.-M., Hwang, K.-K., Eur. J. Med. Chem. 2002, 37, 399–407] found the use of hydrophilic filters (low protein binding PVDF) as an advantage in lowering the permeation time to 2 h. Egg lecithin, 1% wt/vol in dodecane, was used as the membrane medium. Concentrations of sample solutions (donor at 100–200 μM at time zero) were determined by UV spectrophtometry. Over 90 compounds were characterized at pH 5.5 and 7.4. For each molecule, the greater $P_e$ value of the two measured at different pH was used to compare to Caco-2 permeabilities reported in the literature. It is noteworthy that many ionizable molecules did not follow the permeability-pH dependency expected from the pH partition hypothesis. It may be that water microchannels (cf., Batzl-Hartmann et al.) were contributing to the unexpected permeability-pH trends. Solute retention by the membrane was not considered. Human intestinal absorption (HIA) values were compared to PAMPA measurements, Caco-2 permeability, octanol-water partition coefficients, calculated polar surface area, and published quantitative structure-property relations. It was concluded that PAMPA and Caco-2 measurements best predicted HIA values.

Permeability Effects of PEG400, Bile Acids, and Other Surfactants

Yamashita et al. [Yamashita, S., Furubayashi, T., Kataoka, M., Sakane, T., Sezaki, H., Tokuda, H., Eur. J. Pharm. Sci. 2000, 10, 109–204] added up to 10 mM taurocholic acid, cholic acid, or sodium laurel sulfate (SLS) to the donor solutions in Caco-2 assays. The two bile acids did not interfere in the transport of dexamethasone. However, SLS caused the Caco-2 cell junctions to become more leaky. The permeability of dexamethasone decreased in SLS. Also, they tested the effect of PEG400, with up to 10% added to donor solutions in Caco-2 assays. PEG400 caused a dramatic decrease (75%) in the permeability of dexamethasone at 10% concentration.

Sugano et al. [Sugano, K., Hamada, H., Machida, M., Ushio, H., Saitoh, K., Terada, K., Int. J. Pharm. 2001, 228, 181–188] also studied the effect of PEG400, up to 30% in both the donor and acceptor wells, in their PAMPA assays. The rationale of using additives was to overcome problems in working with very sparingly soluble compounds. PEG400 dramatically reduced permeability for several of the molecules studied.

In Caco-2 assays, serum proteins had been added to the acceptor compartment, to simulate a sink condition. [Sawada, G. A., Ho, N. F. H., Williams, L. R., Barsuhn, C. L., Raub, T. J., Pharm. Res. 1994, 11, 665–673] Also, serum proteins had been added to the donor solutions in several reports.

BRIEF SUMMARY OF THE INVENTION

An improved PAMPA method and apparatus were developed for quickly and accurately determining membrane permeability and membrane retention of test compounds, as a function of pH, under iso- or gradient-pH conditions. The concentrations of test molecules in the donor and acceptor compartments of the permeation cell are rapidly measured by UV spectrophotometry, from which the effective membrane permeability, $P_e$, and membrane retention, % R, parameters are calculated.

Preferably, the PAMPA model membrane barriers are constructed with concentrated phospholipid solutions, 10 to 74% wt/vol soybean lecithin dissolved in dodecane, supported on high-porosity, hydrophobic Immobilon-P IPVH microfilters. This preferred lipid has net negative charge at pH 7.4. This negative charge content is about four times greater than that found in the original egg lecithin formulation used by Kansy.

But, when 10–74% phospholipid fraction is used, experimental problems arise. With lipophilic sample molecules, the use of concentrated phospholipid artificial membranes leads to two undesirable effects: (a) excessive membrane retention (90–100%) and (b) highly diminished permeability (extinguished in some cases), both effects presumably due to highly-increased drug-membrane binding, by participation in hydrogen bonding (HB) and/or ionic equilibrium (IE) reactions.

Hydrogen bonding between the sample molecules and the phospholipid bilayer membranes is thought to play an important role in the transport of such molecules. When 0–2% wt/vol phospholipid in alkane is used in the artificial membrane, the effect of hydrogen bonding is thought to be underestimated.

These adverse effects are considerably diminished by using certain surfactants, such as sodium laurel sulfate, bile acids, or cyclodextrins, to create a strong sink condition in the acceptor compartment of the permeation cell, the principal focus of our invention. The sink-forming reagents in this invention have low UV absorption for wavelengths above 230 nm. (The use of serum proteins is not feasible due to their very strong UV absorption over a wide range of wavelengths.)

Additional improvements are achieved using pH gradients between the donor and acceptor compartments of the permeation cell. A three-chamber diffusion differential equation, taking into account acceptor sink (and non-sink) conditions, and any pH gradients between the donor and acceptor solutions, was used. The new permeability equation takes into account membrane retention of the drug molecule, which clearly still exists (albeit lessened) in spite of the sink condition created.

In this invention, all concentrations of sample are determined by UV spectrophotometry using the area-under-the-curve (AUC) weighted regression procedure, with weighting scheme based on peak shape anomalies, as described for high-throughput measurement of solubility by Avdeef and Tsinman. [Avdeef, A., Tsinman, K. L., U.S. Patent Application Publication No. US 2002/0004244 A1, Jan. 10, 2002; Provisional Application No. 60/178,616, filed Jan. 28, 2000]

If the ionization constant of the molecule, $pK_a$, is known, either measured by standard instrumentation [Sirius Analytical Instruments Ltd., UK] or calculated by reliable procedures, [Advanced Chemistry Development Laboratories, Canada] then the effective permeability value, $P_e$, may be corrected for the effect of the unstirred water layer (UWL), to estimate the true membrane permeability value, $P_m$. This may be done by evaluating the pH dependence of $P_e$ coefficients, taken from the measurement of $P_e$ coefficients in solutions of different pH values, in the vicinity of the $pK_a$, as described by Walter and Gutknecht. [Walter, A., Gutknecht, J., J. Molec. Biol. 1984, 77, 255–264]

Alternatively, the unstirred water layer permeability may be measured more directly, using the methanol-treated filter method described by Avdeef and Tsinman, [e.g., FIG. 4.5 in Avdeef, A., Tsinman, K., U.S. Provisional Patent Application No. 60/178,616, Jan. 28, 2000] and others. This alternative method is not expected to be sufficiently accurate for correcting UWL effects of very lipophilic molecules, compared to the Walter-Gutknecht method.

The improvements in the PAMPA model arising from said invention were validated with an improved passive-diffusion GIT absorption model. Furthermore, a BBB absorption model is proposed, by combining the GIT absorption model with the prior art PAMPA practice of placing solubilizers, such as surfactants, bile salts, and water-soluble liphophilic polymers, into the donor compartment to overcome problems of low aqueous solubility of sample molecules.

In this invention, emphasis is placed on pharmaceutical applications using phospholipid-based membranes, but it is to be understood that broader applications are possible, such as in the agrochemical field, and in general chemical applications related to permeability assessment, where barriers may be constructed with various membrane-forming materials, including cultured cells.

BRIEF DESCRIPTION OF THE FIGURES

FIG. 15(a) contains Table 1 showing Pharmacokinetic and Physicochemical Properties of Selected Probe Drugs.

FIG. 15(b) contains Table 2 showing Neutral Lipid PAMPA Models, pH 7.4.

FIG. 15(c) contains Table 3 showing Egg Lecithin 10% wt/vol in Dodecane PAMPA Models, pH 7.4.

FIG. 15(d) contains Table 4 showing Soy Lecithin in Dodecane PAMPA Models (no SINK), pH 7.4.

FIG. 15(e) contains Table 5a showing Soy Lecithin in Dodecane PAMPA Models (with SINK), pH 7.4.

FIG. 15(f) contains Table 5b showing Soy Lecithin in Dodecane PAMPA Models (with SINK), pH 7.4.

FIG. 15(g) contains Table 6 showing Permeability ($10^{-6}$ cm/s units) and Retention in 20% wt/vol Soy Lecithin, at Iso-pH 5.0, 6.5, 7.4 with SINK in Acceptor Wells.

FIG. 15(h) contains Table 7 showing Intrinsic Permeabilities & the Unstirred Water Layer Permeabilities Determined from Gradient-pH Dependence of Effective Permeabilities: 20% Soy Lecithin in Dodecane, SINK in Acceptor.

FIG. 15(i) contains Table 8 showing Interpolated Effective and Membrane Permeability Determined from Double-Sink Conditions: 20% Soy Lecithin in n-Dodecane.

FIG. 15(j) contains Table 9 showing Effect of 100 mM β-Cyclodextrin in Acceptor Wells in the 20% wt/vol Soy Lecithin System, pH 7.4.

FIG. 15(k) contains Table 10 showing Effect of 100 mM β-Cyclodextrin in Donor and Acceptor Wells in the 20% Soy Lecithin System, pH 7.4.

FIG. 15(l) contains Table 11 showing Correlation ($r^2$) between Human Jejunal and PAMPA Permeabilities.

DETAILED DESCRIPTION OF THE INVENTION

Hardware Components of the Analytical Device of the Invention

Figure 1A:
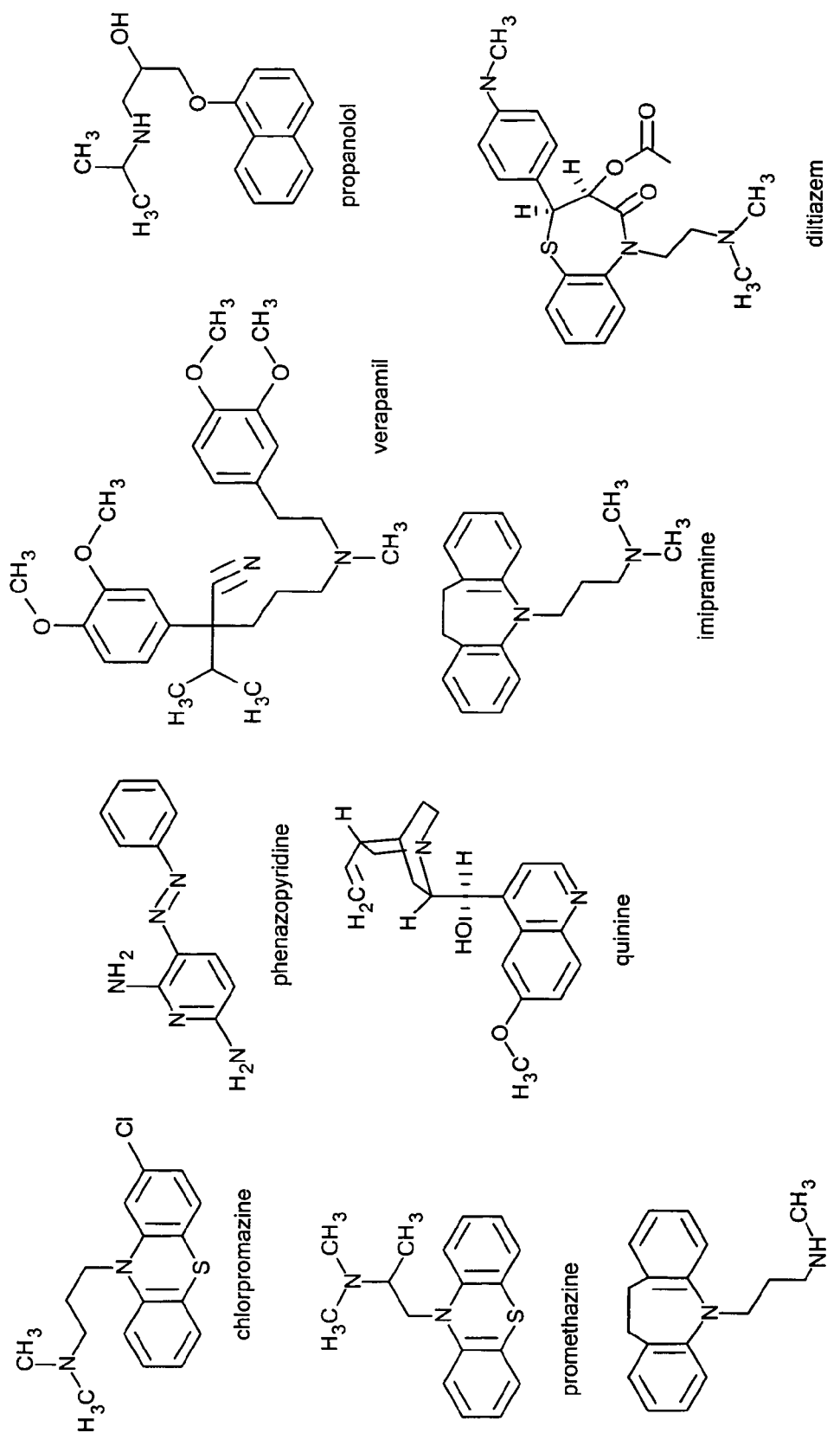
FIGS. 1(a)–(d) show the structures of compounds evaluated using the invention and for which data appear herein.
Figure 1B:
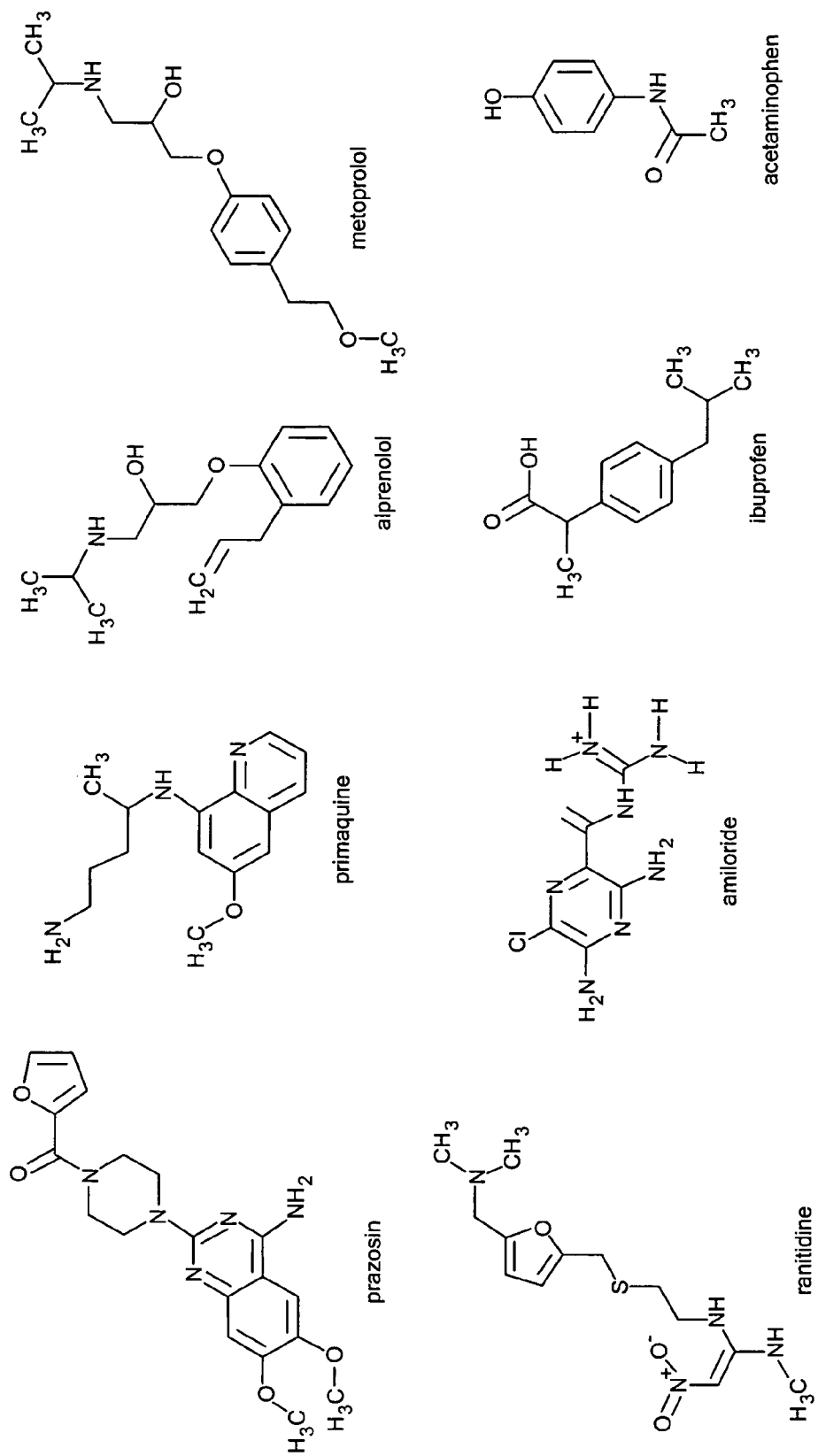
Figure 1C:
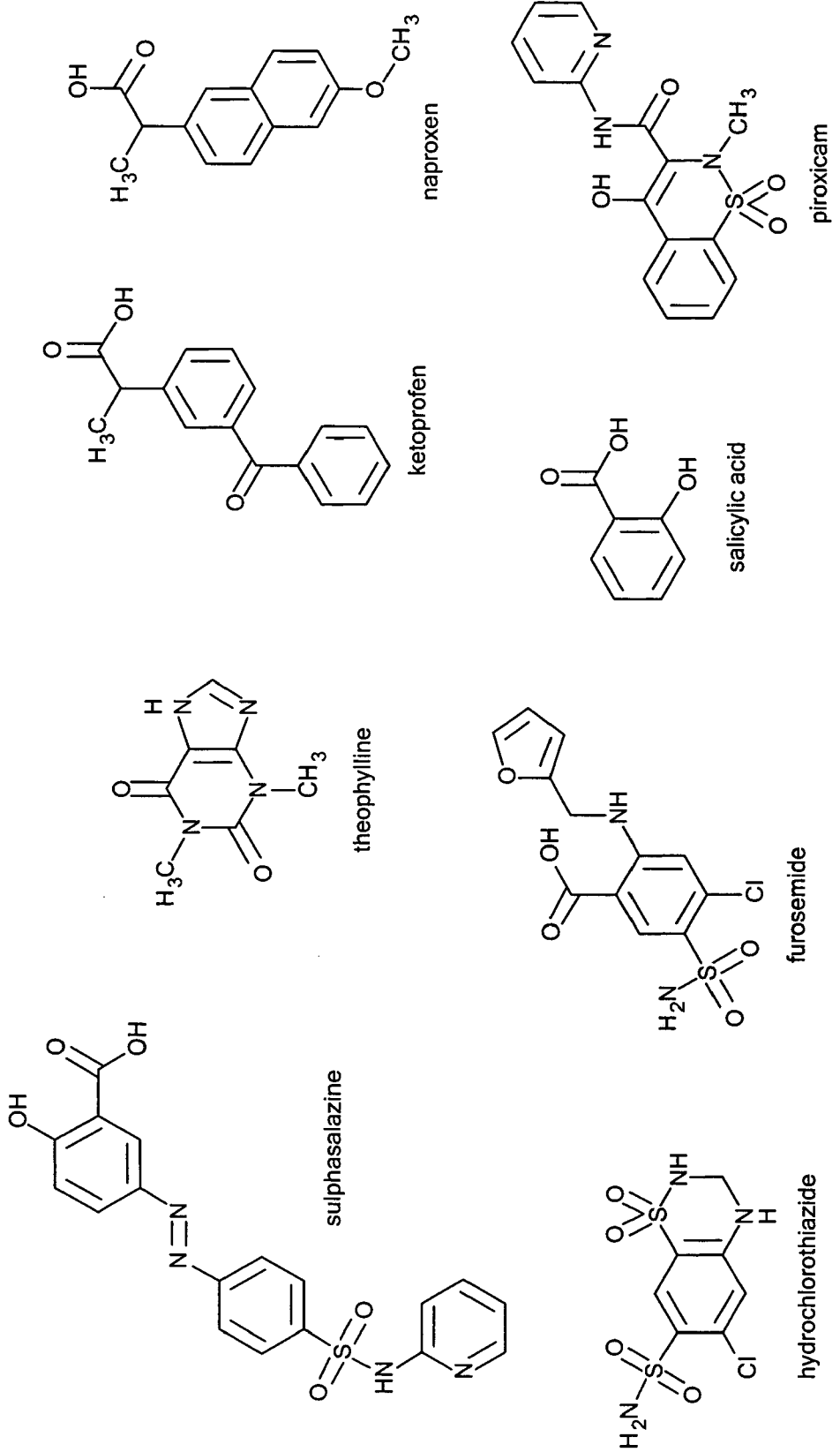
Figure 1D:
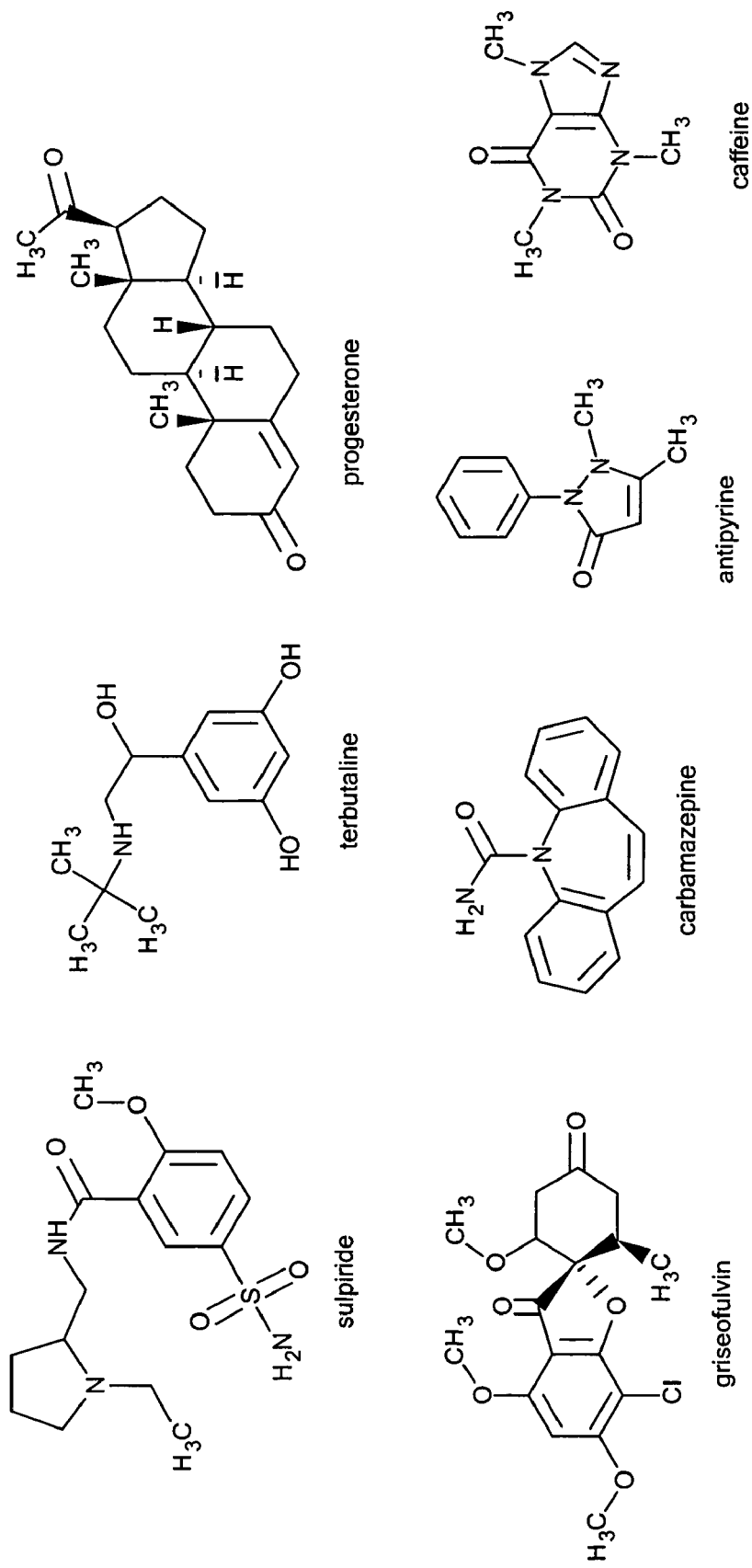
Figure 2:
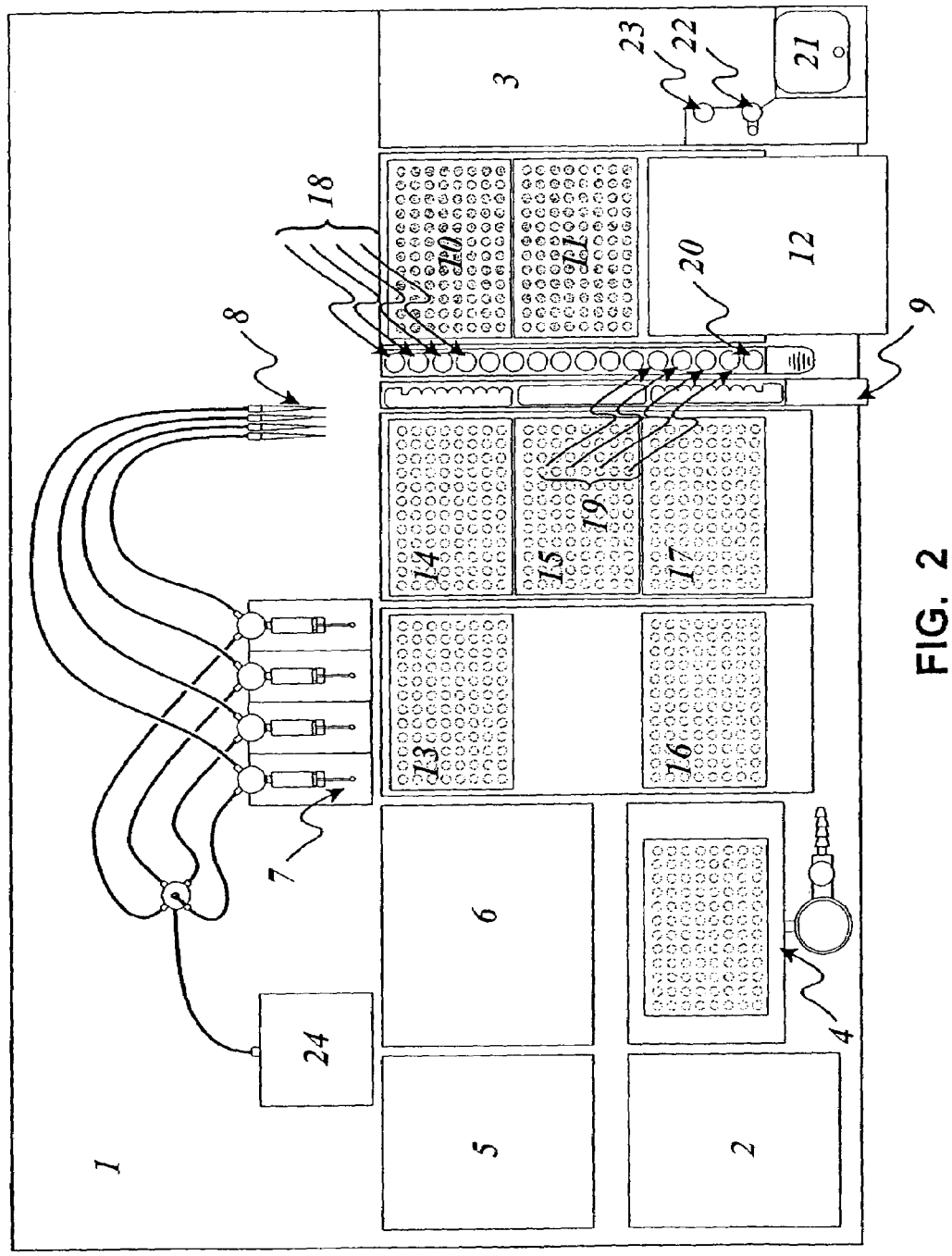
FIG. 2 represents a schematic of an analytical device utilized to carry out the methods described in this patent.

The analytical device, shown in a block diagram in FIG. 2, consists of a robotic liquid handling system (1), a microtitre plate scanning UV spectrophotometer (2), a pH titrator device (3), a microtitre plate vacuum filtration manifold (4), a microtitre plate washer (5), a microtitre plate orbital shaker (6), four (or eight) precision 0.5 mL syringe dispensers (7), four (or eight) dispenser arms (8) positioned by the robot anywhere on the worktable of the liquid handling system, a wash station and waste trough (9), two rack holders for 200 µL pipet tips (10 and 11), a used-tip collector (12), a stock sample microtitre plate (13), a plastic UV microtitre plate (14), a deep-well microtitre plate for reference aqueous solutions (15), acceptor hydrophobic-filter microtitre plate position (16), donor microtitre plate or sandwich position (17), four test tubes filled with acceptor sink solution (18), a test tube for 0.5 M NaOH (or KOH) titrant (19), a phospholipid holder tube (20), an electrode wash station (21), a titration vessel, with a magnetic stir bar and a magnetic stir motor underneath (22), and a test tube for storing the pH electrode (23). 24 is a universal buffer solution.

The robotic liquid handling system (1), is available commercially (e.g., Genesis RSP 100/4 System from Tecan, Research Triangle Park, N.C., USA)

The 96-well microtitre plate scanning spectrophotometer (2) takes data in the wavelength range 230 to 500 nm (at least), with 4 nm (or better) resolution (e.g., SpectraMAX 190 from Molecular Devices, Sunnyvale, Calif., USA).

Although our preferred detector system is a scanning microtitre plate UV spectrophotometer, diode-array microtitre plate UV spectrophotometers, and flow-through UV detector systems, scanning or diode array, may also be used.

Although a UV detector is the preferred embodiment of the invention, the detector may be any suitable spectrophotometric analytical detector, such as ultraviolet or visible spectrophotometer, a fluorimeter, a colorimeter, polarimeter, optical rotation or circular dichroism detector.

A pH titrator (3) is used, having a vessel to hold the solution being titrated (22), equipped with a pH meter capable of precisely reading pH from 1.5 to 12.5, having a dispenser (7) able to add 0.5 M NaOH titrant in precise small amounts, such as 1 μL, and able to stir the solution during titrant additions (e.g., pSOL Model 3 from pION, Woburn, Mass., USA).

A vacuum filtration manifold (e.g., from pION) for microtitre plates (4) is used, with a source of vacuum.

A microtitre plate washer (5) is used, with a 75% v/v methanol wash solution (e.g., from Tecan).

A microtitre plate orbital shaker is used (6) (e.g., from Lab-Line Instruments, Inc.).

Also used are commercially-sourced 96-well polyethylene or polypropylene microtitre plates, in 0.4, 0.5, and 2.2 mL well capacities (numerous sources), and commercially-sourced plastic UV microtitre plates (e.g., from Corning-Costar or Greiner).

In the basic protocols described below, 8 compounds are sampled in each microtitre plate, at 12 different pH-buffer solutions. This reflects the 8-row×12-column layout of the microtitre plates. The procedures can be easily scaled up three-fold to 24 samples per day on the present robotic system, still preserving the 12-pH profile, or to 384 samples per day at one pH.

Permeation Cell

Figure 3:
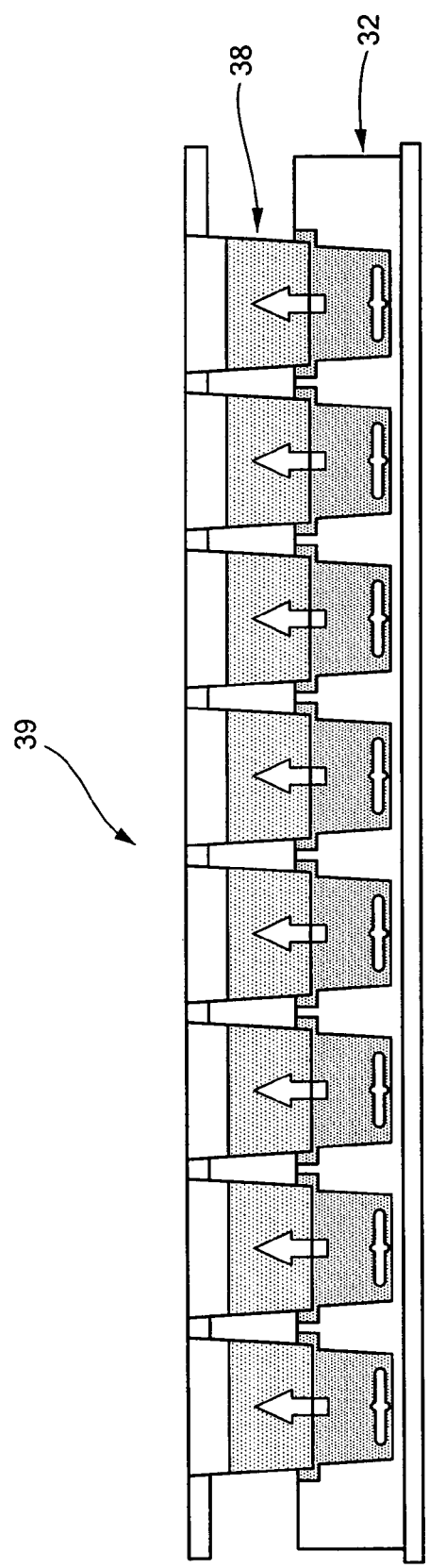
FIG. 3 shows a cross section of a 96-well microtitre plate PAMPA sandwich.

FIG. 3 shows a cross-sectional end-view of the 96-well PAMPA sandwich microtitre plate assembly (39) that was used, and usually placed in position 17 of the robotic worktable (1). Each of the 96-wells represents a permeation cell consisting of two chambers, separated by a thin membrane. At the start (time, t=0 sec), the sample is placed into the donor (D) well (of the lower 96-well microtitre plate, 32), typically containing 0.2 cm³ ($V_D$) of a universal buffer solution (24), typically adjusted to $pH_D$ 5.0, 6.5, or 7.4. The initial donor sample concentration is represented as $C_D(0)$, in units of mol/cm³, at time, t=0. A hydrophobic-filter microtitre plate, 38 (Millipore Immobilon-P IPVH: 125 μm thick, 0.45 μm pores, 70% porosity, area A=0.3 cm²), is placed over the donor microtitre plate, 32. The filter forms the bottom of an acceptor well in a 96-well hydrophobic-filter microtitre plate (38). A 4 μL ($V_M$) quantity of a dodecane solution of a phospholipid (1 to 75% wt/vol) is deposited on the microfilter using the robotic dispenser tips (8). Then typically 0.2 cm³ ($V_A$) of the acceptor sink buffer (37) (or the universal buffer (24)) is placed into the (top) acceptor well, generally at $pH_A$ 7.4. The initial acceptor sample concentration, $C_A(0)$, is zero. After a time t (typically 3–15 h), the permeation experiment is stopped. The final acceptor and donor concentrations, $C_A(t)$ and $C_D(t)$, respectively, are determined by UV spectrophotomtry. To effect an artificial acceptor sink condition, 1% wt/vol sodium laurel sulfate is added to the acceptor compartment.

Software

A computer program is used, which controls the actions of the robotic fluidic delivery system, prompts the operator to perform certain tasks, controls the actions of the spectrophotometer, and processes the spectral data to determine concentrations as a function of pH from which the permeability and membrane retention are calculated, displays the data graphically and in report forms, and which transfers the results of the analyses to a Microsoft® Excel spreadsheet. Such a computer program is commercially available from pION.

The software is installed on a Windows NT® (or later verson operating system) computer, which electronically communicates with the robotic workstation (1), the UV spectrophotometer (2), and the pH titration device (3), by available means (RS232 serial cable, infrared, or radio wave), and controls the actions of the analytical device and stores the spectra collected for further processing.

The Gradient-pH Permeability Equation Used in the Invention

For purposes of the invention herein, permeability is defined as follows:

$$P_e^{(D)} = -\frac{2.303 V_D}{A(t-\tau_{SS})}\left(\frac{1}{1+r_a}\right)\log_{10}\left[-r_a + \left(\frac{1+r_a}{1-R}\right)\frac{C_D(t)}{C_D(0)}\right] \quad (2)$$

where $r_a = (V_D/V_A)(P_e^{(A)}/P_e^{(D)})$ and R is the membrane retention, here defined as $$R = 1 - [C_D(t) + C_A(t) \cdot V_A/V_D]/C_D(0) \quad (3)$$

The supercript (D) denotes permeability in the direction donor-to-acceptor, and the superscript (A) denotes permeability in the opposite direction. With ionizable test compounds and with solutions of different pH on the two sides of the membrane, $P_e(A)$ and $P_e(D)$ are generally different. All other terms in eqs. (2) and (3) have been defined following eq. (1). If the initial donor solution has precipitate and is filtered, it is not possible to know the absolute concentrations in the initial donor solution, $C_D(0)$, but the relative concentrations, $C_D(t)/C_D(0)$ and $C_A(t)/C_D(0)$, are determined correctly, by the procedure described in the next section.

When the pH values are the same in the two chambers of the permeation cell, $r_a = V_D/V_A$, and eq. (2) becomes equivalent to eq. (1). Implicitly, eq. (2) has two unknowns: $P_e^{(A)}$ and $P_e^{(D)}$, and thus it is necessary to assay at least two separate wells for each compound, with one well containing the same pH 7.4 on the donor and acceptor sides: $P_e^{(A)} = P_e^{(D)} = P_e$. This iso-pH case can be solved directly, using eq. (1), and the value of $P_e^{(A)}$ at pH 7.4 then substituted into eq. (2) to solve for $P_e^{(D)}$ in the other gradient-pH wells, at pH 5 or 6.5, for example.

With iso-pH conditions ($pH_D = pH_A$), the concentration of the sample in the acceptor wells cannot exceed that in the donor wells. With gradient-pH conditions ($pH_D \neq pH_A$), this limitation is lifted. At very long times, the concentrations in the donor and acceptor chambers reach equilibrium values, depending on the pH gradient: $C_D(\infty)/C_A(\infty) = P_e^{(A)}/P_e^{(D)}$. In some PAMPA gradient-pH assays, it is not uncommon to have most of the sample move to the acceptor side, due to the gradient-pH sink conditions created. Shorter permeation times are needed to overcome this, a welcome prospect in high-throughput applications.

If surfactant is added to the acceptor wells under iso-pH conditions (pH$_D$=pH$_A$), then in general, permeability coefficients in the donor-to-acceptor (D) and the acceptor-to-donor (A) directions are not the same: $P_e^{(A)*} < P_e^{(D)}$, with asterisk denoting presence of surfactant in acceptor wells. The extent to which the surfactant in the acceptor wells depresses the reverse-direction permeability, $P_e^{(A)*}$, may be estimated by performing a second iso-pH 7.4 assay with the surfactant added to the donor wells. The $P_e^{(D)*}$ values may be calculated with eq. (1). From the two measurements, the asymmetry ratio, $P_e^{(D)*}/P_e^{(D)}$, can be as low as $10^{-4}$ for lipophilic bases at pH 7.4. Keeping this attenuation of the reverse transport in mind, when both acceptor surfactant and gradient-pH conditions are used, then eq. (2) is solved with the approximation that $r_a=0$.

Area-Under-the-Curve (AUC) Determined by Weighted Regression Method

The method utilized by the analytical device for determining concentrations of species by UV spectrophotometry is based on a weighted regression analysis of whole spectra, where area-under-the-curve (AUC) assessment is made. [Avdeef, A., Tsinman, K. L., U.S. Patent Application Publication No. US 2002/0004244 A1, Jan. 10, 2002; Provisional Application No. 60/178,616, filed Jan. 28, 2000] All of the 65 to 130 measured absorbance values from each well in the microtitre plate are used in the analysis. The object of the analysis is to assess the unknown concentration of the sample in the final donor and final acceptor solutions, at the end of the permeation time, t, as a fraction of the initial donor sample concentration, $C_D(0)$, by applying Beer's law. The technique is unique in how it assigns weights to the individual absorbance data, to make the assessment of concentrations more reliable, especially when samples are not entirely pure. Anomalies, recognized as extraneous peaks, due to dust, air bubbles, or impurities are corrected automatically. Absorbance (the dependent variable) and wavelength (the independent variable) are both assumed to be subject to experimental error. The weighting scheme used in the analysis is constructed from the variance $\sigma^2(a)=\sigma_c^2+(\sigma_\lambda da/d\lambda)^2$, where a is the absorbance and $\lambda$ is the wavelength. In the software of the analytical device, $\sigma_c=0.0002$ (optical density units), the fixed contribution to the variance in the measured absorbance (experimentally determined by replicate baseline measurements, usually from the high-end domain 450–500 nm), and $\sigma_\lambda=0.2$ nm (estimated error in wavelength, specified by the UV spectrophotometer manufacturer). The weighting scheme properly recognizes that measurements of absorbance on the steep sides of peaks are not as reliable as those near the peak top or from the baseline portions.

Reagents and Sample Solutions

The following reagents are used in the assay method. Details regarding the method can be found in the next section (Implementation of the Improved PAMPA Method) and in FIG. 4.

A universal buffer system solution (24) is used, designed to have a linear response to alkali titrant additions in the pH range 3 to 10, with nonlinearity in pH of about ±0.05 pH units. [Avdeef, A., Tsinman, K. L., U.S. Patent Application Publication No. US 2002/0004244 A1, Jan. 10, 2002; Provisional Application No. 60/178,616, filed Jan. 28, 2000] The solution possesses buffer components with low-UV absorption (each component with OD<0.05 at 220 nm for a 4.5 mm path length). The solution possesses buffer components with low tendency to interact with sample species, and specifically excludes phosphate, citrate, and boric acid. A 2-L solution of the buffer, the pH of which is initially near 3, has the capacity of about 100 mL of 0.5 M NaOH when raising pH to 10. The ionic strength of the universal buffer solution is about 0.01 M. Such a universal buffer solution is specifically designed for solubility and permeability measurements by UV spectrophotometry and is commercially available from pION.

The acceptor sink buffer (37) preferentially used in the invention is a 20 mM HEPES buffer solution, adjusted to pH 7.4 with NaOH, containing 1% wt/vol sodium laurel sulfate (35 mM). Also, the universal buffer solution (24), adjusted to pH 7.4 with NaOH, containing 1% wt/vol sodium laurel sulfate may be used. Both of the buffer solutions may have the sodium laurel solution substituted with 100 mM β-cyclodextrin or other cyclodextrins, or 10 mM sodium glycocholate or other bile salts, and at other concentrations sufficient to significantly lower the unbound drug fraction in the acceptor solution.

It is clear to those practiced in the art that other acceptor sink buffer solutions may be made, either using other pH buffers, or using other sink-forming additives, such as hydroxypropyl methylcellulose (HPMC), or sodium salts of poly(4-styrenesulfonic acid), poly(methacrylic acid), carboxy methylcellulose (CMC), and poly(acrylic acid). Such additives are selected to have (a) high capacity to bind sample molecules, (b) sufficiently low UV absorption, (c) adequate solubility in water, and (d) low vapor pressure. Solutions containing serum proteins would not be suitable in this invention, due to excessively high molar absorptivities in UV spectra.

The donor sink buffer solution (33) used in the invention may be prepared in the same way as the acceptor sink buffer solution (37), and need not be identical to the acceptor solution in the assay.

A standardized 0.5 M NaOH solution (26) is used, containing <0.5% M/M carbonate (available from a number of commercial sources).

Lipid solutions (34) were prepared using Avanti's '20% lecithin soy lipid extract,' by dissolving the appropriate weighed amounts in n-dodecane containing 1.5% absolute ethanol. The lecithin consists of 24% PC, 18% PE, and 12% PI, according to the manufacturer. Specifically, 10 to 74% wt/vol soy lecithin solutions were tested. Lower concentrations may be used. The preferred composition, 20% wt/vol soybean lecithin dodecane solution, is available commercially from pION. Normal hexadecane may be used in place of n-dodecane. To those versed in the art, it should be apparent that suitable solvents for the lecithin are (a) simple normal alkanes, $CH_3(CH_2)_nCH_3$, with n=8 to 16, (b) simple normal dienes, $CH_2=CH(CH_2)_nCH=CH_2$, with n=4 to 8, (c) simple normal alkenes, $CH_2=CH(CH_2)_nCH_3$, with n=5 to 13, (d) squalene, (e) octanol, and (f) olive oil. (Example 2 addresses the use of solvents (e) and (f) above.)

Sample solutions of the test compounds (28) were prepared most often as 10 mM DMSO solutions, which were stored frozen in a refrigerator between use.

Implementation of the Improved PAMPA Method

Figure 4:
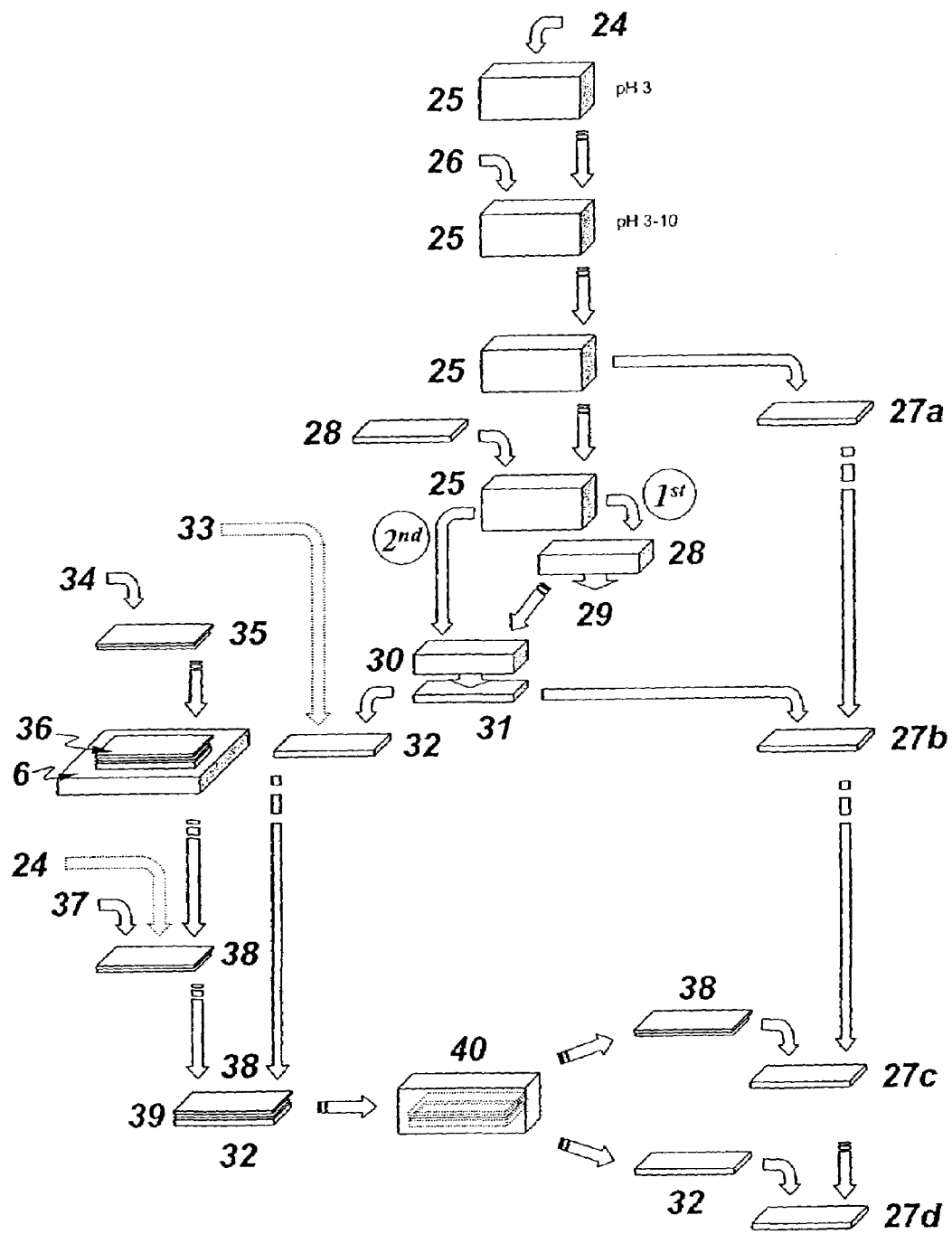
FIG. 4 is a schematic showing PAMPA method implementation.

FIG. 4 is a general flow diagram of the preferred method. A universal buffer solution (24), initially at pH 3, is added to a 96-deep-well microtitre plate (25). A standardized sodium hydroxide solution (26) is added to each well to adjust the pH of the universal buffer solutions to the desired values in the interval pH 3 to 10. A portion of the pHadjusted buffer solutions in 25 is transferred to plastic UV microtitre plate 27a (low-absorbing plastic for UV measurements, from Greiner or Corning Costar) and the optical density of the solutions is read on the spectrophotometer (2). This constitutes the UV-characterized "donor-blank" solution. An aliquot of the sample from the stock microtitre plate (28) is transferred into 25. A portion of the sample buffer solutions in 25 is filtered through a hydrophilic PVDF filter (28), with the filtrate 29 discarded. This serves to create a sample "pre-coated" hydrophilic-filter microtitre plate. A second portion from 25 is filtered through 30 and collected in 31. A portion of the filtered solutions in 31 is transferred to plastic UV microtitre plate (27b) (which may be the rinsed microtitre plate 27a) and the optical density of the solutions is read on the spectrophotometer (2). This constitutes the UV-characterized "reference" solution. Another portion of the filtered solution in 31 is added to the PAMPA donor microtitre plate (32). Optionally, a donor solution additive (33) may be placed into 32, which is to become the bottom part of the PAMPA sandwich. The PAMPA lipid solution (34) is painted onto the filters of an acceptor hydrophobic filter microtitre plate (35), to produce the membrane model (36). The hydrophobic-filter microtitre plate 36 is then vigorously agitated on an orbital shaker (6) to allow the lipid to uniformly spread throughout the microchannels of the filter. Afterwards, the acceptor sink buffer (37) is added to the wells of 36, to produce the initial acceptor solution of the PAMPA sandwich, 38 (cf. FIG. 3). Alternatively, for non-sink analysis, the universal buffer solution (24) may be added at this point. The sandwich (39) is assembled from 32 and 38 (FIG. 3), and placed into an environmental chamber (40) for about 4 h, to protect the solutions from evaporation, ambient carbon dioxide, and molecular oxygen. After the permeation time, the sandwich is separated. A portion of the acceptor solutions in 38 is transferred to plastic UV microtitre plate (27c) (which may be the rinsed microtitre plate 27b) and the optical density of the solutions is read on the spectrophotometer (2). This constitutes the UV-characterized "final acceptor" solution. A portion of the donor solutions in 32 is transferred to plastic UV microtitre plate (27d) (which may be the rinsed microtitre plate 27c) and the optical density of the solutions is read on the spectrophotometer (2). This constitutes the UV-characterized "final donor" solution.

We have selected 32 unrelated molecules, whose structures are shown in FIGS. 1(a)–(d), to illustrate the properties of the improved PAMPA method. Table 1 (see FIGS. 15(a)–(l) containing Tables 1-11, respectively) summarizes the key pharmacokinetic and physicochemical properties of the selected probe molecules, consisting of bases, acids, and neutral species. The lipid models are assigned a two-part serial number (e.g., 10.1): the first index is simply a serial designation (see first column in Table 11) and the second index indicates whether an anionic surfactant artificial sink condition is in effect in the assay (0=no, 1=yes). Special cases (such as cyclodextrin, bile salt, or mixed-micelle assays) will employ other values of the second index.

All of the following examples reflect improvement in measuring permeability vs. prior methods. The improvements are indicated by (a) shorter permeation time (1–4 h vs. the Kansy orginal 15 h), (b) improved accuracy in measurement of permeability and membrane retention, due to improvements in the UV spectrophotometric measurement (Example 8), (c) better prediction of the human jejunal permeability, using the 'double-sink' model (Example 11), and (d) better prediction of human intestinal absorption, using the 'sum-permeability double-sink' model (Example 12). These examples are intended to illustrate the invention and not to limit it.

EXAMPLE 1

Apparatus of FIGS. 2–4: Effective Permeability and Membrane Retention Determined by the Improved PAMPA Method, using Acceptor Sink and Gradient-pH Conditions FIG. 2 summarizes the apparatus detailed below, with FIG. 3 showing the permeation cell (39) used. The general PAMPA method used to determine permeability is described in FIG. 4, and a specific embodiment is detailed below.

Data Collection

1. The universal buffer solution at pH 3 (24) is purged with a stream of dispersed helium gas for about 30 min prior to the assay. The robotic fluidic system (7,8,24) is then flushed to dislodge any trapped air bubbles in the lines.

2. The analytical device places 2.5 mL of universal buffer solution (24), initially at pH 3, into the side arm tube of a tall test tube (22) ("J-tube") located in the pH titrator assembly (3). An alkalimetric pH titration is performed, using standardized 0.5 M NaOH as titrant.

3. Analysis of the titration data produces the pH values corresponding the titrant volumes, e.g., 8, 16, 23, 30, 37, 44, 52, 59, 65, 73, 81 µL; these correspond closely to pH settings 3.0 through 8.5, in increments of 0.5 pH units. These volumes will be used by the device below.

4. The 96-well stock microtitre plate, containing 10 mM sample solutions in DMSO (28), is placed in position 13, furthest from operator on left rack on the robot table. Only one column of 8 sample wells will be used in this particular assay; for example, wells A1, B1, . . . , H1 (or A2, B2, . . . , H2, etc.) will contain the required compounds, 10 mM in DMSO in this example. For purposes of UV blank corrections, one of the wells only contains DMSO, free of sample.

5. A new 96-well deep microtitre plate (25) (2.2 mL wells) is placed at position 15, middle of the rack on the right on robot table.

6. A new 96-well Greiner (or Costar) plastic UV microtitre plate (27) is rinsed on the microtitre plate washer (5), and placed in position 14, and covered with a plastic lid, to prevent dust from getting into the microtitre plate.

7. New racks of 200-µL disposable (nonconductive, clear plastic) pipet tips are placed in positions 10 and 11 on the robot worktable.

8. A plastic waste bag is attached to the bottom of the waste slide for the used tips (12).

9. The system solution bottle needs to contain at least 400 mL of the universal buffer solution (24).

10. Four clean test tubes in positions 19 are each filled with 4 mL freshly prepared, low-carbonate, 0.5 M NaOH (26).

11. Four clean test tubes, each containing 6 mL acceptor sink solution (37) at pH 7.4, are placed into positions 18.

12. An ampule of phospholipid solution, having been allowed to warm up to room temperature, is opened by snapping the glass neck, and the lipid (34) is transferred into a clean plastic tube placed in position 20.

13. The robot loads 1000 µL universal buffer solution (24) into each well of the deep 96-well microtitre plate 25 in position 15. Then the robot draws 0.5 M NaOH from test tubes in positions 19 of the test tube rack. The robot proceeds to deposit, e.g., 8 µL into the 8 deep wells A2–H2, 16 µL into deep wells A3–H3, 23 µL into deep wells A4–H4, 30 µL into deep wells A5–H5, 37 µL into deep wells A6–H6, 44 µL into deep wells A7–H7, 52 µL into deep wells A8–H8, 59 µL into deep wells A9–H9, 65 µL into deep wells A10–H10, 73 µL into deep wells A11–H11, and 81 µL into deep wells A12–H12.

14. The robot loads an additional 1000 µL universal buffer solution (24) into each of the deep wells, followed by extensive mixing.

15. Before any sample is added to 25 in position 15, the robot transfers 150 µL buffer solutions from the deep well to the UV microtitre plate 27a in position 14 on the table (with protective cover lid removed). The operator is prompted to take UV spectra of the buffer-filled UV microtitre plate, using the spectrophotometer (2). This corresponds to the UV "donor blank" reading. Afterwards, the UV microtitre plate is rinsed with a methanol-water solution using the microtitre plate washer (5) and returned as 27b to position 14, covered with a lid to keep dust out.

16. To each of the deep wells of 25 in position 15 (containing, e.g., 1850–1931 µL pH buffer), 10 µL sample (28) is added, using the 200 µL tips 13. The first sample pickup is discarded back into the stock microtitre plate, to ensure that the tip does not have an air gap at the opening and to ensure the dispenser motor gears are free of slack, and that the inside surface of the tip is wetted before subsequent sample pickup. Vigorous "regurgitative" mixing follows in the deep wells of 25. The sample stock microtitre plate 28 in position 13 may now be removed, protectively sealed, and stored in a refrigerator. To one of the rows in the deep-well microtitre plate (25), 10 µL of pure DMSO is added, containing no sample. This buffer solution serves as a "acceptor-blank" solution in the calculation procedure.

17. The solutions in the deep-well microtitre plate 25 are filtered using the manifold 4. The operator places a used 96-well microtitre plate (0.5 mL wells) in the bottom of the vacuum manifold. On top of it the operator places a new 96-well polystyrene hydrophilic-filter microtitre plate (0.4 mL wells, PVDF hydrophilic, 0.2 µm pore). The operator assembles the vacuum manifold accordingly. The robot transfers 100 µL sample solutions prepared in the deep-well microtitre plate for the filtration step: 15→>4. The operator is prompted to turn on the vacuum, to filter the solutions. This step pre-conditions the filters with sample, and is part of the so-called "double filtration" step. The operator then dis-assembles the manifold and replaces the bottom (used) microtitre plate with a clean empty 96-well microtitre plate (0.5 mL wells) in the bottom of the vacuum manifold 4. On top of it the operator returns the sample-preconditioned 96-well hydrophilic-filter microtitre plate (0.4 mL wells). The operator re-assembles the vacuum manifold. The robot transfers 400 µL sample solutions for the filtration step: 15→>4. The operators is prompted to turn on the vacuum, to filter the solutions, some of which may be turbid and may have precipitate in them. The operator discards the top hydrophilic-filter microtitre plate and exposes the bottom microtitre plate for robotic access.

18. The robot transfers 150 µL of the filtered reference solution to the UV microtitre plate 27b. The operator is prompted to take the reference UV spectra of the solutions in the UV microtitre plate, using 2. The UV microtitre plate is thoroughly washed on the microtitre plate washer 5 (using a 75% methanol-25% water solution) and as 27c placed in position 14, with a protective dust cover.

19. A clean donor microtitre plate (32) (available from pION) is placed in position 17. The robot transfers 200 µL of the reference solution in 31 to the donor microtitre plate 32.

20. A second (dummy) donor microtitre plate is placed in position 16, and a fresh hydrophobic-filter microtitre plate (Immobilon-P IPVH, available from Millipore) is placed on top of it. The robot loads the tips 8 with phospholipid (34) from tube 20, and paints the filters of 35 in position 16 with the phospholipid.

21. The empty donor microtitre plate with a lipid-painted hydrophobic-filter microtitre plate (36) on top is covered with a lid, taken to the orbital shaker 6, and shaken vigorously for 1 min, to ensure uniform deposition of the lipid in the pores of the microfilters.

22. The lipid-coated acceptor microtitre plate 36 with dummy donor microtitre plate is returned to position 16, with lid removed, and 150 µL of the the acceptor sink buffer (37) at pH 7.4 (18) is transferred into each of the 96 wells of the acceptor microtitre plate (36) in position 16.

23. The filled acceptor microtitre plate (38) in position 16 is placed on top of the donor microtitre plate (32) in position 17, to create the PAMPA sandwich (39), and covered with a lid. The dummy donor microtitre plate in position 16 is put aside.

24. The PAMPA sandwich (39) in position 17 is then transferred into an "environmental" box (40), which maintains a saturated humidity and contains an antioxidant chemical and a carbon dioxide scrubber (commercially available from several sources). The permeation time of 4 h is allowed to lapse.

25. After the permeation period elapses, the operator transfers the sandwich (39) back to position 17 and removes the cover.

26. The operator removes the cover on the UV microtitre plate 27c at position 14. The robot transfers 150 µL from the wells of the acceptor microtitre plate 38 to the UV microtitre plate 27c. The operator is prompted to take the acceptor UV spectra of the UV microtitre plate. Afterwards, the UV microtitre plate is thoroughly washed on the microtitre plate washer 5 (using a 75% methanol-25% water solution) and returned as 27d to position 14. The top hydrophobic-filter microtitre plate (38) of the sandwich (39) is discarded, giving access to the bottom donor microtitre plate (32) in position 17. The robot transfers 150 µL to the UV microtitre plate 27d. The operator is prompted to take the donor UV spectra of the UV microtitre plate. Afterwards, the UV and donor microtitre plates may be discarded.

Data Processing

Eq. (2) is used to evaluate the effective permeability, in the direction donor-to-acceptor. In the example when acceptor sink is present, the equation is solved with the approximation that $r_a=0$. Membrane retention is calculated using eq. (3). The wells containing the "acceptor-blank" solution are used to correct for the UV spectral contributions of DMSO, and are also the basis of a scheme to correct for the UV spectral contributions of the sink-forming constituents in the acceptor buffer.

EXAMPLE 2

Neutral Lipid Models at pH 7.4

Three pH 7.4 neutral lipid models are described: (a) 2% wt/vol DOPC in dodecane, (b) 100% octanol, and (c) 100% dodecane. Table 2 lists the effective permeability, $P_e$, standard deviation (SD) and membrane retention (% R) of the 32 test molecules (Table 1). The units of $P_e$ and SD are $10^{-6}$ cm $s^{-1}$.

The 2% DOPC in dodecane (Model 1.0, Table 2) was an early PAMPA model explored. [Avdeef, A., Strafford, M., Block, E., Balogh, M. P., Chambliss, W., Khan, I., Eur. J. Pharm. Sci. 2001, 14, 271–280] The lipid is commercially available in a highly-purified preparation (in flame-sealed glass ampules packed under nitrogen), and is most like that used in the original 1960s bilayer (black) lipid membrane (BLM) experiments. The lipid is completely charge neutral. It shows relatively low membrane retention for most molecules in Table 2, with the exception of chlorpromazine, phenazopyridine, primaquine, and progesterone.

A few molecules have unexpectedly low permeability in 2% DOPC, not consistent with their octanol-water partition coefficients. Notably, metoprolol has a $P_e$ value about ten times lower in 2% DOPC, compared to 10% egg lecithin. Also, the $P_e$ of prazosin appears to be significantly lower in DOPC, compared to other lipids.

Octanol permeability was important to explore (Model 2.0, Table 2), since it is the principal basis for the lipophilicity scale in pharmaceutical research. Octanol appears to enhance the permeability of hydrophilic molecules, compared to DOPC and dodecane. The mechanism is not precisely known, but it is reasonable to suspect that the large amount of water dissolved in octanol may provide a 'shuttle' action in PAMPA. This suggests a way for modeling biological aqueous pores, using phospholipids dissolved in octanol or olive oil, rather than simple alkanes, such as n-dodecane.

Membrane retention of lipophilic molecules is significantly increased in octanol, compared to 2% DOPC. Chlorpromazine and progesterone show R>90% in octanol. Phenazopyridine, verapamil, promethazine, and imipramine show R>70%.

Dodecane-coated filters were studied to demonstrate the role hydrogen-bonding and electrostatic effects play in the phospholipid-containing systems (Model 3.0, Table 2). For example, measuring the differences between $P_e$ deduced from 2% DOPC in dodecane and 0% DOPC in dodecane might indicate the extent of H-bonding and/or electrostatic interactions for specific probe molecules. Table 2 indicates that some molecules are retarded by the presence of DOPC (e.g., phenazopyridine, verapamil, metoprolol, theophylline, terbutaline, antipyrine), while most molecules are accelerated by DOPC (e.g., chlorpromazine, imipramine, diltiazem, prazosin, progesterone).

EXAMPLE 3

DOPC under Acceptor Sink Conditions

Figure 5A:
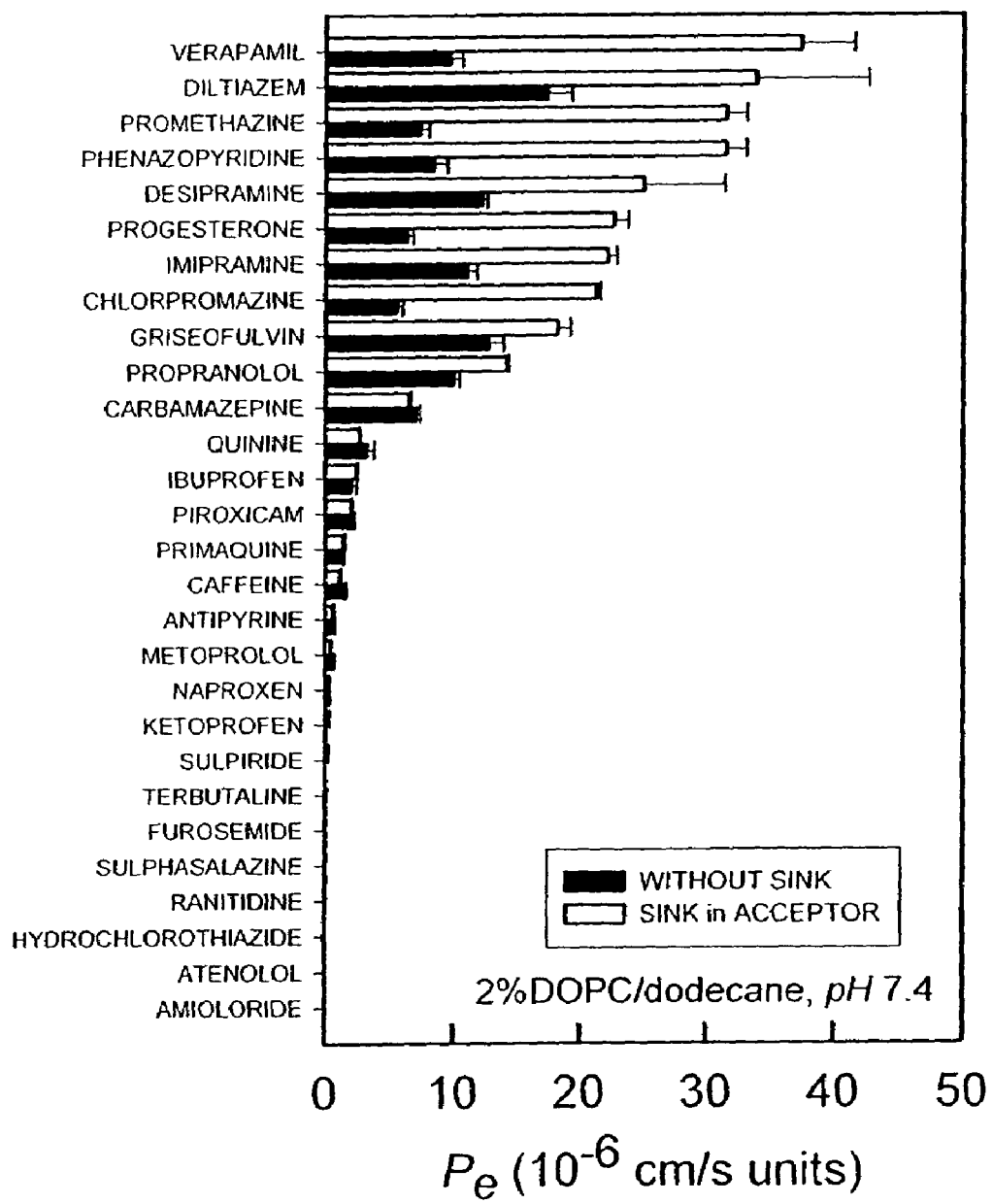
FIG. 5 illustrates the 2% DOPC model, pH 7.4: (a) effective permeability with (Model 1.1) and without (Model 1.0) surfactant-based acceptor sink; (b) membrane retention with (Model 1.1) and without (Model 1.0) acceptor sink.

FIG. 5(a) shows the effect of the sink condition on the effective permeability in the 2% DOPC system (Model 1.1). Just about all of the lipophilic bases showed a two- to three-fold increase in $P_e$. The simplest interpretation of this is that when lipophilic molecules reach the acceptor wells, they are bound to the surfactant, and the concentration of the unbound (membrane-permeating) form of the drug greatly diminishes. Hence, the reverse flux, based on the unbound portion of the concentration $C_A(t)$ is nil. Thus, half of the UWL resistance effectively disappears, leading to a doubling of $P_e$ for the diffusion-limited molecules. The topic of the UWL is discussed in greater detail elsewhere. [Avdeef, A., Curr. Topics Med. Chem. 2001, 1, 277–351] The binding of the positively-charged lipophilic molecules by the negatively-charged micelles formed by the surfactant is expected to have a strong ionic component, as well as a hydrophobic component.

Figure 5B:
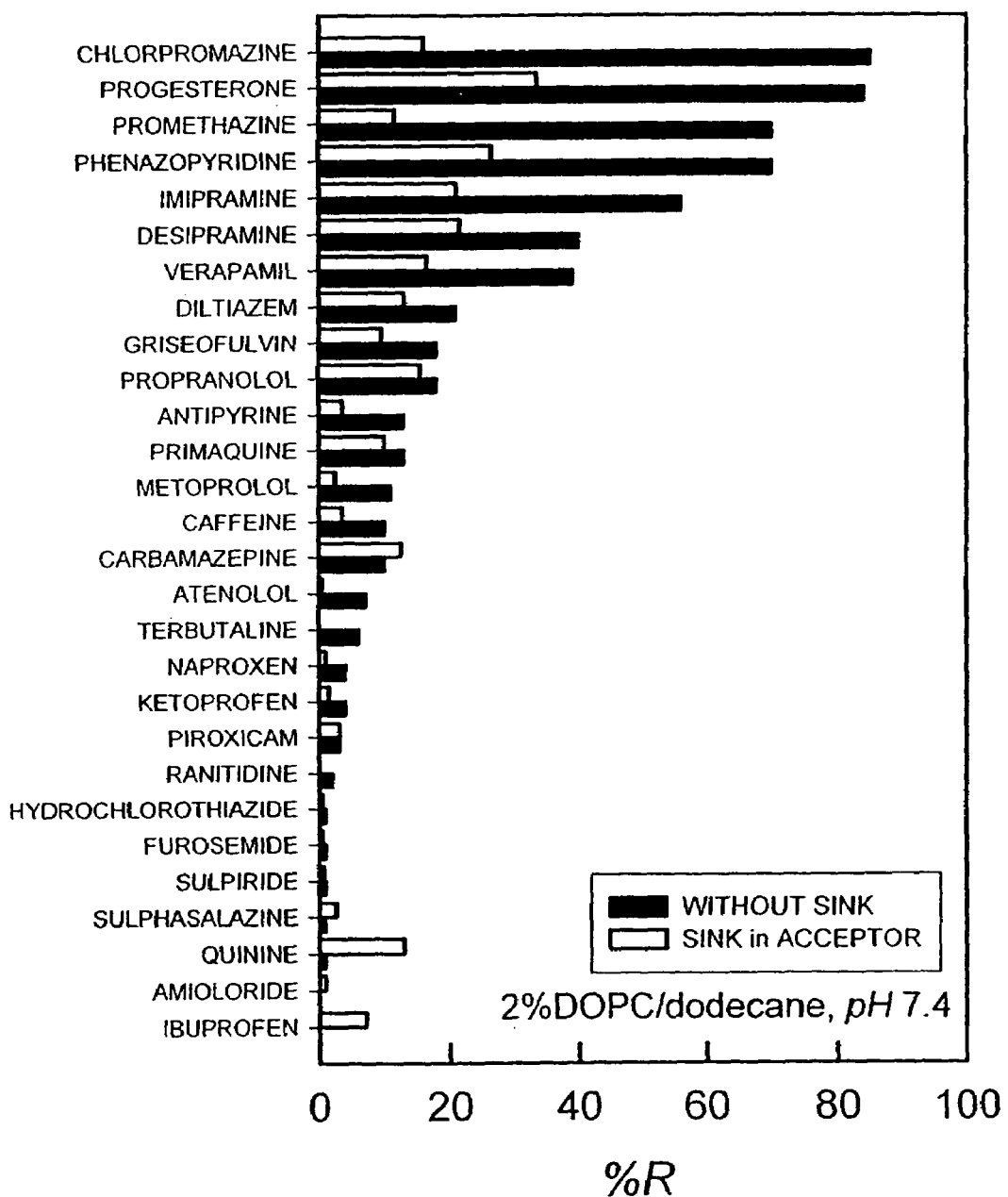

Furthermore, the membrane retention of the lipophilic test molecules are dramatically decreased in the presence of the sink condition in the acceptor wells, as shown in FIG. 5(b). All molecules show R<35%, with progesterone and phenazopyridine showing the highest values, 34% and 26%, respectively.

The combination of increased $P_e$ and decreased % R allowed the permeation time to be lowered to 4 h, in comparison to the originally specified time of 15 h by Kansy, a considerable improvement for high-throughput applications.

EXAMPLE 4

PAMPA Models Based on Egg Lecithin

Figure 6:
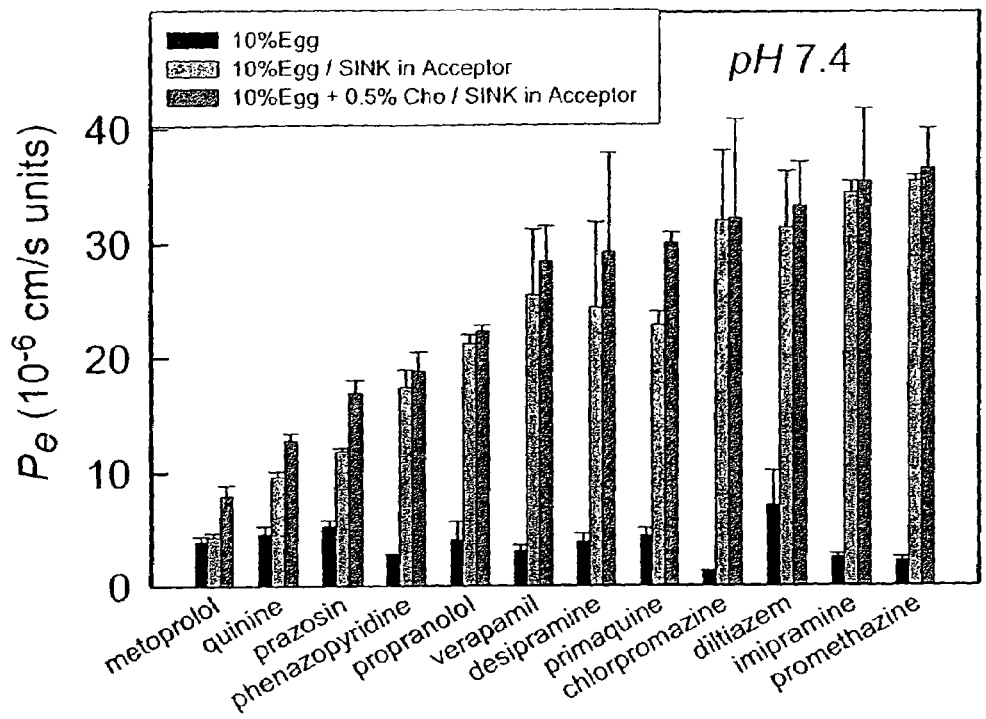
FIG. 6 illustrates (a) effective permeability and (b) membrane retention for a series of weak bases in various 10% egg lecithin PAMPA models, pH 7.4 (Models 4.0, 4.1, and 5.1).
Figure 6:
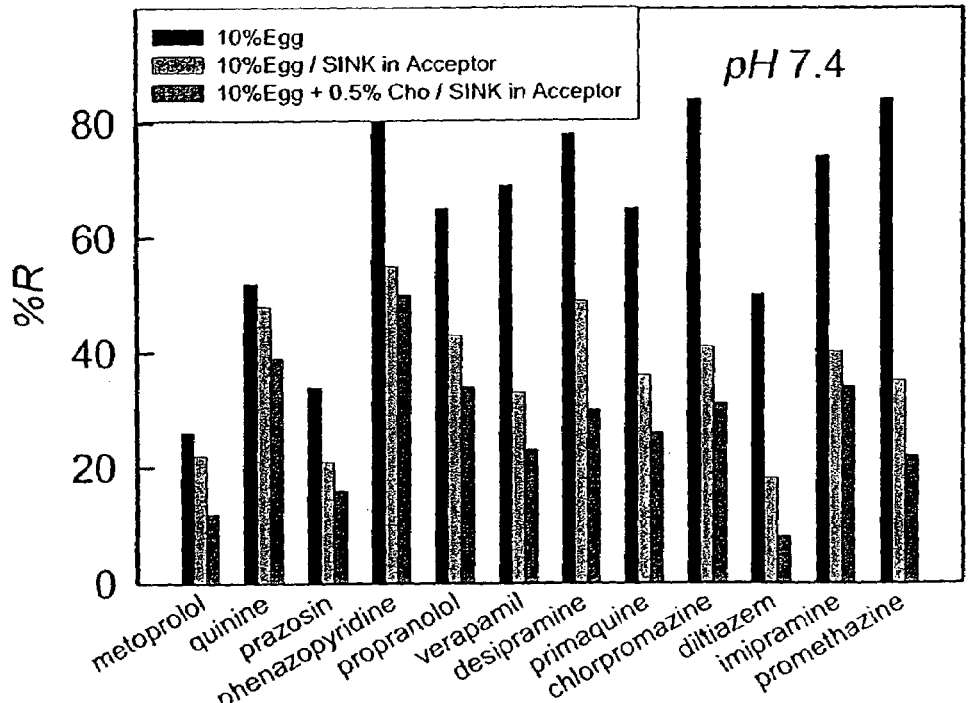

The '60% lecithin' grade egg lecithin from Sigma-Aldrich was tested. Kansy dissolved 10% wt/vol of this egg lecithin in dodecane, with added cholesterol. Table 3 lists the results of the various 10% egg lecithin models tested by us. FIG. 6 shows (a) permeability and (b) membrane retention results for weak-base test molecules, with and without sink and 0.5% wt/vol cholesterol (Models 4.0, 4.1, 5.1). The presence of a sink dramatically increases permeability, as indicated in FIG. 6(a). In some cases, further significant increases in permeability were realized by the use of cholesterol, even though its amount was only 0.5%. Only in the diffusion-limited cases, right side of FIG. 6(a), was there only minimal enhancement due to cholesterol.

Without an acceptor sink, membrane retention is very high, with many basic molecules showing R>80% (Model 4.0). With the imposed acceptor sink, the membrane retention of many of the moldecules dropped by as much as a half (Model 4.1). Furthermore, just 0.5% wt/vol cholesterol in dodecane (in addition to the acceptor sink) caused increased retention to drop by at least a further 10%–30% (Model 5.1).

The peculiar depression of metoprolol and quinine permeability in 2% DOPC (Model 1.0) was not seen with egg lecithin (Models 4 and 5). Metoprolol and quinine are significantly more permeable in the lecithins, in line with expectations based on relative octanol-water lipophilicity.

EXAMPLE 5

Soybean Lecithin and the Effects of Phospholipid Concentrations

We explored the use of Avanti's '20% lecithin soy lipid extract' grade of soybean lecithin, and dissolved it at various concentrations in dodecane (Models 6–12). This is not a highly-purified grade of lecithin, and contains 37% unspecified neutral lipids, most likely asymmetric triglycerides ('white fat'). We chose this grade because it contained negatively-charged phospholipids, having a charged-to-zwitterionic lipid ratio about halfway between that of brush-border membrane (BBM) lipid and BBB (RBE4 cultured endothelial cell line) compositions.

Results

PAMPA lipid models were prepared with the soybean lecithin, 10–74% wt/vol in dodecane containing 1.5% absolute ethanol, and selected results are summarized in Table 4. It is clear to those practiced in the art that solutions with lower than 10% lecithin will also be beneficial. These newly-formulated lipids have net negative charge at pH 7.4. The inositol (predominant negatively-charged lipid) content is four times higher in soybean than in egg lecithin.

But, when high phospholipid fractions are used, severe experimental problems arise. With lipophilic sample molecules, the use of concentrated phospholipid artificial membranes leads to two unwanted effects: (a) nearly complete membrane retention (90–100%) and (b) highly diminished permeability (extinguished in some cases), both effects presumably due to excessive drug-membrane binding.

These adverse effects are nearly eliminated by using an ionic surfactant to create a very strong sink condition in the acceptor compartment of the permeation cell. The negative charge on the micelles formed from the surfactant added to the acceptor compartment appears to play a stabilizing role.

Figure 7A:
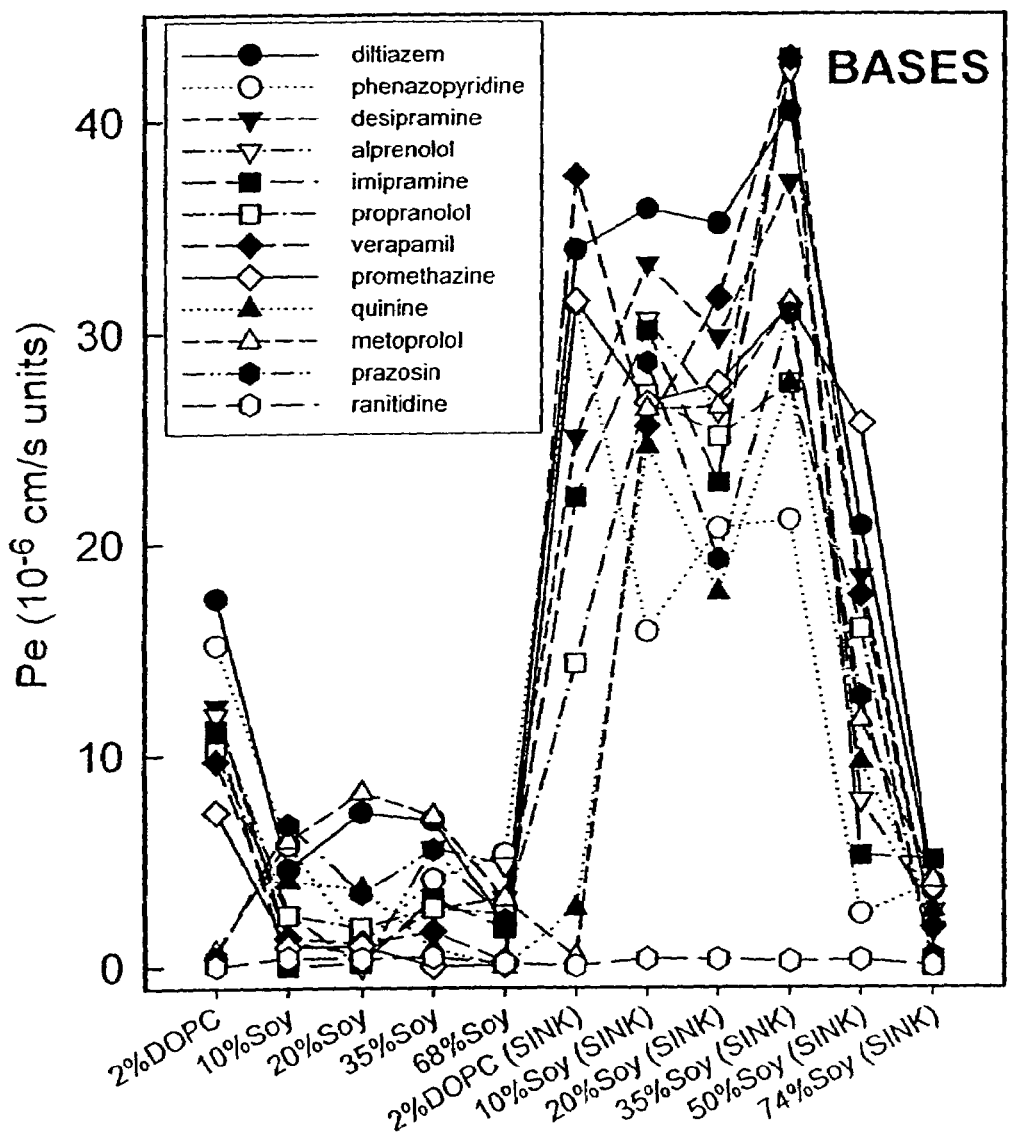
FIG. 7 shows soybean lecithin effective permeability at various concentrations in dodecane, with and without acceptor sink, pH 7.4: (a) bases, (b) acids, (c) neutral molecules (Models 6–12). ("With sink" is noted as "SINK" on X-axis.)
Figure 7B:
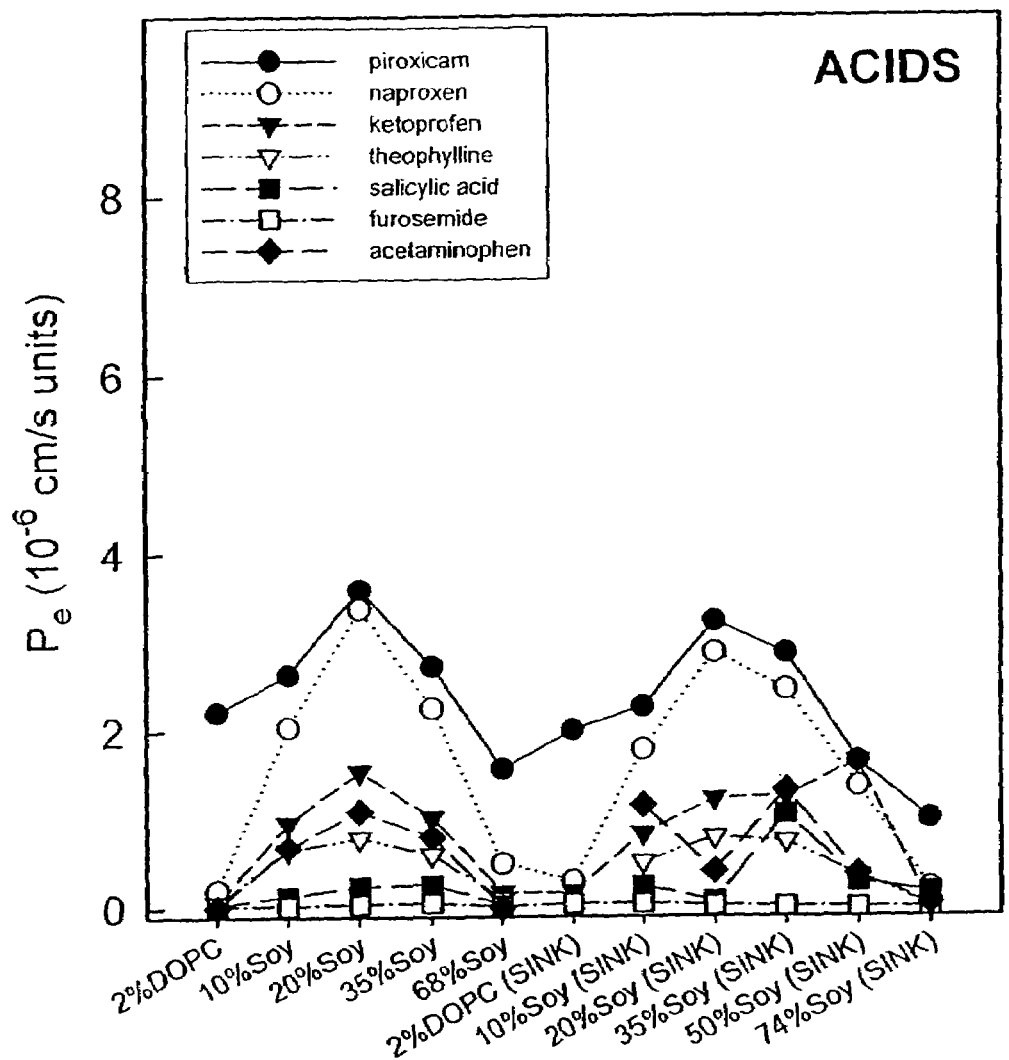
Figure 7C:
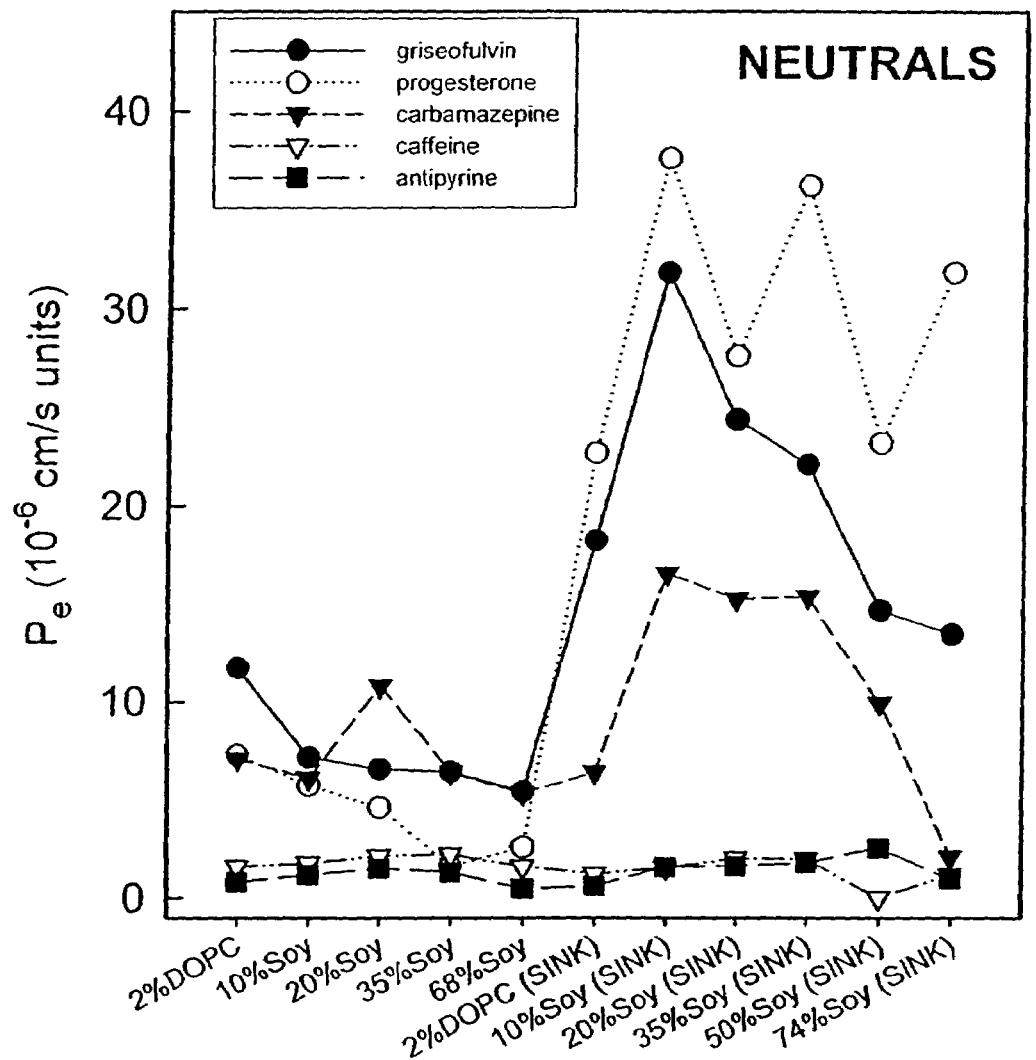
Figure 8A:
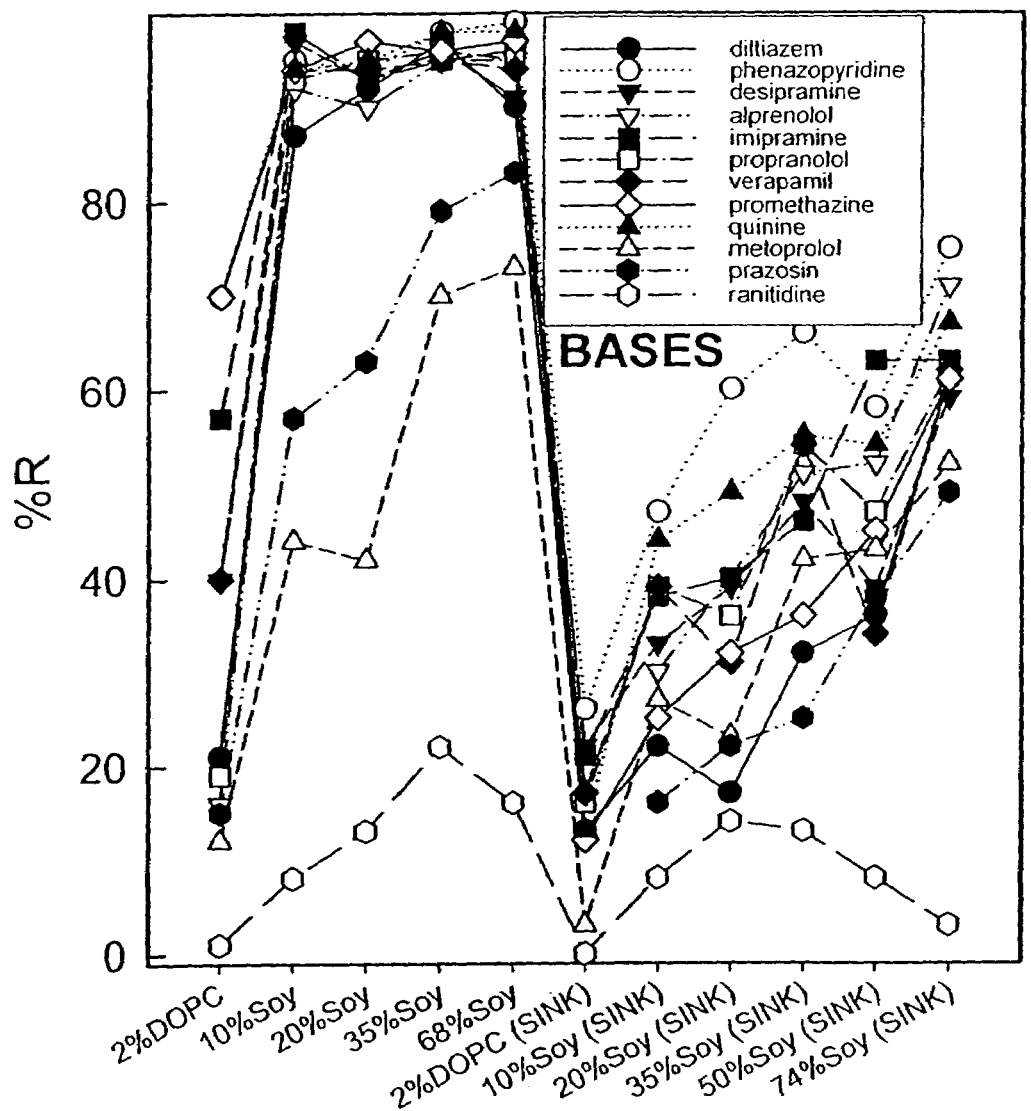
FIG. 8 shows soybean lecithin membrane retention at various concentrations in dodecane, with and without acceptor sink, pH 7.4: (a) bases, (b) acids, (c) neutral molecules (Models 6–12). ("With sink" is noted as "SINK" on X-axis.)
Figure 8B:
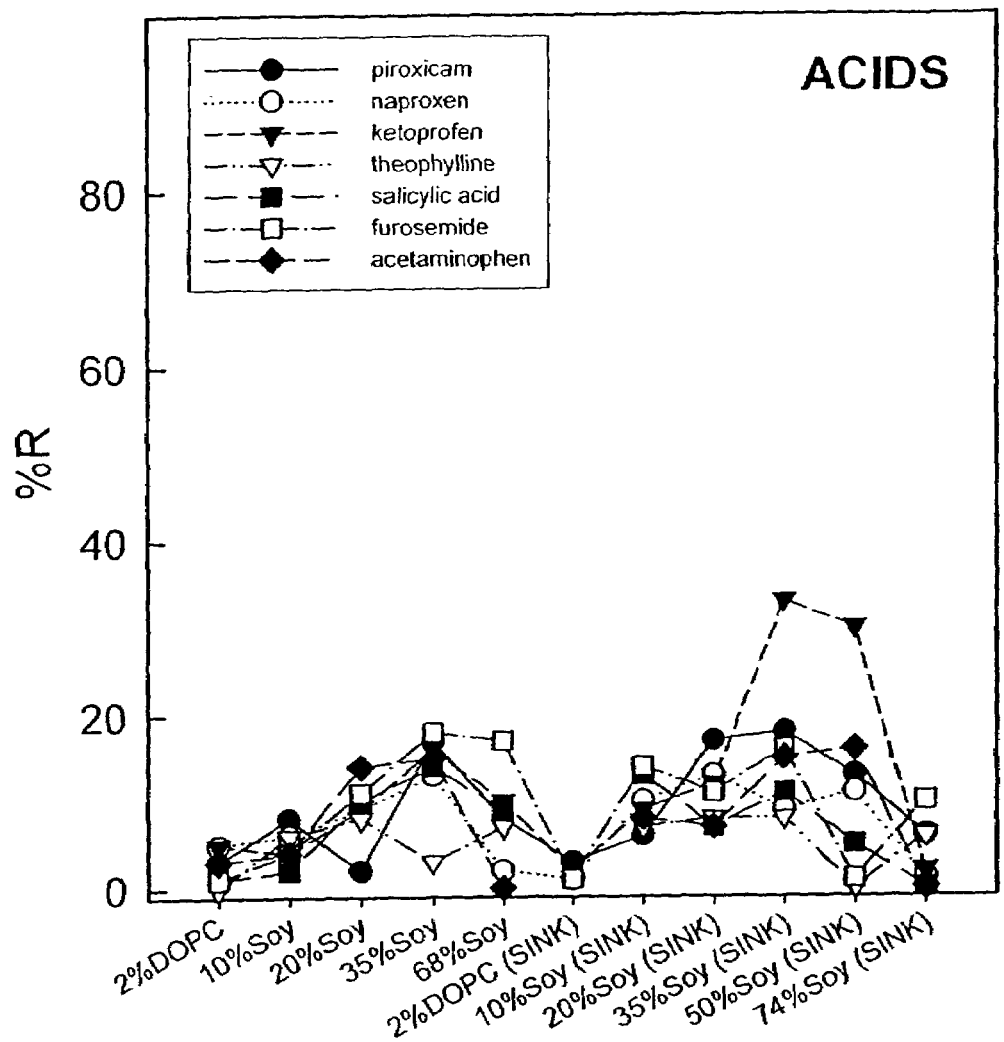
Figure 8C:
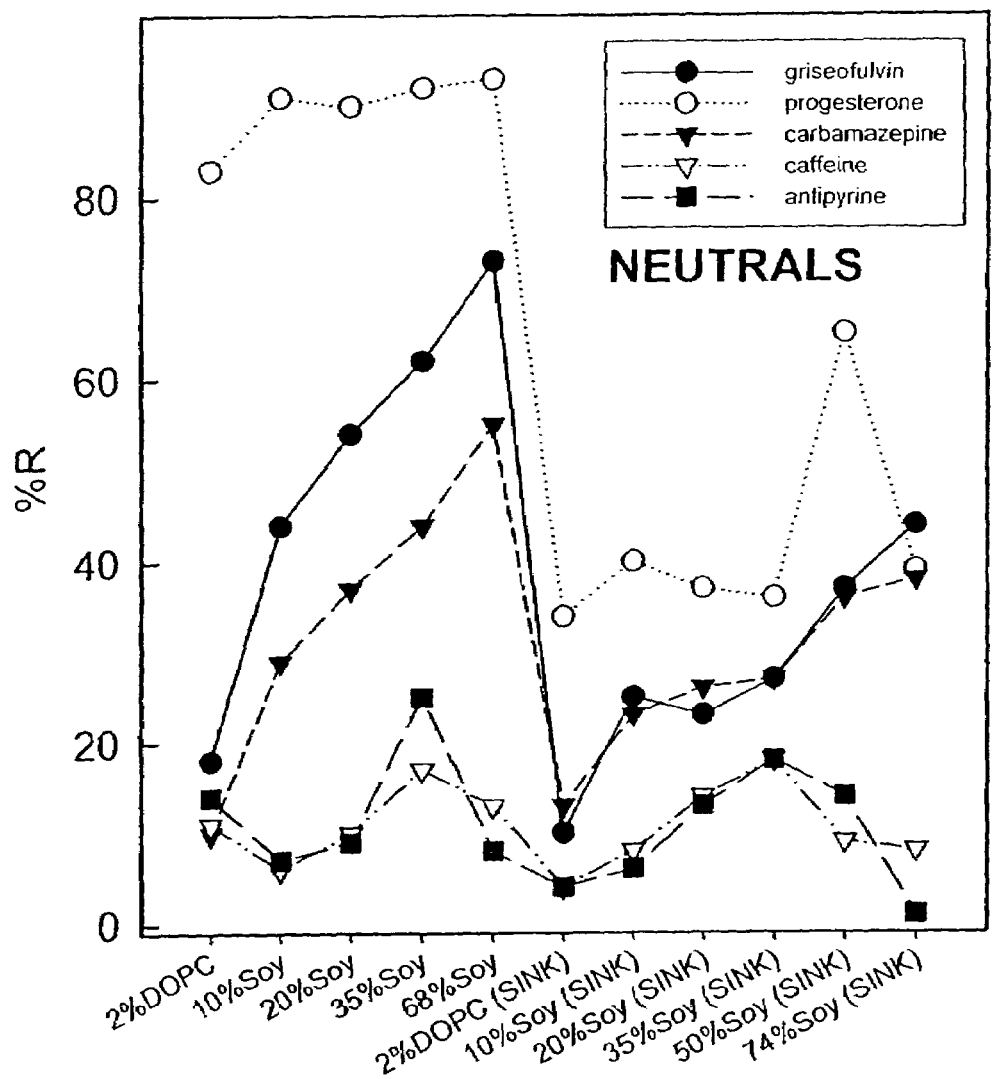

Tables 4 and 5 list the pH 7.4 permeability and retention values (with and without sink-forming additive) of the test molecules grouped as bases, acids, and neutral molecules in FIGS. 7a–c. FIGS. 7(a–c) are graphs of the effective permeability, with (Models 6.1–12.1) and without (Models 6.0–11.0) acceptor sink, as a function of increasing soy content, beginning with 2% DOPC (Models 1.0 and 1.1) for a bench mark. FIGS. 8(a–c) are plots of the corresponding membrane retention.

The permeability of most of the bases decreases steadily as the phospholipid fraction increases. There are some significant exceptions. Metoprolol, which is only moderately permeable in the DOPC lipid, becomes appreciably permeable in 10% soy lecithin. But, at the 68% soy level, this molecule also shows reduced transport.

The permeability of the acid examples rise with increasing phospholipid content, up to 20% lipid, with rank ordering preserved. Naproxen and ketoprofen show the most dramatic increases in going from 2% DOPC to 10% soy lipid membranes, somewhat higher in soy than in egg. Piroxicam shows less sensitivity to lipid changes. For higher phospholipid concentrations, permeability of all the acids decreases.

The nonionizable molecules respond to the changes in the phospholipid content. Griseofulvin has its highest permeability in the lowest phospholipid-containing membranes.

The most remarkable change of properties in going from 2% to 10% phospholipid occurs with the membrane retention of the bases. Most of the bases are retained above 90% in all of the soy lecithin cases (up to 68% lecithin in dodecane). This is thought to be largely due to the added ionic interactions between positively-charged sample molecules and the negatively-charged membrane constituents.

Acids show small, steady increases in membrane retention with increasing phospholipid content. Even though the acids are negatively charged at pH 7.4, as are a portion of the membrane constituents, the increasing phospholipid content draws the test molecules into the membrane barrier, due to increased hydrogen-bonding and any other lipophilic forces arising from the phospholipids (increased membrane-water partition coefficient). Decreased surface pH due to the membrane's negative surface charge may also play a role in increasing permeability of weak acids.

Neutral molecules show a range of retention properties between those of acids and bases. Progesterone membrane retention is very high in all cases. Griseofulvin and carbamazepine retention steeply increase with phospholipid content.

The patterns of retention follow the lipophilicity properties of the molecules.

Lipophilicity and the Decrease in Permeability with Increased Phospholipid Content in Dodecane FIGS. 7(a–c) clearly show that after some critical soy content in dodecane, $P_e$ values decrease with increasing soy, for both sink and no-sink conditions. Since liposome(phospholipid)-water partition coefficients are generally higher than alkane-water partition coefficients for drug-like molecules, soy lecithin may be assumed to be more lipophilic than dodecane. [Avdeef, A., Curr. Topics Med. Chem. 2001, 1, 277–351] The more lipophilic molecules preferentially concentrate in the more lipophilic phase, leading to decreased permeability, as the concentration of solute in the lower-lipophilicity phase decreases. In the soy lecithin models, the lipid phases are systematically varied, with reference to a molecule of a particular lipophilicity. For example, the maximum permeability for most molecules occurs at about 20% wt/vol lecithin in dodecane.

Acceptor Sink Condition to Offset the Attenuation of Permeability

The preceding paragraph discussed the decrease in permeability with increasing lecithin content in dodecane in terms of shifting concentration distributions between a weak lipophilic domain (dodecane) and a stronger lipophilic domain (lecithin). Another view of this may be that at the molecular level, as the amount of phospholipid increases, the effects of ionic and H-bonding play a more prominent role in the transport process. Generally, % R of the lipophilic molecules increases with increasing lecithin content, most dramatically in the case of lipophilic bases. Such losses of compound to the membrane barrier pose a challenge to the analysis of concentrations, which can be significantly diminished (to undetectable levels at times) in the aqueous compartments. At the same time, the permeability drops to near vanishing values in 68% soy lecithin—dodecane membranes. Under these conditions, the permeability of the lipophilic bases and acids converge to similar low values, significantly departing from the expected values based on the octanol-water lipophilicity scale (Table 1) and the pH-partition hypothesis. This excessive drug-membrane binding would not be expected under in vivo conditions in the small intestine, due to the naturally occurring sink state. There would be competing lipid environments in the receiving compartment (serum proteins, other membrane barriers, etc.), and the solute-binding membrane would release a portion of the retained lipophilic molecules, resulting in a concomitant higher effective permeability.

The transport properties of the molecules in concentrated soy lecithin, Models 6.0–11.0 in Table 4, do not adequately model the in vivo permeability reported by Winiwarter et al. in Table 1. [Winiwarter, S., Bonham, N. M., Ax, F., Hallberg, A., Lennernas, H., Karlen, A., J. Med. Chem. 1998, 41, 4939–4949] The strategy to overcome this shortcoming of the model involves creating a model sink condition. However, the use of BSA or other serum proteins, although easily effected, is not practical in high-throughput screening, since the UV absorption due to the proteins would make determination of the compound concentrations in the acceptor compartments by direct UV spectrophotometry nearly impossible in most cases. Without knowledge of the concentration of sample in the acceptor compartment, the determination of % R would not be practical.

Some PAMPA practitioners, using BSA to create sink conditions, make the simplifying assumption that membrane retention is zero. It is neither reasonable nor warranted to expect that membrane retention be eliminated in the presence of serum proteins or other practical substitutes in the acceptor compartment. FIGS. 8(a–c) clearly show that retention under sink conditions can still be substantial. Since lipophilic molecules have affinity for both the membrane lipid and the serum proteins, membrane retention is expected to decrease, by the extent of the relative lipophilicity of the drug molecules in membrane lipid vs. serum proteins, and by the relative amounts of the two competitive-binding phases. Generally, the serum proteins cannot extract all of the sample molecules from the phospholipid membrane phase at equilibrium. Thus, to measure permeability under sink conditions, it is still necessary to characterize the extent of membrane retention. This has not been done in the reported literature.

We found that the negatively-charged surfactant, sodium laurel sulfate, can be successfully substituted for the serum proteins used previously. In low ionic strength solutions, the critical micelle concentration (cmc) of the surfactant is about 8 mM. We explored the use of both sub-cmc and micelle-level concentrations. We most often use saturated micelle solutions (about 35 mM).

The addition of surfactant to the acceptor solution allows for the re-distribution of lipophilic permeants between the PAMPA membrane phase and the surfactant phase in the acceptor compartment, according to the relative lipophilicity of the two oil phases. Positively-charged drug molecules will favor additional binding to the negatively-charged micelles, unless the PAMPA membrane lipid composition also has negative charge.

The effect of the surfactant is most dramatic for the bases and neutral molecules studied, as shown in for Models 6.1–12.1 in Tables 5a and 5b. Permeability increased by up to four-fold for the lipophilic bases and neutral molecules, and in most cases of bases and neutral compounds, membrane retention was decreased by a half (FIGS. 7 and 8).

The transport properties of the acids did not respond significantly to the presence of the sink. This may be because at pH 7.4 the acids are negatively-charged, as are the phospholipid membranes and also the surfactant micelles; electrostatic repulsions balance out the attractive forces due to increased membrane lipophilicity. Lowered surface pH may also play a balancing role.

Comparing Egg and Soy Lecithin Models

The negative-charge lipid content in the egg lecithins is not as high as that found in BBM and especially in BBB lipids. Furthermore, the negative-charge content in the egg lecithin is about one-fourth of that in the soy lecithin. This is clearly evident in the membrane retention parameters for the bases at the 10% lecithin levels (Models 4.0 in Table 3 vs. Model 6.0 in Table 4), being about 20–30% lower for the lipophilic bases in egg, compared to soy.

For acids, the membrane retention actually increases in the case of egg lecithin, compared to soy lecithin. This may be due to decreased repulsions between the negatively-charged sample and negatively-charged phospholipid, allowing H-bonding and hydrophobic forces to more fully realize in the less negatively charged egg lecithin membranes.

The neutral molecules display about the same transport properties in soy and egg lecithin, in line with the absence of direct ionic effects.

These differences between egg and soy lecithins make soy lecithin the preferred basis for further model development.

EXAMPLE 6

Iso-pH Permeability Measurements Using Soy Lecithin

Figure 9:
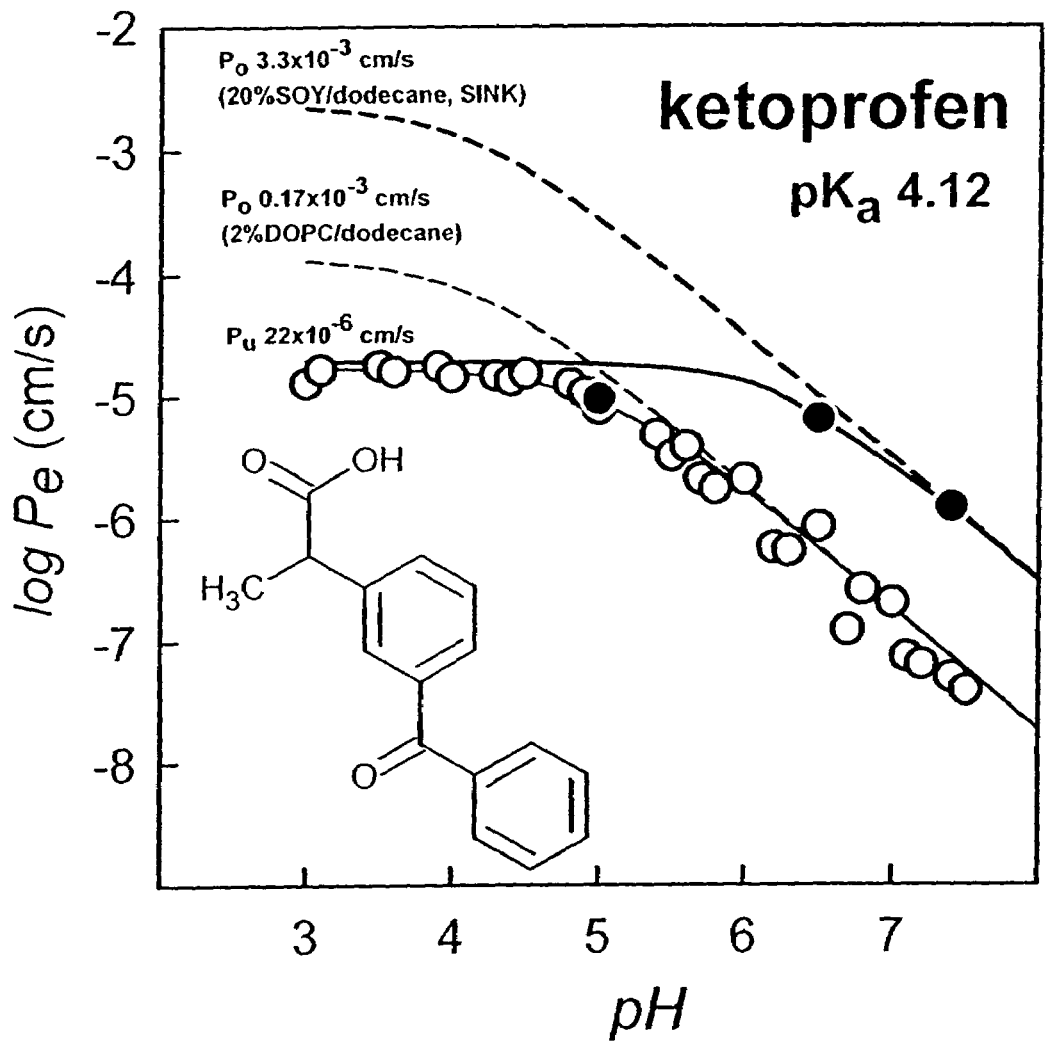
FIG. 9 shows iso-pH profiles: logarithm of the effective permeability vs. pH for a weak acid, ketoprofen, in 2% DOPC system (open circles, Model 1.0 over a range of pH values) and 20% soybean lecithin system (filled circles, Models 7.0, 13.0, and 14.0).

Table 6 lists iso-pH effective permeability measurements using the soy lecithin (20% wt/vol in dodecane) membrane PAMPA (Models 7.1, 13.1, and 14.1) The negative membrane charge, the multicomponent phospholipid mixture, and the acceptor sink condition result in different intrinsic permeability for the probe molecules. FIG. 9 shows the relationship between the 2% DOPC (Model 1.0—open circles) and the 20% soy (Models 7.0, 13.0, 14.0—closed circles) iso-pH PAMPA systems for ketoprofen. Since the intrinsic permeability of ketoprofen in the soy lecithin membrane is about 20 times greater than in DOPC membrane, the flat diffusion-limited transport region of the log $P_e$ curve is extended to higher pH values. Thus less evidence of membrane-limited transport is visible in the physiological pH range when the soy lecithin system is used. For this reason, correction for the UWL effect is all the more important when devising oral absorption prediction models, which reflect the pH gradient found in the small intestine.

EXAMPLE 7

Gradient-pH Permeability Measurements Using Soy Lecithin

Figure 10A:
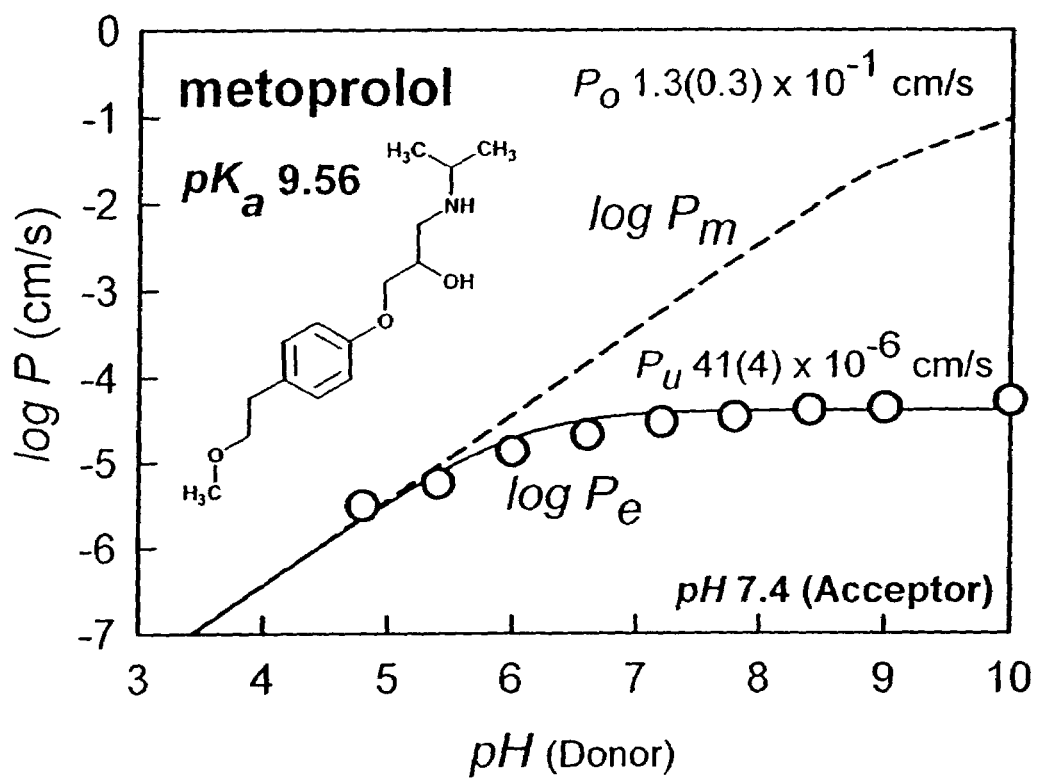
FIG. 10 shows gradient-pH profiles, double-sink conditions, 20% wt/vol soybean lecithin in dodecane, Models 7.1 and 16.1–19.1: (a) weak base, metoprolol, and (b) ampholyte, piroxicam (in pH range corresponding to acidic group ionization).
Figure 10B:
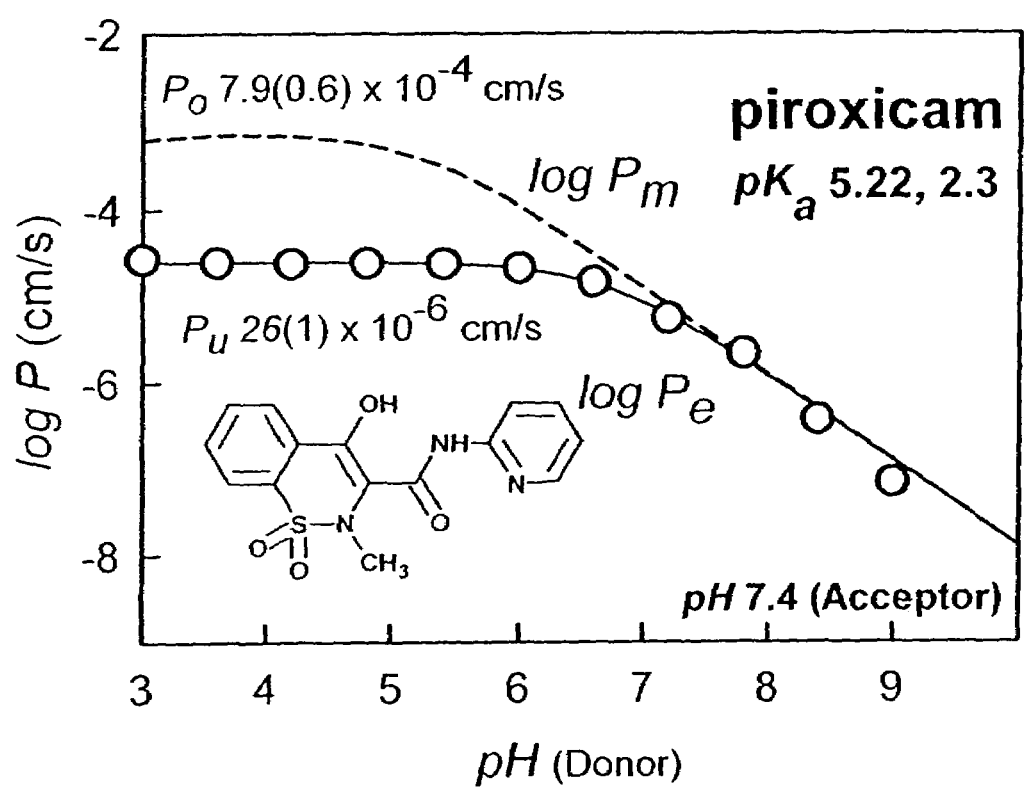

The gradient-pH soy lecithin, acceptor sink systems (Models 16.1–19.1) were explored in the search for the best gastrointestinal (GIT) PAMPA model. FIG. 10(a) shows an example of a weak base, metoprolol. The acceptor pH was 7.4, but the donor pH values ranged from 3 to 10. FIG. 10(b) shows an example of an acid, piroxicam. In the above examples, the diffusion-controlled zone spans a much larger pH range than in the DOPC system. This is the consequence of increased intrinsic permeability in the soy-based system.

Table 7 summarizes the Walter-Gutknecht analysis of the gradient-pH experiments. The range of intrinsic permeability spans eleven orders of magnitude! The UWL permeability ranged from 16 to $52 \times 10^{-6}$ cm s$^{-1}$. Those molecules which appeared to bind strongly to the sink-forming acceptor surfactant showed UWL permeability values, $P_u$, that were about twice those calculated from the iso-pH non-sink assays. The strong binding between the solute and the surfactant in the acceptor wells drives the unbound fraction of the solute molecules in the acceptor compartment to near zero. According to the pH partition hypothesis, it is the unbound neutral species which crosses the membrane. Since its concentration is near zero, the acceptor-to-donor back flux is nil. So the UWL resistance on the acceptor side is of little consequence in the transport process. When strong binding takes place under the artificial sink condition, only the UWL on the donor side directly contributes to the overall resistance. Hence, $P_u$ values are calculated to be about twice as large as in the case of no-sink iso-pH. Table 8 lists the interpolated apparent and membrane permeability, along with membrane retention, of the probe molecules used in the gradient-pH study, at pH values 5.0, 5.5, 6.0, 6.5, and 7.4.

EXAMPLE 8

UV Spectral Data

The use of direct UV spectrophotometry to measure sample concentrations in pharmaceutical research is not common. Mostly, HPLC or LC/MS methods are used. The UV method is much faster than the other methods, and this is very important in high-throughput screening.

If samples are highly impure or decompose readily, the UV method is inappropriate to use. LC/MS has been demonstrated to be a suitable detection system under those conditions. However, when LC/MS requires multiple-point calibration curves, and thus is relatively slow.

Figure 11:
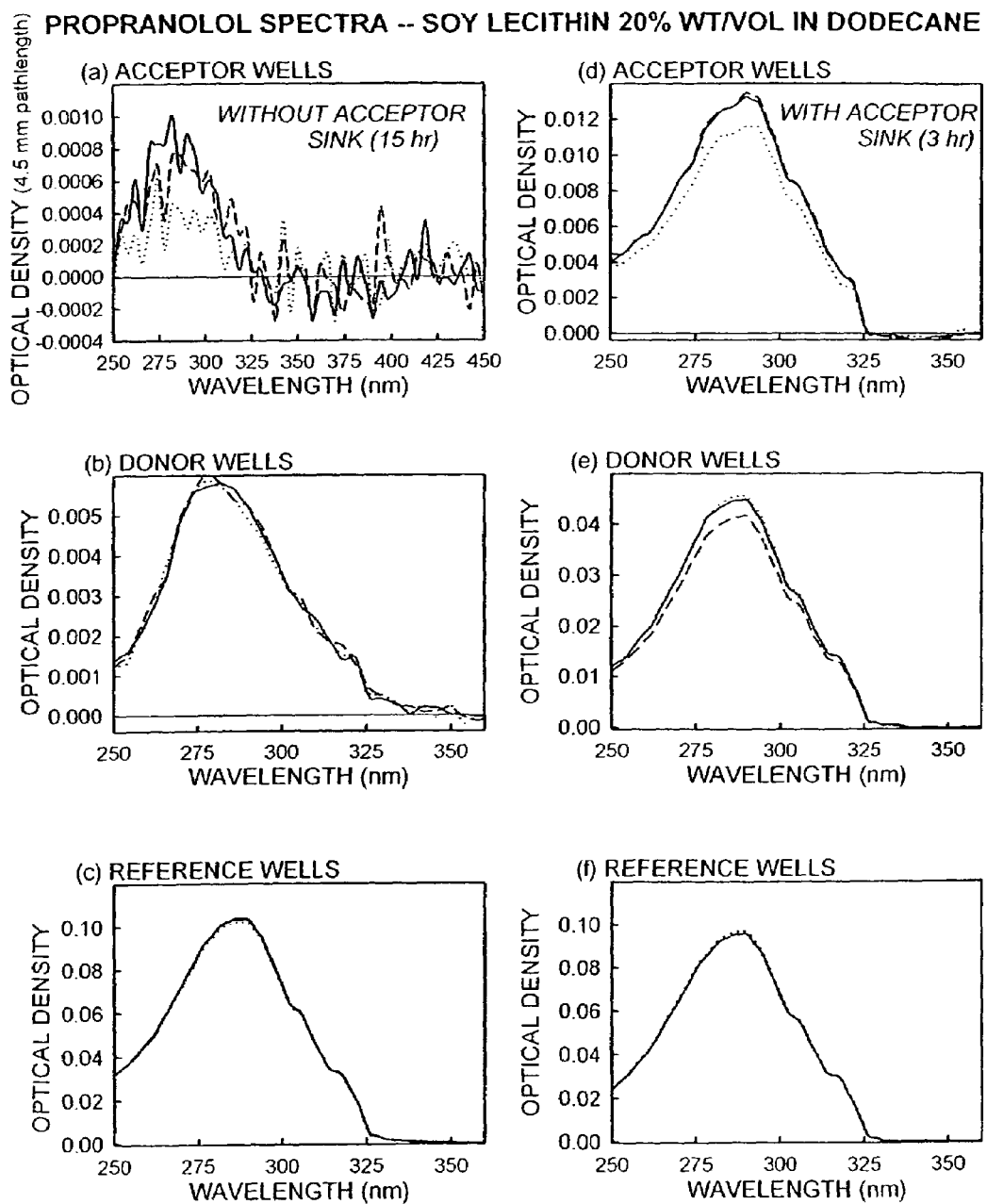
FIG. 11 shows UV spectra of propranolol (47 µM, pH 7.4, each in triplicate), without acceptor sink, Model 7.0: (a) acceptor wells, after 15 h, (b) donor wells, after 15 h, (c) reference wells (donor at time 0), and with surfactant-based sink, Model 7.1: (d) acceptor, after 3 h, (e) donor, after 3 h, (f) reference (donor at time 0).

FIGS. 11(a–c) show the no-sink acceptor, donor, and reference spectra of 48 µM propranolol at the end of 15 h PAMPA assay using 20% wt/vol soy lecithin in dodecane. The sum of the donor (3 µM) and the acceptor (<1 µM) well concentrations indicates that 45 µM is lost to the membrane. In the absence of sink-creating surfactant, only a trace of propranolol reached the acceptor wells at the end of 15 h, with 94% of the compound trapped in the membrane, compared to 19% in the 2% wt/vol DOPC case. The effective permeability in 20% soy decreases to $1.8 \times 10^6$ cm s$^{-1}$, compared to the DOPC value of $10.2 \times 10^{-6}$ cm s$^{-1}$.

With surfactant-created sink condition in the acceptor compartment, the amount of propranolol reaching the acceptor wells is dramatically increased (FIG. 11(d)), with the concomitant decrease in membrane retention from 94% to 41%. Furthermore, the effective permeability rises to $25.1 \times 10^{-6}$ cm s$^{-1}$, more than a ten-fold increase, presumably due to the membrane desorption effect of the acceptor surfactant. Only 3 h permeation time was used in the case (FIGS. 11(d–f)). With such a sink at work, one can lower the permeation time to less than 2 h and still obtain very useful UV spectra. This is good for high-throughput requirements.

FIG. 11(a) shows that reproducible absorbance can be measured with optical density (OD) values as low as 0.0008, based on a spectrophotometric pathlength of 0.45 cm. The baseline noise (OD in the range 350–500 nm in FIG. 11(a)) is estimated to be about ±0.0002 OD units peak-to-peak. This high level of performance exceeds the spectrophotometer manufacturer's specification by about a factor of five, and is due to the software program processing of the raw optical density data, taking into account spectra of acceptor-blank and donor-blank solutions, corrections of spectral anomalies due to dust, air bubbles, and impurities, as well as other baseline corrections.

EXAMPLE 9

Effects of Cyclodextrin in Acceptor Wells

The method for creating acceptor sink condition discussed in the preceding examples is based on the use of a surfactant solution. Under those circumstances, anionic micelles act to accelerate the transport of lipophilic molecules. We also tested the use of other sink-forming reagents, including uncharged cyclodextrins. Table 9 compares the sink effect of 100 mM β-cyclodextrin added to the pH 7.4 buffer in the acceptor wells to that of the anionic surfactant (Model 7.2). Cyclodextrin creates a weaker sink for the cationic bases, compared to the anionic surfactant. The ionic binding force between charged lipophilic bases and the anionic surfactant micelles in the preceding examples is missing in the uncharged cyclodextrin system. Some molecules (e.g., metoprolol, carbamazepine) may have the suitable shape to take advantage of strong cyclodextrin binding, and thus indicate substantially increased permeability.

EXAMPLE 10

Effect of β-Cyclodextrin in Both Acceptor and Donor Wells

Table 10 summarizes the permeability measurements where β-cyclodextrin (β-CD) was added to both the acceptor and donor solutions. The preferred membrane barrier was 20% wt/vol soy lecithin in dodecane. Without the sink-forming donor and acceptor constituent (β-CD), the membrane retention of the weak bases exceeded 90% in most cases, and in some cases, it was not possible to characterize permeability, since most of the material was absorbed into the membrane barrier. The addition of 100 mM β-CD to both sides of the membrane barrier dramatically lessened the loss of sample to the membrane barrier. Some molecules, such as propranolol and progesterone were greatly affected by the presence of the cyclodextrin. This use of sink-forming additives in both the acceptor and donor wells is the proposed strategy to model blood-brain-barrier permeation, where a predominant acceptor sink state is absent under in vivo conditions.

EXAMPLE 11

Double-Sink PAMPA Model for the Prediction of Human Jejunal Permeability (HJP)

Human jejunal permeabilities reported by Winiwarter et al. were selected as the in vivo target to validate improvements of the new in vitro PAMPA model. In particular, three acids (ketoprofen, naproxen, piroxicam), three bases (metoprolol, propranolol, verapamil) and two nonionized molecules (carbama-zepine, hydrochlorothiazide), studied by Winiwarter et al., were selected as probes. In the human permeability data (Table 1), the ordering of permeability of these eight probe molecules is most peculiar, in that naproxen, ketoprofen, and piroxicam are at the top of the list, yet these three acids are ionized under in vivo pH conditions and have lipophilicity (log $K_d$, Table 1) values near or below zero. On the other hand, the most lipophilic molecules tested in humans, verapamil and carbamazepine (log $K_d$ about 2.5), are in second-rank ordering. Explanation of the odd ordering have not been offered in the literature. We took it as a challenge, and as a quantitative measure of the improvement of the PAMPA method of this invention, to explain these anomalies in our optimized in vitro gastrointestinal (GIT) model. We tested several membrane models, identified in Table 11, in a linear regression scheme, by comparing the logarithms of the human jejunal permeabilities to the logarithms of the measured PAMPA values for each lipid model. For each PAMPA model in Table 11, the linear regression correlation coefficient, $r^2$, was used to assess the appropriateness of the model. A similar comparison was done between the human data and published Caco-2 values.

Figure 12:
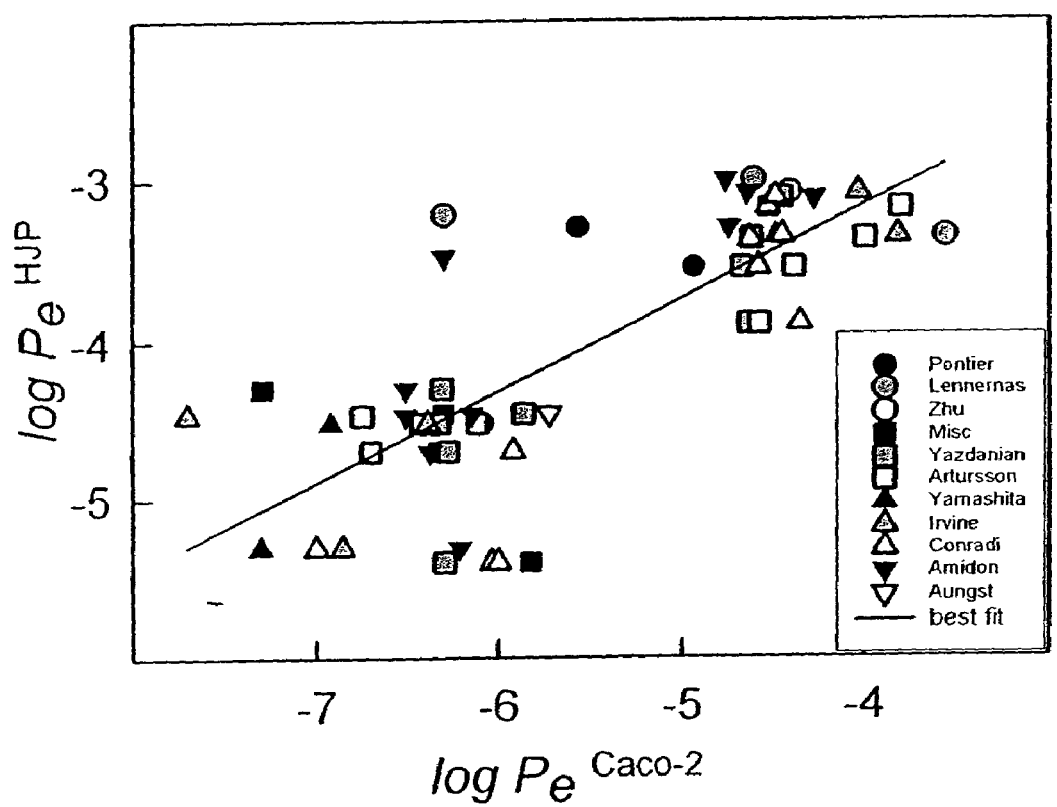
FIG. 12 compares human jejunal permeability [Winiwarter, S., Bonham, N. M., Ax, F., Hallberg, A., Lennernas, H., Karlen, A., J. Med. Chem. 1998, 41, 4939–4949] to Caco-2 permeability, taken from the published literature.

FIG. 12 shows a plot of log $P_e^{HJP}$ (human jejunal permeability) vs. log $P_e^{Caco-2}$ taken from the literature, based on the work of more than eleven laboratories. The $r^2$ for the correlation is 0.62. It is clear from the plot that some laboratories better predicted the HJP than other laboratories.

Table 11 shows the results for specific PAMPA models tested in the invention. The two columns on the right are the $r^2$ values in the comparisons of PAMPA vs. human jejunal permeability for the eight selected probe molecules. The neutral-lipid systems (Models 1.0–3.0) at pH 7.4 do not explain the permeability trend indicated in the human jejunal permeabilities. Octanol was least effective, with $r^2$ 0.01. This should not be too surprising, since we did note that the appearance of naproxen, ketoprofen, and piroxicam at the top of the HJP ordering was most unexpected. Our 'expectations' were based on the octanol-water lipophilicity scale, which clearly does not correlate with the HJP trend. Adding a sink condition to the 2% DOPC model (Model 1.1) improves correlation ($r^2$ increases from 0.33 to 0.53). But further improvements are evident in this PAMPA invention.

Several lecithin models were tested at pH 7.4. Considerable improvements were achieved when iso-pH solutions were tested, at pH 6.5 and 5.0 (Models 13.1 and 14.1 in Table 11). At pH 5.0, $r^2$ reached 0.86 (Model 14.1).

Figure 13:
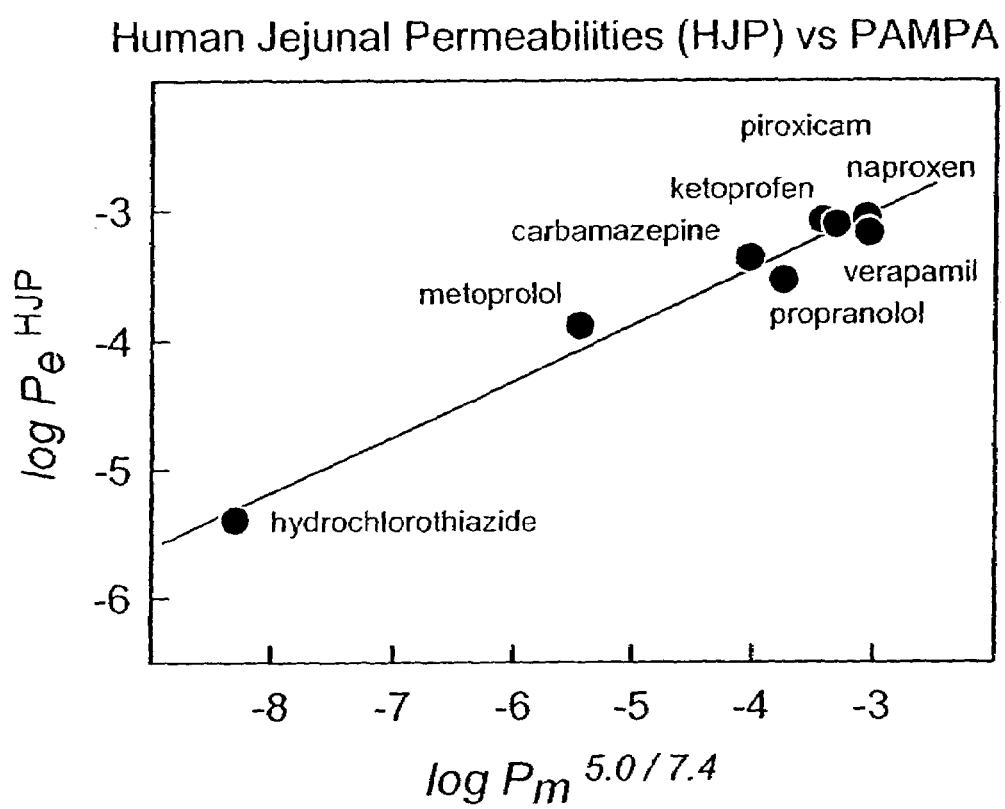
FIG. 13 compares human jejunal permeability to that measured by the double-sink PAMPA method (Model 18.1).

The best correlations were observed under gradient-pH and sink conditions ('double-sink' set at the bottom of Table 11), with the donor pH 5.0 and acceptor pH 7.4 producing $r^2$ 0.97 The best double-sink GIT model, with donor pH 5.0, predicts the human jejunal permeabilities as well as the best reported Caco-2 model, and considerably better than the rest of the reported Caco-2 models, as demonstrated in FIG. 13. This most effectively demonstrates some of the improvement in the PAMPA invention.

EXAMPLE 12

Sum-$P_m$ PAMPA Model for the Prediction of Human Intestinal Absorption (HIA)

The strategy of the preceding sections was based on predicting the permeabilities of drug compounds in the human jejunum. The rest of the intestinal tract has higher luminal (donor) pH, and this needs to be factored in when considering models to predict not human permeabilities, but human absorption.

Figure 14:
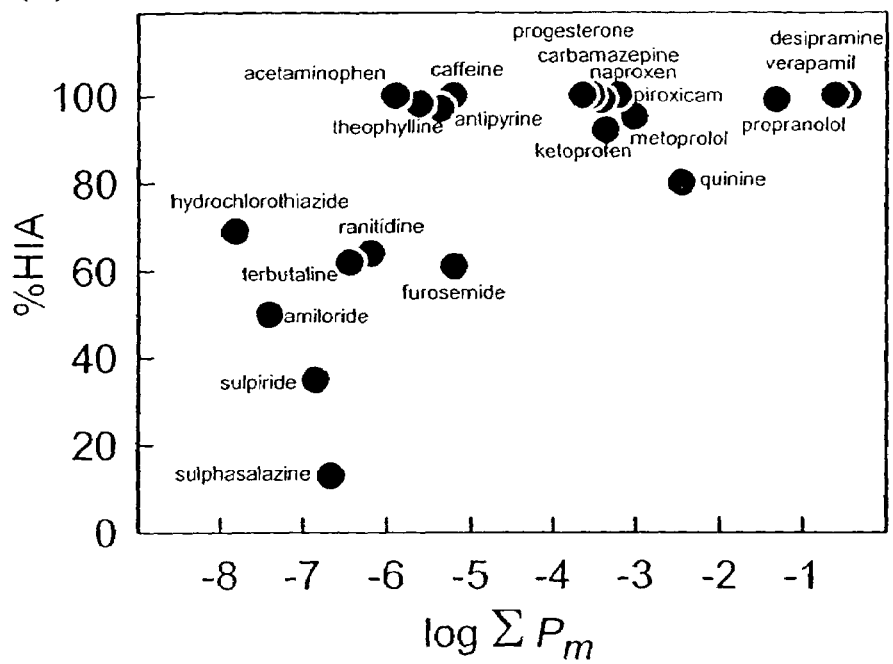
FIG. 14 compares human intestinal absorption fraction (% HIA) to (a) the double-sink sum-$P_e$ PAMPA GIT model, and (b) human jejunal permeability.
Figure 14:
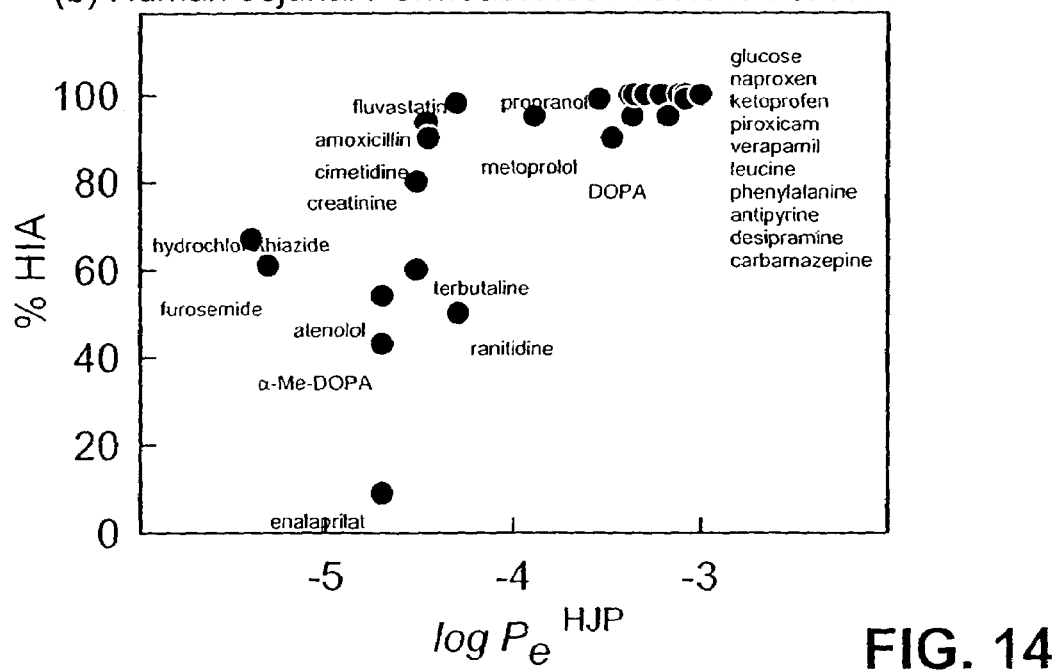

The absorption model developed consists of summing permeability values. This is roughly equivalent to integrating a system with parallel absorption taking place in different parts of the intestine. Our preference is to perform PAMPA assay at three gradient-pH conditions, with acceptor sink included ('double-sink' method): donor pH 5.0, 6.5, and 7.4, with acceptor pH always at 7.4. FIG. 14(*a*) shows such a double-sink sum-$P_m$ ($P_m$ is the $P_e$ value corrected for the UWL) plot. FIG. 14(*b*) shows the plot of log $P_e^{HJP}$ vs. % HIA—human permeability data attempting to predict human absorption. As can be seen, the PAMPA data and the HJP data perform equally and tolerably well. Of particular note is that the PAMPA scale covers nearly eight orders of magnitude, compared to about two and a half orders for the HJP data. Such a spread in the PAMPA data could facilitate the selection of well-absorbed molecules from those poorly absorbed. This is further evidence of the improved PAMPA invention.

Finally, it should be mentioned that there are enormous cost savings in the PAMPA in vitro method, compared to the in vivo method.

Those with expertise in this field will recognize variations in the invention which are equivalent thereto.

What is claimed is:

1. An assay method for high-throughput spectroscopic measurement of the membrane permeability and membrane retention values for a compound, said method not requiring knowledge or measurement of the molar absorptivity of said compound, and not requiring a calibration curve relating known concentrations of said compound to a spectroscopic property of said compound, said method comprising the steps of:

a. preparing a sample solution of said compound in an aqueous buffer of known pH and separating said sample solution from any precipitate, said separated solution constituting a reference solution, b. preparing an initial donor solution of said compound, by placing an aliquot of said reference solution in a donor compartment, said donor compartment being on one side of a membrane barrier, c. placing an initial acceptor solution in an acceptor compartment, said acceptor compartment being on the second side of said membrane barrier, wherein said acceptor solution comprises a buffer of known pH and one or more sink-forming additives, wherein said sink-forming additives possess one or more of the properties selected from the group consisting of (1) high capacity to bind said compound, (2) low UV absorption, (3) high water solubility, and (4) low vapor pressure, d. preparing a donor-blank solution free of said compound, but otherwise of the same composition as said reference solution, e. preparing an acceptor-blank solution of the same composition as said initial acceptor solution, f. measuring a spectroscopic property of said compound in said reference, donor-blank, and acceptor-blank solutions at the start of the assay, g. measuring said spectroscopic property of said compound in each of said final donor and final acceptor solutions after known permeation time from the start of the assay, h. determining the relative concentration of said final donor and acceptor solutions by comparing the measured spectroscopic property of said final acceptor, final donor, reference, acceptor-blank and donor-blank solutions, and i. calculating from said determination the membrane permeability of said compound using the equation $$P_e^{(D)} = -\frac{2.303 V_D}{A(t-\tau_{SS})}\left(\frac{1}{1+r_a}\right)\log_{10}\left[-r_a + \left(\frac{1+r_a}{1-R}\right)\frac{C_D(t)}{C_D(0)}\right]$$

where R is membrane retention, calculated from the equation $$R = 1 - [C_D(t) + C_A(t) \cdot V_A/V_D]/C_D(0)$$

and where $$r_a = (V_D/V_A)(P_e^{(A)}/P_e^{(D)})$$

and where $P_e^{(D)}$ and $P_e^{(A)}$ are the membrane permeabilities in the donor-to-acceptor and in the acceptor-to-donor directions, respectively; $V_A$ and $V_D$ are volumes of the acceptor and donor compartments, respectively; A is the area of the membrane barrier; t is time; $\tau_{SS}$ is steady-state time; $C_A(t)$ and $C_D(t)$ are the acceptor and donor sample concentrations at time t, respectively; and $C_D(0)$ is the concentration of the initial donor solution.

2. The method of claim 1, wherein said spectroscopic property is measured using a method selected from the group consisting of UV spectrophotometry, visible range spectrophotometry, colorimetry, fluorimetry, polarimetry, optical rotation polarmetry, and circular dichroism spectroscopy.

3. The method of claim 1, wherein said compound is presented as a stock solution in DMSO and said spectroscopic property is UV range absorbance.

4. The method of claim 1, wherein properties of said membrane barrier are varied as a means of controlling R.

5. The method of claim 1, wherein said solutions in said donor and acceptor compartments have different pH values.

6. The method of claim 1, wherein said sink-forming additives are selected from the group consisting of (a) anionic surfactants, (b) bile salts, (c) uncharged cyclodextrins, (d) anionic cyclodextrins, (e) uncharged water-soluble lipophilic polymers, and (f) negatively-charged water-soluble lipophilic polymers.

7. The method of claim 6, wherein said anionic surfactant is sodium laurel sulfate.

8. The method of claim 6, wherein said cyclodextrin is β-cyclodextrin.

9. The method of claim 1, wherein said membrane barrier is supported on a microporous filter and comprises one or more negatively charged lipid components.

10. The method of claim 9, wherein one of said negatively-charged lipid compositions is a 20% soy lecithin lipid extract, possessing significant amounts of phosphatidylcholine, phosphatidylethanolamine, and phosphatidylinositol constituents, said soy lecithin lipid extract being dissolved in a nonpolar solvent.

11. The method of claim 9, wherein one of said negatively-charged lipid compositions is a 60% egg lecithin lipid extract, possessing significant amounts of phosphatidyicholine, phosphatidylethanolamine, and phosphatidylinositol constituents, said egg lecithin lipid extract being dissolved in a nonpolar solvent.

12. The method of claim 9, wherein said microporous filter is selected from the group consisting of: (a) hydrophobic PVDF, (b) hydrophilic PVDF, (c) hydrophilic VSWP, (d) hydrophilic GVHP mixed cellulose ester, and (e) polycarbonate filters.

13. The method of claim 9, wherein said lipid component is dissolved in a solvent selected from a group consisting of: (a) simple normal alkanes, $CH_3(CH_2)_nCH_3$, with n=8 to 16, (b) simple normal dienes, $CH_2$=$CH(CH_2)_nCH$=$CH_2$, with n=4 to 8, (c) simple normal alkenes, $CH_2$=$CH(CH_2)_nCH_3$, with n=5 to 13, (d) squalene, (e) octanol, and (f) olive oil.

14. The method of claim 10, wherein said soy lecithin lipid extract is present at 1–75% wt/vol in n-dodecane containing 1.5% absolute ethanol.

15. The method of claim 1, wherein said membrane barrier is supported on a microporous filter and comprises one or more lipids selected from a group consisting of (a) purified soy lecithin composed of a mixture of phosphatidylcholines, (b) purified egg lecithin composed of a mixture of phosphatidylcholines, (c) synthetic dioleoylphosphatidylcholine, and (d) cholesterol.

16. The method of claim 1, wherein said membrane barrier comprises a cultured cell monolayer selected from the group consisting of (a) epithelial Caco-2 (human colon carcinoma), (b) epithelial MDPK (Madin-Darby canine kidney), (c) HT29-MTX, and (d) rat endothelial RBE4.

17. The method of claim 1, wherein said membrane barrier comprises a silicone membrane.

18. The method of claim 1, wherein said membrane barrier comprises a dialysis membrane.

19. The method, of claim 1, wherein said donor-blank solution comprises one or more buffers selected from the group consisting of acetic acid, MES, HEPES and taurine dissolved in water, with concentrations selected to ensure constant buffer capacity in the pH interval from 3 to 10, adjusted to the desired donor pH value with an aliquot of standardized strong base titrant solution.

20. The method of claim 19, wherein said donor-blank solution further comprises one or more donor sink-forming additives.

21. The method of claim 19 wherein said buffer is HEPES, adjusted to the desired physiological pH value with an aliquot of standardized strong base titrant solution.

22. The method of claim 19, wherein
 a. said donor-blank solution is titrated with a standardized strong acid or strong base titrant solution in the pH interval 3–10;
 b. said titration procedure produces a titration curve, linearly relating volumes of titrant to pH values; and
 c. said titration curve is used to calculate the appropriate volume of said titrant to add to said reference, said initial donor, and said donor-blank solutions made with said buffer, to establish the pH values of the solutions, without actually having to measure the pH values of the solutions using a conventional pH electrode.

23. The method of claim 1, wherein said acceptor-blank solution comprises one or more buffers selected from the group consisting of acetic acid, MES, HEPES and taurine dissolved in water, with concentrations selected to ensure constant buffer capacity in the pH interval from 3 to 10, adjusted to the desired acceptor pH value with an aliquot of standardized strong base titrant solution.

24. The method of claim 23 wherein said acceptor-blank solution further comprises one or more acceptor sink-forming additives.

25. The method of claim 23 wherein said buffer is HEPES, adjusted to the desired physiological pH value with an aliquot of standardized strong base titrant solution.

26. The method of claim 23, wherein
 a. said acceptor-blank solution is titrated with a standardized strong acid or strong base titrant solution in the pH interval 3–10;
 b. said titration procedure produces a titration curve, linearly relating volumes of titrant to pH values; and
 c. said titration curve is used to calculate the appropriate volume of said titrant to add to said reference, said initial acceptor, and said acceptor-blank solutions made with said buffer, to establish the pH values of the solutions, without actually having to measure the pH values of the solutions using a conventional PH electrode.

* * * * *

UNITED STATES PATENT AND TRADEMARK OFFICE
CERTIFICATE OF CORRECTION

PATENT NO.          : 7,022,528 B2
APPLICATION NO. : 10/351263
DATED                  : April 4, 2006
INVENTOR(S)        : Alex Avdeef et al.

It is certified that error appears in the above-identified patent and that said Letters Patent is hereby corrected as shown below:

Column 26, claim 2, line 61, "UV spectrophotometry" should read --UV range spectrophotometry--;

Column 26, claim 2, line 63, "polarmetry" should read --polarimetry--; and

Column 27, claim 11, line 26, "phosphatidyicho-" should read --phosphatidylcho- --.

Signed and Sealed this

Sixth Day of March, 2007

JON W. DUDAS
*Director of the United States Patent and Trademark Office*